(12) United States Patent
Weir et al.

(10) Patent No.: US 11,160,861 B2
(45) Date of Patent: Nov. 2, 2021

(54) ADJUVANTING SYSTEMS AND WATER-FREE VACCINE COMPOSITIONS COMPRISING A POLYI:C POLYNUCLEOTIDE ADJUVANT AND A LIPID-BASED ADJUVANT

(71) Applicant: IMMUNOVACCINE TECHNOLOGIES INC., Dartmouth (CA)

(72) Inventors: Genevieve Mary Weir, Dartmouth (CA); Lisa Diana MacDonald, Halifax (CA); Robert Liwski, Halifax (CA); Marc Mansour, Halifax (CA)

(73) Assignee: IMMUNOVACCINE TECHNOLOGIES INC., Dartmouth (CA)

( * ) Notice: Subject to any disclaimer, the term of this patent is extended or adjusted under 35 U.S.C. 154(b) by 330 days.

(21) Appl. No.: 15/777,120

(22) PCT Filed: Nov. 15, 2016

(86) PCT No.: PCT/CA2016/051324
§ 371 (c)(1),
(2) Date: May 17, 2018

(87) PCT Pub. No.: WO2017/083963
PCT Pub. Date: May 26, 2017

(65) Prior Publication Data
US 2018/0339039 A1    Nov. 29, 2018

Related U.S. Application Data

(60) Provisional application No. 62/256,875, filed on Nov. 18, 2015.

(51) Int. Cl.
*A61K 39/39* (2006.01)
*A61K 39/07* (2006.01)
*A61K 39/12* (2006.01)
*A61K 39/00* (2006.01)

(52) U.S. Cl.
CPC .............. *A61K 39/39* (2013.01); *A61K 39/07* (2013.01); *A61K 39/12* (2013.01); *A61K 2039/55505* (2013.01); *A61K 2039/55516* (2013.01); *A61K 2039/55561* (2013.01); *A61K 2039/55572* (2013.01); *C12N 2710/20034* (2013.01); *C12N 2760/16134* (2013.01); *Y02A 50/30* (2018.01)

(58) Field of Classification Search
None
See application file for complete search history.

(56) References Cited

U.S. PATENT DOCUMENTS

| 8,216,495 B2 | 7/2012 | Janssens et al. |
| 8,216,595 B2 | 7/2012 | Moon et al. |

FOREIGN PATENT DOCUMENTS

| KR | 10-0900837 B1 | 6/2009 |
| KR | 20140119362 A | 10/2014 |
| WO | WO2009043165 A1 | 4/2009 |
| WO | WO2013049941 A1 | 4/2013 |
| WO | WO2014153636 A1 | 10/2014 |

OTHER PUBLICATIONS

Zaman et al (Frontiers in Immunol., 4 (318): 1-12, 2013).*
European Search Report dated Jun. 12, 2019 issued in corresponding European Patent Application No. 16865342.6.
Yu Zhou et al., "TLR3 activation efficiency by high or low molecular mass poly I:C", Innate Immunity, vol. 19, No. 2, Jan. 1, 2012, pp. 184-192.
Guy Bruno, "The perfect mix: recent progress in adjuvant research", Nature Reviews. Microbiology, Nature Publishing Group, GB, vol. 5, No. 7, Jul. 1, 2007, pp. 505-517.
Lim, SN. et al., Combined TLR stimulation with Pam3Cys and Poly I:C enhances Flt3-ligand dendritic cell activation for tumor immunotherapy. J. Immunother, 35(9), Nov.-Dec. 2012, pp. 670-679.
Office Action issued in JP Application No. 2018-524713 dated Aug. 25, 2020.
Third Party Submission in JP Application No. 2018-524713 dated Oct. 30, 2020.

* cited by examiner

*Primary Examiner* — Brian Gangle
(74) *Attorney, Agent, or Firm* — Troutman Pepper Hamilton Sanders LLP

(57) ABSTRACT

The present disclosure provides adjuvanting systems comprising: (a) a polyI:C polynucleotide adjuvant; (b) a lipid-based adjuvant; (c) an amphipathic compound; and (d) a hydrophobic carrier. Also provided are vaccine compositions that are water-free or substantially free of water, which comprise the same components together with one or more antigens. The disclosure also provides uses for such compositions in inducing an antibody (humoral) and/or cell-mediated immune response and methods for their use in the treatment of a disease, disorder or ailment ameliorated by an antibody and/or cell-mediated immune response.

28 Claims, 3 Drawing Sheets
Specification includes a Sequence Listing.

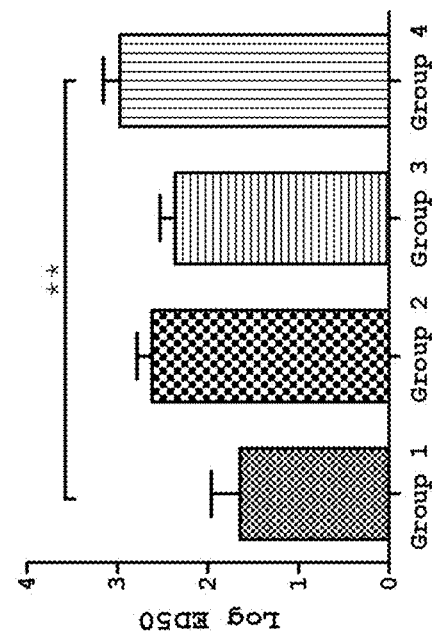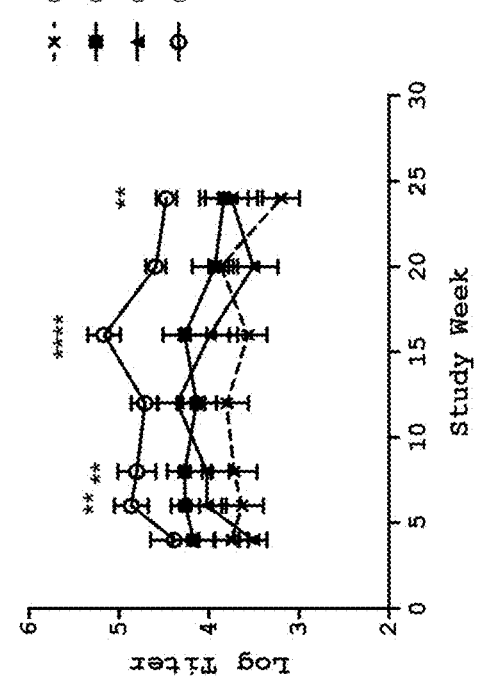

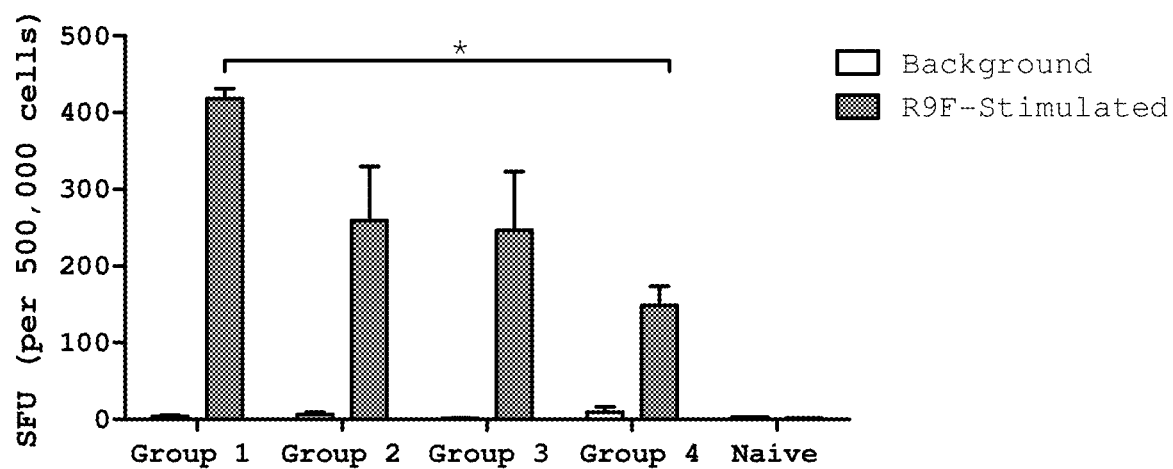

SEQUENCE LISTING

<160> NUMBER OF SEQ ID NOS: 80

<210> SEQ ID NO 1
<211> LENGTH: 6
<212> TYPE: PRT
<213> ORGANISM: Artificial Sequence
<220> FEATURE:
<223> OTHER INFORMATION: Palmitic Acid Adjuvant
<220> FEATURE:
<221> NAME/KEY: Misc_Feature
<222> LOCATION: (1)..(1)
<223> OTHER INFORMATION: Linked to PAM, PAM2 or PAM3

```
<220> FEATURE:
<221> NAME/KEY: Misc_Feature
<222> LOCATION: (6)..(6)
<223> OTHER INFORMATION: Optionally conjugated to Biotin-Aca-Aca,
      Fluorescein-Aca-Aca, Rhodamine-Aca-Aca, or FLAG-tag

<400> SEQUENCE: 1

Cys Ser Lys Lys Lys Lys
1               5

<210> SEQ ID NO 2
<211> LENGTH: 9
<212> TYPE: PRT
<213> ORGANISM: Artificial Sequence
<220> FEATURE:
<223> OTHER INFORMATION: HPV R9F peptide

<400> SEQUENCE: 2

Arg Ala His Tyr Asn Ile Val Thr Phe
1               5

<210> SEQ ID NO 3
<211> LENGTH: 26
<212> TYPE: DNA
<213> ORGANISM: Artificial Sequence
<220> FEATURE:
<223> OTHER INFORMATION: PolyI:C polynucleotide
<220> FEATURE:
<221> NAME/KEY: Modified_base
<222> LOCATION: (1)..(1)
<223> OTHER INFORMATION: Inosine
<220> FEATURE:
<221> NAME/KEY: Modified_base
<222> LOCATION: (3)..(3)
<223> OTHER INFORMATION: Inosine
<220> FEATURE:
<221> NAME/KEY: Modified_base
<222> LOCATION: (5)..(5)
<223> OTHER INFORMATION: Inosine
<220> FEATURE:
<221> NAME/KEY: Modified_base
<222> LOCATION: (7)..(7)
<223> OTHER INFORMATION: Inosine
<220> FEATURE:
<221> NAME/KEY: Modified_base
<222> LOCATION: (9)..(9)
<223> OTHER INFORMATION: Inosine
<220> FEATURE:
<221> NAME/KEY: Modified_base
<222> LOCATION: (11)..(11)
<223> OTHER INFORMATION: Inosine
<220> FEATURE:
<221> NAME/KEY: Modified_base
<222> LOCATION: (13)..(13)
<223> OTHER INFORMATION: Inosine
<220> FEATURE:
<221> NAME/KEY: Modified_base
<222> LOCATION: (15)..(15)
<223> OTHER INFORMATION: Inosine
<220> FEATURE:
<221> NAME/KEY: Modified_base
<222> LOCATION: (17)..(17)
<223> OTHER INFORMATION: Inosine
<220> FEATURE:
<221> NAME/KEY: Modified_base
<222> LOCATION: (19)..(19)
<223> OTHER INFORMATION: Inosine
<220> FEATURE:
<221> NAME/KEY: Modified_base
<222> LOCATION: (21)..(21)
<223> OTHER INFORMATION: Inosine
<220> FEATURE:
<221> NAME/KEY: Modified_base
<222> LOCATION: (23)..(23)
<223> OTHER INFORMATION: Inosine
```

```
<220> FEATURE:
<221> NAME/KEY: Modified_base
<222> LOCATION: (25)..(25)
<223> OTHER INFORMATION: Inosine

<400> SEQUENCE: 3 ncncncnc ncncncnc ncncnc                                              26

<210> SEQ ID NO 4
<211> LENGTH: 6
<212> TYPE: DNA
<213> ORGANISM: Artificial Sequence
<220> FEATURE:
<223> OTHER INFORMATION: Synthetic polynucleotide
<220> FEATURE:
<221> NAME/KEY: Modified_base
<222> LOCATION: (1)..(2)
<223> OTHER INFORMATION: Inosine
<220> FEATURE:
<221> NAME/KEY: Modified_base
<222> LOCATION: (4)..(5)
<223> OTHER INFORMATION: Inosine

<400> SEQUENCE: 4 nncnnc                                                                 6

<210> SEQ ID NO 5
<211> LENGTH: 6
<212> TYPE: DNA
<213> ORGANISM: Artificial Sequence
<220> FEATURE:
<223> OTHER INFORMATION: Synthetic polynucleotide
<220> FEATURE:
<221> NAME/KEY: Modified_base
<222> LOCATION: (1)..(1)
<223> OTHER INFORMATION: Inosine
<220> FEATURE:
<221> NAME/KEY: Modified_base
<222> LOCATION: (3)..(3)
<223> OTHER INFORMATION: Inosine
<220> FEATURE:
<221> NAME/KEY: Modified_base
<222> LOCATION: (5)..(5)
<223> OTHER INFORMATION: Inosine

<400> SEQUENCE: 5 ncncnc                                                                 6

<210> SEQ ID NO 6
<211> LENGTH: 16
<212> TYPE: PRT
<213> ORGANISM: Artificial Sequence
<220> FEATURE:
<223> OTHER INFORMATION: Palmitic Acid Adjuvant
<220> FEATURE:
<221> NAME/KEY: Misc_Feature
<222> LOCATION: (1)..(1)
<223> OTHER INFORMATION: Linked to PAM3

<400> SEQUENCE: 6

Cys Ser Ser Asn Ala Lys Ile Asp Gln Leu Ser Ser Asp Val Gln Thr
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Palmitic Acid Adjuvant
<220> FEATURE:
<221> NAME/KEY: Misc_feature
```

```
<222> LOCATION: (1)..(1)
<223> OTHER INFORMATION: Linked to PAM3

<400> SEQUENCE: 7

Cys Ser Ser Asn Lys Ser Thr Thr Gly Ser Gly Glu Thr Thr Thr Ala
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Palmitic Acid Adjuvant
<220> FEATURE:
<221> NAME/KEY: Misc_Feature
<222> LOCATION: (1)..(1)
<223> OTHER INFORMATION: Linked to PAM3

<400> SEQUENCE: 8

Cys Ser Ser Thr Lys Pro Val Ser Gln Asp Thr Ser Pro Lys Pro Ala
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Palmitic Acid Adjuvant
<220> FEATURE:
<221> NAME/KEY: Misc_feature
<222> LOCATION: (1)..(1)
<223> OTHER INFORMATION: Linked to PAM3

<400> SEQUENCE: 9

Cys Ser Ser Gly Ser Lys Pro Ser Gly Gly Pro Leu Pro Asp Ala Lys
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Palmitic Acid Adjuvant
<220> FEATURE:
<221> NAME/KEY: Misc_feature
<222> LOCATION: (1)..(1)
<223> OTHER INFORMATION: Linked to PAM3

<400> SEQUENCE: 10

Cys Ser Ser Gly Asn Lys Ser Ala Pro Ser Ser Ala Ser Ser Ser Ser
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Palmitic Acid Adjuvant
<220> FEATURE:
<221> NAME/KEY: Misc_feature
<222> LOCATION: (1)..(1)
<223> OTHER INFORMATION: Linked to PAM3

<400> SEQUENCE: 11

Cys Gly Ser His Gln Met Lys Ser Glu Gly His Ala Asn Met Gln Leu
1               5                   10                  15

<210> SEQ ID NO 12
<211> LENGTH: 16
```

```
<212> TYPE: PRT
<213> ORGANISM: Artificial Sequence
<220> FEATURE:
<223> OTHER INFORMATION: Palmitic Acid Adjuvant
<220> FEATURE:
<221> NAME/KEY: Misc_feature
<222> LOCATION: (1)..(1)
<223> OTHER INFORMATION: Linked to PAM3

<400> SEQUENCE: 12

Cys Ser Ser Ser Asn Asn Asp Ala Ala Gly Asn Gly Ala Ala Gln Thr
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Palmitic Acid Adjuvant
<220> FEATURE:
<221> NAME/KEY: Misc_feature
<222> LOCATION: (1)..(1)
<223> OTHER INFORMATION: Linked to PAM3

<400> SEQUENCE: 13

Cys Lys Gln Asn Val Ser Ser Leu Asp Glu Lys Asn Ser Val Ser Val
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Palmitic Acid Adjuvant
<220> FEATURE:
<221> NAME/KEY: Misc_feature
<222> LOCATION: (1)..(1)
<223> OTHER INFORMATION: Linked to PAM3

<400> SEQUENCE: 14

Cys Asn Asn Ser Gly Lys Asp Gly Asn Thr Ser Ala Asn Ser Ala Asp
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Palmitic Acid Adjuvant
<220> FEATURE:
<221> NAME/KEY: Misc_feature
<222> LOCATION: (1)..(1)
<223> OTHER INFORMATION: Linked to PAM3

<400> SEQUENCE: 15

Cys Asn Asn Gly Gly Pro Glu Leu Lys Ser Asp Glu Val Ala Lys Ser
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Palmitic Acid Adjuvant
<220> FEATURE:
<221> NAME/KEY: Misc_feature
<222> LOCATION: (1)..(1)
<223> OTHER INFORMATION: Linked to PAM3

<400> SEQUENCE: 16
```

Cys Ser Gln Glu Pro Ala Ala Pro Ala Ala Glu Ala Thr Pro Ala Gly
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Palmitic Acid Adjuvant
<220> FEATURE:
<221> NAME/KEY: Misc_feature
<222> LOCATION: (1)..(1)
<223> OTHER INFORMATION: Linked to PAM3

<400> SEQUENCE: 17

Cys Ser Ser Ser Lys Ser Ser Asp Ser Ser Ala Pro Lys Ala Tyr Gly
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Palmitic Acid Adjuvant
<220> FEATURE:
<221> NAME/KEY: Misc_feature
<222> LOCATION: (1)..(1)
<223> OTHER INFORMATION: Linked to PAM3

<400> SEQUENCE: 18

Cys Ala Gln Glu Lys Glu Ala Lys Ser Glu Leu Asp Tyr Asp Gln Thr
1               5                   10                  15

<210> SEQ ID NO 19
<211> LENGTH: 5
<212> TYPE: PRT
<213> ORGANISM: Artificial Sequence
<220> FEATURE:
<223> OTHER INFORMATION: Palmitic Acid Adjuvant
<220> FEATURE:
<221> NAME/KEY: Misc_feature
<222> LOCATION: (1)..(1)
<223> OTHER INFORMATION: Linked to PAM-CYS(PAM) or PAM-Dhc

<400> SEQUENCE: 19

Ser Lys Lys Lys Lys
1               5

<210> SEQ ID NO 20
<211> LENGTH: 10
<212> TYPE: PRT
<213> ORGANISM: Artificial Sequence
<220> FEATURE:
<223> OTHER INFORMATION: Synthetic diacylated lipoprotein FSL-1
<220> FEATURE:
<221> NAME/KEY: Misc_feature
<222> LOCATION: (1)..(1)
<223> OTHER INFORMATION: Linked to PAM or PAM2

<400> SEQUENCE: 20

Cys Gly Asp Pro Lys His Pro Lys Ser Phe
1               5                   10

<210> SEQ ID NO 21
<211> LENGTH: 9
<212> TYPE: PRT
<213> ORGANISM: Artificial Sequence
<220> FEATURE:
<223> OTHER INFORMATION: Palmitic Acid Adjuvant
<220> FEATURE:

```
<221> NAME/KEY: Misc_feature
<222> LOCATION: (1)..(1)
<223> OTHER INFORMATION: Linked to PAM-Dhc

<400> SEQUENCE: 21

Gly Asp Pro Lys His Pro Lys Ser Phe
1               5

<210> SEQ ID NO 22
<211> LENGTH: 23
<212> TYPE: PRT
<213> ORGANISM: Artificial Sequence
<220> FEATURE:
<223> OTHER INFORMATION: RSV SHe A peptide

<400> SEQUENCE: 22

Asn Lys Leu Cys Glu Tyr Asn Val Phe His Asn Lys Thr Phe Glu Leu
1               5                   10                  15

Pro Arg Ala Arg Val Asn Thr
            20

<210> SEQ ID NO 23
<211> LENGTH: 9
<212> TYPE: PRT
<213> ORGANISM: Artificial Sequence
<220> FEATURE:
<223> OTHER INFORMATION: Synthetic peptide

<400> SEQUENCE: 23

Ala Ala Gly Ile Gly Ile Leu Thr Val
1               5

<210> SEQ ID NO 24
<211> LENGTH: 10
<212> TYPE: PRT
<213> ORGANISM: Artificial Sequence
<220> FEATURE:
<223> OTHER INFORMATION: Synthetic peptide

<400> SEQUENCE: 24

Glu Ala Ala Gly Ile Gly Ile Leu Thr Val
1               5                   10

<210> SEQ ID NO 25
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 25

Ile Leu Thr Val Ile Leu Gly Val Leu
1               5

<210> SEQ ID NO 26
<211> LENGTH: 10
<212> TYPE: PRT
<213> ORGANISM: Artificial Sequence
<220> FEATURE:
<223> OTHER INFORMATION: Synthetic peptide

<400> SEQUENCE: 26

Ala Glu Glu Ala Ala Gly Ile Gly Ile Leu
1               5                   10

<210> SEQ ID NO 27
```

```
<211> LENGTH: 11
<212> TYPE: PRT
<213> ORGANISM: Artificial Sequence
<220> FEATURE:
<223> OTHER INFORMATION: Synthetic peptide

<400> SEQUENCE: 27

Ala Glu Glu Ala Ala Gly Ile Gly Ile Leu Thr
1               5                   10

<210> SEQ ID NO 28
<211> LENGTH: 9
<212> TYPE: PRT
<213> ORGANISM: Artificial Sequence
<220> FEATURE:
<223> OTHER INFORMATION: Synthetic peptide

<400> SEQUENCE: 28

Thr Ile Leu Leu Gly Ile Phe Phe Leu
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic peptide

<400> SEQUENCE: 29

Phe Leu Ala Leu Ile Ile Cys Asn Ala
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic peptide

<400> SEQUENCE: 30

Lys Thr Trp Gly Gln Tyr Trp Gln Val
1               5

<210> SEQ ID NO 31
<211> LENGTH: 10
<212> TYPE: PRT
<213> ORGANISM: Artificial Sequence
<220> FEATURE:
<223> OTHER INFORMATION: Synthetic peptide

<400> SEQUENCE: 31

Ala Met Leu Gly Thr His Thr Met Glu Val
1               5                   10

<210> SEQ ID NO 32
<211> LENGTH: 9
<212> TYPE: PRT
<213> ORGANISM: Artificial Sequence
<220> FEATURE:
<223> OTHER INFORMATION: Synthetic peptide

<400> SEQUENCE: 32

Met Leu Gly Thr His Thr Met Glu Val
1               5

<210> SEQ ID NO 33
<211> LENGTH: 10
```

```
<212> TYPE: PRT
<213> ORGANISM: Artificial Sequence
<220> FEATURE:
<223> OTHER INFORMATION: Synthetic peptide

<400> SEQUENCE: 33

Ser Leu Ala Asp Thr Asn Ser Leu Ala Val
1               5                   10

<210> SEQ ID NO 34
<211> LENGTH: 9
<212> TYPE: PRT
<213> ORGANISM: Artificial Sequence
<220> FEATURE:
<223> OTHER INFORMATION: Synthetic peptide

<400> SEQUENCE: 34

Ile Thr Asp Gln Val Pro Phe Ser Val
1               5

<210> SEQ ID NO 35
<211> LENGTH: 10
<212> TYPE: PRT
<213> ORGANISM: Artificial Sequence
<220> FEATURE:
<223> OTHER INFORMATION: Synthetic peptide

<400> SEQUENCE: 35

Leu Leu Asp Gly Thr Ala Thr Leu Arg Leu
1               5                   10

<210> SEQ ID NO 36
<211> LENGTH: 9
<212> TYPE: PRT
<213> ORGANISM: Artificial Sequence
<220> FEATURE:
<223> OTHER INFORMATION: Synthetic peptide

<400> SEQUENCE: 36

Tyr Leu Glu Pro Gly Pro Val Thr Ala
1               5

<210> SEQ ID NO 37
<211> LENGTH: 10
<212> TYPE: PRT
<213> ORGANISM: Artificial Sequence
<220> FEATURE:
<223> OTHER INFORMATION: Synthetic peptide

<400> SEQUENCE: 37

Val Leu Tyr Arg Tyr Gly Ser Phe Ser Val
1               5                   10

<210> SEQ ID NO 38
<211> LENGTH: 9
<212> TYPE: PRT
<213> ORGANISM: Artificial Sequence
<220> FEATURE:
<223> OTHER INFORMATION: Synthetic peptide

<400> SEQUENCE: 38

Arg Leu Pro Arg Ile Phe Cys Ser Cys
1               5

<210> SEQ ID NO 39
<211> LENGTH: 9
<212> TYPE: PRT
```

```
<213> ORGANISM: Artificial Sequence
<220> FEATURE:
<223> OTHER INFORMATION: Synthetic peptide

<400> SEQUENCE: 39

Leu Ile Tyr Arg Arg Arg Leu Met Lys
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic peptide

<400> SEQUENCE: 40

Ala Leu Asn Phe Pro Gly Ser Gln Lys
1               5

<210> SEQ ID NO 41
<211> LENGTH: 10
<212> TYPE: PRT
<213> ORGANISM: Artificial Sequence
<220> FEATURE:
<223> OTHER INFORMATION: Synthetic peptide

<400> SEQUENCE: 41

Ser Leu Ile Tyr Arg Arg Arg Leu Met Lys
1               5                   10

<210> SEQ ID NO 42
<211> LENGTH: 9
<212> TYPE: PRT
<213> ORGANISM: Artificial Sequence
<220> FEATURE:
<223> OTHER INFORMATION: Synthetic peptide

<400> SEQUENCE: 42

Ala Leu Leu Ala Val Gly Ala Thr Lys
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic peptide

<400> SEQUENCE: 43

Val Tyr Phe Phe Leu Pro Asp His Leu
1               5

<210> SEQ ID NO 44
<211> LENGTH: 8
<212> TYPE: PRT
<213> ORGANISM: Artificial Sequence
<220> FEATURE:
<223> OTHER INFORMATION: Synthetic peptide

<400> SEQUENCE: 44

Ser Asn Asp Gly Pro Thr Leu Ile
1               5

<210> SEQ ID NO 45
<211> LENGTH: 10
<212> TYPE: PRT
<213> ORGANISM: Artificial Sequence
```

```
<220> FEATURE:
<223> OTHER INFORMATION: Synthetic peptide

<400> SEQUENCE: 45

Val Ser His Ser Phe Pro His Pro Leu Tyr
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Synthetic peptide

<400> SEQUENCE: 46

Phe Leu Thr Pro Lys Lys Leu Gln Cys Val
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Synthetic peptide

<400> SEQUENCE: 47

Val Ile Ser Asn Asp Val Cys Ala Gln Val
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Synthetic peptide

<400> SEQUENCE: 48

His Ser Thr Asn Gly Val Thr Arg Ile Tyr
1               5                   10

<210> SEQ ID NO 49
<211> LENGTH: 9
<212> TYPE: PRT
<213> ORGANISM: Artificial Sequence
<220> FEATURE:
<223> OTHER INFORMATION: Synthetic peptide

<400> SEQUENCE: 49

Lys Cys Asp Ile Cys Thr Asp Glu Tyr
1               5

<210> SEQ ID NO 50
<211> LENGTH: 11
<212> TYPE: PRT
<213> ORGANISM: Artificial Sequence
<220> FEATURE:
<223> OTHER INFORMATION: Synthetic peptide

<400> SEQUENCE: 50

Ser Ser Asp Tyr Val Ile Pro Ile Gly Thr Tyr
1               5                   10

<210> SEQ ID NO 51
<211> LENGTH: 9
<212> TYPE: PRT
<213> ORGANISM: Artificial Sequence
<220> FEATURE:
```

```
<223> OTHER INFORMATION: Synthetic peptide

<400> SEQUENCE: 51

Tyr Met Asp Gly Thr Met Ser Gln Val
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic peptide

<400> SEQUENCE: 52

Met Leu Leu Ala Val Leu Tyr Cys Leu
1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic peptide

<400> SEQUENCE: 53

Ala Phe Leu Pro Trp His Arg Leu Phe
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic peptide

<400> SEQUENCE: 54

Ser Glu Ile Trp Arg Asp Ile Asp Phe
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic peptide

<400> SEQUENCE: 55

Met Ser Leu Gln Arg Gln Phe Leu Arg
1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic peptide

<400> SEQUENCE: 56

Ser Val Tyr Asp Phe Phe Val Trp Leu
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic peptide
```

```
<400> SEQUENCE: 57

Thr Leu Asp Ser Gln Val Met Ser Leu
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic peptide

<400> SEQUENCE: 58

Leu Leu Gly Pro Gly Arg Pro Tyr Arg
1               5

<210> SEQ ID NO 59
<211> LENGTH: 9
<212> TYPE: PRT
<213> ORGANISM: Artificial Sequence
<220> FEATURE:
<223> OTHER INFORMATION: Synthetic peptide

<400> SEQUENCE: 59

Ala Asn Asp Pro Ile Phe Val Val Leu
1               5

<210> SEQ ID NO 60
<211> LENGTH: 10
<212> TYPE: PRT
<213> ORGANISM: Artificial Sequence
<220> FEATURE:
<223> OTHER INFORMATION: HPV T10V peptide

<400> SEQUENCE: 60

Thr Ile His Asp Ile Ile Leu Glu Cys Val
1               5                   10

<210> SEQ ID NO 61
<211> LENGTH: 10
<212> TYPE: PRT
<213> ORGANISM: Artificial Sequence
<220> FEATURE:
<223> OTHER INFORMATION: HPV Y10T peptide

<400> SEQUENCE: 61

Tyr Met Leu Asp Leu Gln Pro Glu Thr Thr
1               5                   10

<210> SEQ ID NO 62
<211> LENGTH: 9
<212> TYPE: PRT
<213> ORGANISM: Artificial Sequence
<220> FEATURE:
<223> OTHER INFORMATION: HPV L9V peptide

<400> SEQUENCE: 62

Leu Leu Met Gly Thr Leu Gly Ile Val
1               5

<210> SEQ ID NO 63
<211> LENGTH: 8
<212> TYPE: PRT
<213> ORGANISM: Artificial Sequence
<220> FEATURE:
<223> OTHER INFORMATION: HPV T8I peptide
```

<400> SEQUENCE: 63

Thr Leu Gly Ile Val Cys Pro Ile
1               5

<210> SEQ ID NO 64
<211> LENGTH: 8
<212> TYPE: PRT
<213> ORGANISM: Artificial Sequence
<220> FEATURE:
<223> OTHER INFORMATION: TRP-2 V8L peptide

<400> SEQUENCE: 64

Val Tyr Asp Phe Phe Val Trp Leu
1               5

<210> SEQ ID NO 65
<211> LENGTH: 9
<212> TYPE: PRT
<213> ORGANISM: Artificial Sequence
<220> FEATURE:
<223> OTHER INFORMATION: p53 K9M peptide

<400> SEQUENCE: 65

Lys Tyr Met Cys Asn Ser Ser Cys Met
1               5

<210> SEQ ID NO 66
<211> LENGTH: 9
<212> TYPE: PRT
<213> ORGANISM: Artificial Sequence
<220> FEATURE:
<223> OTHER INFORMATION: p53 mK9M peptide

<400> SEQUENCE: 66

Lys Tyr Ile Cys Asn Ser Ser Cys Met
1               5

<210> SEQ ID NO 67
<211> LENGTH: 22
<212> TYPE: PRT
<213> ORGANISM: Artificial Sequence
<220> FEATURE:
<223> OTHER INFORMATION: PADRE and p53 mK9M peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 67

Ala Lys Xaa Val Ala Ala Trp Thr Leu Lys Ala Ala Ala Lys Tyr Ile
1               5                   10                  15

Cys Asn Ser Ser Cys Met
            20

<210> SEQ ID NO 68
<211> LENGTH: 429
<212> TYPE: DNA
<213> ORGANISM: Homo sapiens

<400> SEQUENCE: 68
atgggtgccc cgacgttgcc ccctgcctgg cagcccttc tcaaggacca ccgcatctct    60
acattcaaga actggcccct cttggagggc tgcgcctgca ccccggagcg gatggccgag   120
gctggcttca tccactgccc cactgagaac gagccagact ggcccagtg tttcttctgc   180 ttcaaggagc tggaaggctg ggagccagat gacgacccca tagaggaaca taaaaagcat   240

```
tcgtccggtt gcgctttcct ttctgtcaag aagcagtttg aagaattaac ccttggtgaa    300 ttttttgaaac tggacagaga aagagccaag aacaaaattg caaaggaaac caacaataag    360
aagaaagaat ttgaggaaac tgcgaagaaa gtgcgccgtg ccatcgagca gctggctgcc    420
atggattga                                                              429
```

```
<210> SEQ ID NO 69
<211> LENGTH: 142
<212> TYPE: PRT
<213> ORGANISM: Homo sapiens

<400> SEQUENCE: 69
```

Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Cys Phe Phe Cys Phe Lys Glu Leu
    50                  55                  60

Glu Gly Trp Glu Pro Asp Asp Asp Pro Ile Glu His Lys Lys His
65                  70                  75                  80

Ser Ser Gly Cys Ala Phe Leu Ser Val Lys Lys Gln Phe Glu Glu Leu
                85                  90                  95

Thr Leu Gly Glu Phe Leu Lys Leu Asp Arg Glu Arg Ala Lys Asn Lys
            100                 105                 110

Ile Ala Lys Glu Thr Asn Asn Lys Lys Lys Glu Phe Glu Glu Thr Ala
        115                 120                 125

Lys Lys Val Arg Arg Ala Ile Glu Gln Leu Ala Ala Met Asp
    130                 135                 140

```
<210> SEQ ID NO 70
<211> LENGTH: 9
<212> TYPE: PRT
<213> ORGANISM: Artificial Sequence
<220> FEATURE:
<223> OTHER INFORMATION: Survivin HLA-A1 wild type

<400> SEQUENCE: 70
```

Phe Glu Glu Leu Thr Leu Gly Glu Phe
1               5

```
<210> SEQ ID NO 71
<211> LENGTH: 9
<212> TYPE: PRT
<213> ORGANISM: Artificial Sequence
<220> FEATURE:
<223> OTHER INFORMATION: Survivin HLA-A1 modified

<400> SEQUENCE: 71
```

Phe Thr Glu Leu Thr Leu Gly Glu Phe
1               5

```
<210> SEQ ID NO 72
<211> LENGTH: 9
<212> TYPE: PRT
<213> ORGANISM: Artificial Sequence
<220> FEATURE:
<223> OTHER INFORMATION: Survivin HLA-A2 wild type

<400> SEQUENCE: 72
```

```
Leu Thr Leu Gly Glu Phe Leu Lys Leu
1               5

<210> SEQ ID NO 73
<211> LENGTH: 9
<212> TYPE: PRT
<213> ORGANISM: Artificial Sequence
<220> FEATURE:
<223> OTHER INFORMATION: Survivin HLA-A2 modified

<400> SEQUENCE: 73

Leu Met Leu Gly Glu Phe Leu Lys Leu
1               5

<210> SEQ ID NO 74
<211> LENGTH: 10
<212> TYPE: PRT
<213> ORGANISM: Artificial Sequence
<220> FEATURE:
<223> OTHER INFORMATION: Survivin HLA-A3 wild type

<400> SEQUENCE: 74

Arg Ile Ser Thr Phe Lys Asn Trp Pro Phe
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Surivivin HLA-A3 modified

<400> SEQUENCE: 75

Arg Ile Ser Thr Phe Lys Asn Trp Pro Lys
1               5                   10

<210> SEQ ID NO 76
<211> LENGTH: 9
<212> TYPE: PRT
<213> ORGANISM: Artificial Sequence
<220> FEATURE:
<223> OTHER INFORMATION: Survivin HLA-A24 wild type

<400> SEQUENCE: 76

Ser Thr Phe Lys Asn Trp Pro Phe Leu
1               5

<210> SEQ ID NO 77
<211> LENGTH: 9
<212> TYPE: PRT
<213> ORGANISM: Artificial Sequence
<220> FEATURE:
<223> OTHER INFORMATION: Surivivin HLA-B7 wild type

<400> SEQUENCE: 77

Leu Pro Pro Ala Trp Gln Pro Phe Leu
1               5

<210> SEQ ID NO 78
<211> LENGTH: 16
<212> TYPE: PRT
<213> ORGANISM: Artificial Sequence
<220> FEATURE:
<223> OTHER INFORMATION: Tetanus toxin peptide A16L

<400> SEQUENCE: 78
```

```
Ala Gln Tyr Ile Lys Ala Asn Ser Lys Phe Ile Gly Ile Thr Glu Leu
1               5                   10                  15

<210> SEQ ID NO 79
<211> LENGTH: 13
<212> TYPE: PRT
<213> ORGANISM: Artificial Sequence
<220> FEATURE:
<223> OTHER INFORMATION: T-helper epitope PADRE
<220> FEATURE:
<221> NAME/KEY: Misc_feature
<222> LOCATION: (3)..(3)
<223> OTHER INFORMATION: Xaa may be cyclohexylalanyl

<400> SEQUENCE: 79

Ala Lys Xaa Val Ala Ala Trp Thr Leu Lys Ala Ala Ala
1               5                   10

<210> SEQ ID NO 80
<211> LENGTH: 21
<212> TYPE: PRT
<213> ORGANISM: Artificial Sequence
<220> FEATURE:
<223> OTHER INFORMATION: Tetanus toxoid peptide F21E

<400> SEQUENCE: 80

Phe Asn Asn Phe Thr Val Ser Phe Trp Leu Arg Val Pro Lys Val Ser
1               5                   10                  15

Ala Ser His Leu Glu
            20
```

ADJUVANTING SYSTEMS AND WATER-FREE VACCINE COMPOSITIONS COMPRISING A POLYI:C POLYNUCLEOTIDE ADJUVANT AND A LIPID-BASED ADJUVANT

CROSS-REFERENCE TO RELATED APPLICATIONS

This application is a National Stage of International Application No. PCT/CA2016/051324, filed Nov. 15, 2016, which claims the benefit of and priority to U.S. Provisional Patent Application No. 62/256,875 filed on Nov. 18, 2015, the contents of each of which are herein fully incorporated by reference in their entirety.

SEQUENCE LISTING

This application contains a Sequence Listing which has been submitted in ASCII format via EFS-Web and is hereby incorporated by reference herein in its entirety. The ASCII text file was created on Nov. 22, 2016, is named Sequence Listing.txt and is 21,463 bytes in size.

FIELD

The present disclosure relates generally to adjuvanting systems and vaccine compositions that have enhanced efficacy in inducing and/or potentiating antigen-specific humoral and cell-mediated immune responses in immunized subjects.

BACKGROUND

Vaccines containing defined protein or peptide antigens are not immunogenic enough to generate rapid and prolonged immunity. This can sometimes be overcome with the use of an adjuvant to boost the immune response towards an antigen (Schijns and Lavelle 2011). There are generally two broad categories of adjuvants: delivery systems and immune-stimulants (Dubensky and Reed 2010, Schijns and Lavelle 2011, Hafner, Corthesy et al. 2013). The delivery system of a vaccine can act as an adjuvant by providing stability and prolonged interaction of the antigen with the immune system (Alving, Peachman et al. 2012). Vaccines may also incorporate molecular compounds with immune-stimulatory activity as adjuvants with the aim of further enhancing immunogenicity of the vaccine by directly activating cells of the immune system.

Immune-stimulant adjuvants are defined molecular agonists that are recognized by the immune system via specialized receptors, for example polyI:C stimulates Toll-like receptor 3 and Pam3CSK4 (SEQ ID NO: 1) stimulates Toll-like receptor 1/2 (Duthie, Windish et al. 2011, Ogawa, Liu et al. 2011). Immune-stimulants can activate the immune system and also direct the type of immune response generated towards a vaccine antigen. For example, the effectiveness of many vaccines is correlated to the generation of antibodies; however, for other types of vaccines a strong cytotoxic immune response primarily mediated by CD8+ T cells is desired. The type of immune response generated towards a vaccine antigen can be manipulated by including immune-stimulants that activate particular receptors found on immune cells that can initiate these responses through generation of cytokines and chemokines.

Aluminum-based adjuvants (collectively referred to as alum) are the most common in currently licensed human and veterinary vaccines (Gupta 1998, Wilson-Welder, Torres et al. 2009). Alum vaccines are prepared by mixing antigen to an aluminum salt, such as aluminum hydroxide or aluminum phosphate (Gupta 1998, Stills 2005). Upon injection, alum forms a short-lived depot for antigen (Gupta, Chang et al. 1996) and promotes phagocytosis of the vaccine by macrophages (Heimlich, Regnier et al. 1999, Rimaniol, Gras et al. 2004). Alum adjuvants can also act as immune-stimulators as they have been shown to activate the NLRP3 inflammasome expressed by innate immune cells (Kang and Locksley 2009, He, Zou et al. 2015). Alum also indirectly activates various danger-sensing receptors by causing necrosis at the site of immunization, potentiating the inflammatory response through recruitment of immune cells (Kool, Soullie et al. 2008). Alum adjuvants tend to induce a type 2 immune response characterized by IL-4 production, IgG1 and IgE antibodies and eosinophil activation (Wilson-Welder, Torres et al. 2009).

Emulsion-formulation vaccines are an alternative to aluminum-based vaccines. These formulations are prepared by emulsifying antigens dissolved in an aqueous buffer with an oil, such as Freunds incomplete adjuvant (IFA) or a mannide oleate in mineral oil solution (e.g. MONTANIDE™ ISA51 VG). Emulsion formulations also form a short-lived depot to facilitate vaccine phagocytosis by innate immune cells and also results in a type 2 immune response (Leenaars, Koedam et al. 1998). The oils used in the emulsion can impart unique immune stimulation and have been shown to result in stronger immune responses than alum-adjuvanted vaccines (De Gregorio, Caproni et al. 2013). However, emulsion formulations can result in T cell tolerance as a result of ineffective presentation of antigen to the immune system (Aichele, Brduscha-Riem et al. 1995, Hailemichael, Dai et al. 2013). Emulsion formulations are also limited by practical considerations, such as they can be cumbersome to prepare, must be stored at 2-8° C. and have a limited shelf life (Koh, Higgins et al. 2006, Kumru, Joshi et al. 2014). Furthermore, emulsion formulations are associated with toxicity and reactogenicity which has precluded their approval for human use (Graham, McElrath et al. 2010).

Finding optimal adjuvanting systems is difficult because the interaction or association between and among delivery system type adjuvants and/or immune-stimulant type adjuvants can have unpredictable effects, and antagonism or anergy can often occur rather than synergy.

There remains a need for the development of adjuvanting systems and vaccine compositions for generating strong humoral and cell-mediated immune responses against a variety of antigens. In the present disclosure, we describe novel adjuvanting systems and vaccine compositions for enhancing antigen-specific immunogenicity.

SUMMARY

In an embodiment, the present disclosure relates to an adjuvanting system comprising: (a) a polyI:C polynucleotide adjuvant; (b) a lipid-based adjuvant; (c) an amphipathic compound; and (d) a hydrophobic carrier.

In another embodiment, the present disclosure relates to a composition comprising: (a) an antigen; (b) a polyI:C polynucleotide adjuvant; (c) a lipid-based adjuvant; (d) an amphipathic compound; and (e) a hydrophobic carrier. As described herein, the composition is water-free or substantially free of water.

In some embodiments of the adjuvanting system and compositions described herein, the lipid-based adjuvant comprises at least one palmitic acid moiety, such as for example a palmitic acid adjuvant as described herein. In a particular embodiment, the lipid-based adjuvant is Pam-3-Cys-Ser-(Lys)4 (Pam3CSK4; SEQ ID NO: 1).

In some embodiments of the adjuvanting system and compositions described herein, the polyI:C polynucleotide adjuvant is a traditional form of polyI:C with an approximate molecular weight of 989,486 Daltons, containing a mixture of varying strand lengths of polyI and polyC (Thermo Scientific; USA).

In some embodiments of the adjuvanting system and compositions described herein, the amphipathic compound is a phospholipid, such as for example DOPC or S100 lecithin, which in an embodiment is used together with cholesterol.

In some embodiments of the adjuvanting system and compositions described herein, the hydrophobic carrier is an oil, such as for example a mannide oleate in mineral oil solution (e.g. MONTANIDE™ ISA51).

In another embodiment, the present disclosure relates to a method comprising administering the composition as described herein to a subject in need thereof, for inducing an antibody response and/or cell-mediated immune response to said antigen in said subject.

In another embodiment, the present disclosure relates to a method for the treatment and/or prevention of a disease caused by a bacterium, a virus, a fungus, a parasite, an allergen, or a tumor cell that expresses the antigen, said method comprising administering the composition as described herein to a subject.

In another embodiment, the present disclosure relates to a method for the treatment and/or prevention of a neurodegenerative disease, wherein the neurodegenerative disease is associated with expression of the antigen, said method comprising administering the composition as described herein to a subject.

In another embodiment, the present disclosure relates to a method for neutralizing a toxin, virus, bacterium or allergen, with an antibody, said method comprising administering the composition as described herein to a subject.

In another embodiment, the present disclosure relates to a kit comprising, in one or more separate containers, a polyI:C polynucleotide adjuvant; a lipid-based adjuvant; an amphipathic compound; and a hydrophobic carrier.

Other aspects, embodiments and features of the present disclosure will become apparent to those of ordinary skill in the art upon review of the following description in conjunction with the accompanying claims and figures.

BRIEF DESCRIPTION OF THE FIGURES

In the figures, which illustrate embodiments of the invention by way of example only:

FIG. 1 illustrates the antibody titres and functional activity in response to vaccination with oil-based water-free vaccine containing no adjuvant, polyI:C, Pam3CSK4 (SEQ ID NO: 1) or a combination of polyI:C and Pam3CSK4 (SEQ ID NO: 1). CD-1 mice (n=10) were vaccinated with recombinant PA anthrax antigen formulated in an oil-based water-free vaccine containing no adjuvant (Group 1), polyI:C alone (Group 2), Pam3CSK4 (SEQ ID NO: 1) alone (Group 3) or a combination of polyI:C and Pam3CSK4 (SEQ ID NO: 1) (Group 4). FIG. 1a: Antibody titres were measured in the serum over time using ELISA, statistical analysis by 2-way ANOVA with Bonferroni post-test comparing to Group 1. FIG. 1b: anthrax toxin neutralization acidity of serum was measured on week 8, statistical analysis by 1-way ANOVA with Tukey post-test.

FIG. 3 illustrates the IFN-gamma ELISPOT responses of mice vaccinated with various doses of polyI:C and Pam3CSK4 (SEQ ID NO: 1) adjuvant combination. C57BL6 mice (n=4) were vaccinated with R9F-PADRE antigen in oil-based water-free vaccine formulation containing polyI:C and Pam3CSK4 (SEQ ID NO: 1) adjuvant combination at the following doses: 0.2 micrograms (Group 1), 1.0 microgram (Group 2), 5.0 micrograms (Group 3), 10.0 micrograms (Group 4). IFN-gamma ELISPOT was performed using splenocytes isolated from mice eight days after vaccination, one naïve, non-vaccinated mouse served as a negative control. Responses shown as average SEM. Statistics performed by 1-way ANOVA with Tukey post-test, *p<0.05.

DETAILED DESCRIPTION

Figure 2:
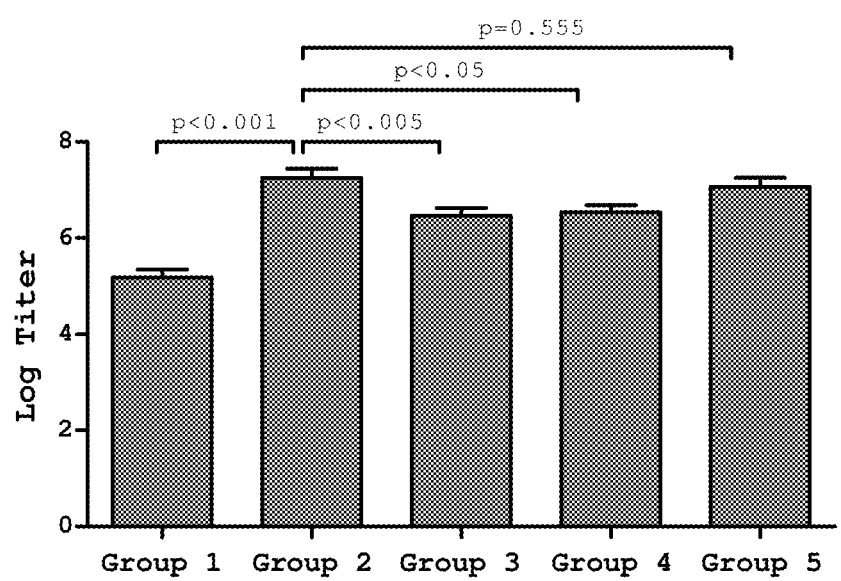
FIG. 2 illustrates the serum antibody responses measured at 12 weeks post immunization. Mice (CD-1) were vaccinated with recombinant HA antigen formulated in an alum adjuvanted vaccine (Group 1), an oil-based water-free vaccine with 1 microgram of each polyI:C and Pam3CSK4 (SEQ ID NO: 1) adjuvant (Group 2), an oil-based water-free formulation with 20 micrograms of each polyI:C and Pam3CSK4 (SEQ ID NO: 1) adjuvant (Group 3), an emulsion with 1 microgram of each polyI:C and Pam3CSK4 (SEQ ID NO: 1) adjuvant (Group 4), or an emulsion with 20 micrograms of each polyI:C and Pam3CSK4 (SEQ ID NO: 1) adjuvant (Group 5). Statistical analysis was performed by student's t-test comparing the indicated groups.

Highly purified and synthetic antigens, such as proteins or peptides, are poorly immunogenic and thus require immune stimulants such as adjuvants to facilitate robust immune responses. There are generally two broad categories of adjuvants: delivery systems and immune-stimulants (Dubensky and Reed 2010, Schijns and Lavelle 2011, Hafner, Corthesy et al. 2013).

Alum adjuvants are the most common in currently licensed human and veterinary vaccines (Gupta 1998, Wilson-Welder, Torres et al. 2009). Alum adjuvants tend to induce a type 2 immune response characterized by IL-4 production, IgG1 and IgE antibodies and eosinophil activation (Wilson-Welder, Torres et al. 2009).

Emulsion-formulation vaccines are an alternative to aluminum-based vaccines. Emulsion formulations form a short-lived depot to facilitate vaccine phagocytosis by innate immune cells and also tend to induce a type 2 immune response (Leenaars, Koedam et al. 1998). Although emulsions have been shown to result in stronger immune responses than alum-adjuvanted vaccines (De Gregorio, Caproni et al. 2013), these formulations have significant limitations (e.g. T cell tolerance, toxicity and reactogenicity) which has precluded their approval for human use (Graham, McElrath et al. 2010).

Immune-stimulator adjuvants can be incorporated into alum or emulsion vaccines with the aim of increasing vaccine immunogenicity and promoting development of type 1 immune responses. Type 1 immune responses are characterized by activity of cytotoxic T lymphocytes and are desirable for certain vaccine indications (Hansen, Met et al. 2012, Gallo 2015). As an example, agonists of toll-like receptors (TLRs) may be used for this purpose (Duthie, Windish et al. 2011).

TLRs are a group of receptors that function as sensors for pathogen-associated molecular patterns (PAMPs). TLRs are found primarily on innate immune cells and TLR signaling to their activation results in unique immune response tailored for the type of pathogen expressing the PAMP (Duthie, Windish et al. 2011). There are 10 TLR proteins that are expressed in humans (Chang 2010). Each TLR is specialized to detect a certain type of PAMP; PAMP agonists include molecules such as double stranded DNA and RNA, flagellin, bacterial lipopeptides, and lipopolysaccharide. These receptors have structural homology, sharing a horseshoe-like extracellular domain of leucine-rich repeats, a single helical transmembrane domain, and an intracellular Toll-interleukin 1 receptor signaling domain (TIR) motif (Watters, Kenny et al. 2007, Song and Lee 2012). Most of the TLRs are found on the cell surface membrane, but a set of intracellular TLRs—3, 7, 8, and 9—are expressed on internal membranes such as endosomes and recognize various forms of nucleic acids (Chang 2010).

TLRs assemble into homodimers upon ligation of respective ligand which initiates downstream signaling cascades (Song and Lee 2012). TLR2 is an exception as it forms a heterodimer with TLR1 or TLR6, and possibly TLR10 in humans (Govindaraj, Manavalan et al. 2010). Each TLR2 heterodimer has different ligand specificity (Takeuchi, Sato et al. 2002). TLRs are the most extensively studied class of receptors as targets for immune-stimulating adjuvants because many of their ligands are known and can be produced synthetically (Duthie, Windish et al. 2011). However, other classes of receptors may be important targets for novel immune-stimulating adjuvants (Pulendran and Ahmed 2006, Ishii and Akira 2007).

TLR agonists can be made synthetically and included in vaccine formulations with the aim of stimulating a specific type of immune response through the stimulation of specific types of immune cells. Some TLR agonists have demonstrated synergistic activity when combined. Some of the most potent combinations are with polyI:C (TLR3 agonist) or LPS (TLR4 agonist), possibly because TLR3 and TLR4 signal using the TRIF adaptor protein while the rest of the TLRs primarily rely on the MyD88 adaptor protein (Napolitani, Rinaldi et al. 2005, Ghosh, Mickelson et al. 2007, Wells, Cowled et al. 2008, Zhu, Egelston et al. 2008, Suet Ting Tan, Lin et al. 2013). However, timing is key as pre-exposure to one TLR agonist may result in tolerance to others (Sato, Nomura et al. 2000, Bagchi, Herrup et al. 2007).

PolyI:C is a synthetic double stranded RNA molecule that activates TLR3. PolyI:C can also stimulate RIG-I and MDA5, non-TLR intracellular receptors that sense nucleic acids and are involved in anti-viral immunity (Kato, Takeuchi et al. 2006). Through these three receptors, polyI:C results in production of type 1 interferon leading to a type 1 immune response (Hafner, Corthesy et al. 2013). In vivo, vaccines adjuvanted with polyI:C can induce potent cytotoxic T cell immune responses (Zhu, Fallert-Junecko et al. 2010, Tsuji, Sabbatini et al. 2013). However, because of the expression of these receptors on a wide variety of cells, use of polyI:C as an adjuvant is limited due to systemic toxicities that may result (Anders, Zecher et al. 2005, Farina, York et al. 2010).

Pam3CSK4 (SEQ ID NO: 1) is a synthetic bacterial tri-acyl lipopeptide that activates the TLR1/2 heterodimer. Pam3CSK4 (SEQ ID NO: 1) is a potent activator of B cells and can stimulate production of class-switched antibodies in vitro (Agrawal and Gupta 2011, Pone, Zhang et al. 2012, Pone, Lou et al. 2015). In vivo, vaccines containing Pam3CSK4 (SEQ ID NO: 1) as an adjuvant can induce potent antibody mediated immunity (Stegmann, Kamphuis et al. 2010, Caproni, Tritto et al. 2012).

Due to their complimentary enhancement of different aspects of the immune system, a combination of polyI:C and Pam3CSK4 (SEQ ID NO: 1) has the potential to be an effective adjuvant system. In this regard, stimulation with the combination of polyI:C and Pam3CSK4 (SEQ ID NO: 1) has been reported to have synergistic activity on macrophages (Bagchi, Herrup et al. 2007) and dendritic cells in vitro (Vanhoutte, Paget et al. 2008). Dendritic cells activated in vitro with polyI:C and Pam3CSK4 (SEQ ID NO: 1) and loaded with antigen could effectively provide protection from tumor growth when adoptively transferred in to tumor bearing mice (Lim, Kuhn et al. 2012). In U.S. Pat. No. 8,216,595 (Moon et al. 2012), polyI:C and Pam3CSK4 (SEQ ID NO: 1) were used as an adjuvant system in an emulsion vaccine, each at a dose of 20 micrograms. The vaccine was administered intramuscularly at a non-disclosed dose volume. However, based on current guidelines for this type of injection in mouse, it is presumed that the dose volume was 50 microliters (Diehl, Hull et al. 2001).

The present disclosure relates to novel adjuvanting systems comprising: (a) a polyI:C polynucleotide adjuvant; (b) a lipid-based adjuvant; (c) an amphipathic compound; and (d) a hydrophobic carrier. The vaccine compositions disclosed herein additionally comprise at least one antigen.

As demonstrated herein, it has now been surprisingly and unexpectedly found that water-free vaccine compositions comprising the adjuvanting system disclosed herein are capable of generating significantly higher antibody titres and more potent cell-mediated immune responses with lower doses of the polyI:C and lipid-based adjuvants.

As used herein, the terms "dose" and "per unit dose" may be used interchangeably. The terms are intended to refer to the total amount or quantity of the vaccine component (e.g. antigen, adjuvant, etc.) given to the subject at each instance of administration.

The ability to raise robust and long lasting antigen-specific antibody immune responses with only one immunization using the components of the composition disclosed herein (Example 1) illustrates the particular usefulness of the adjuvanting systems and compositions in a wide range of medical applications, such as for example those described herein. In water-free vaccine compositions, the adjuvanting system disclosed herein is capable of generating significantly higher antibody titres for extended periods of time as compared to compositions comprising only one of the adjuvants (FIG. 1). Moreover, the antibodies generated using the adjuvanting system disclosed herein have increased functional capacity (FIG. 2).

The data described in Examples 2 and 3 herein are summarized below in Tables 1 and 2.

TABLE 1

| Composition | Antibody titer (log 10) | SEM | Antibody titer (non-logged) |
|---|---|---|---|
| (1) HA antigen<br>Alum Adjuvant<br>PBS Carrier | 5.182 | 0.168 | 260,000 |
| (2) HA antigen<br>PolyI:C (1 µg)<br>Pam3CSK4 (SEQ ID NO: 1) (1 µg)<br>S100 lipids/cholesterol<br>Water-free oil carrier | 7.252 | 0.192 | 29,440,000 |

TABLE 1-continued

| Composition | Antibody titer (log 10) | SEM | Antibody titer (non-logged) |
|---|---|---|---|
| (3) HA antigen<br>PolyI:C (20 μg)<br>Pam3CSK4 (SEQ ID NO: 1) (20 μg)<br>S100 lipids/cholesterol<br>Water-free oil carrier | 6.462 | 0.161 | 4,544,000 |
| (4) HA antigen<br>PolyI:C (1 μg)<br>Pam3CSK4 (SEQ ID NO: 1) (1 μg)<br>Oil Emulsion | 6.537 | 0.144 | 4,096,000 |
| (5) HA antigen<br>PolyI:C (20 μg)<br>Pam3CSK4 (SEQ ID NO: 1) (20 μg)<br>Oil Emulsion | 7.064 | 0.194 | 15,360,000 |

HA antigen = H5N1, A/Vietnam/1203/2004; Protein Sciences, USA
PBS = phosphate buffered saline It will be seen from the above table (Table 1) that vaccine compositions disclosed herein are capable of providing significantly enhanced antibody immune responses, even with a 20-fold lower dose of the adjuvants. The antibody immune response generated with 1 microgram of the polyI:C and Pam3CSK4 (SEQ ID NO: 1) adjuvants in a water-free oil-based composition as disclosed herein (Group 2) was more than 7 times greater than the equivalent dose in an oil emulsion composition (Group 4), and about 2 times greater than an oil emulsion composition comprising 20-fold more (i.e. 20 micrograms) of the polyI:C and Pam3CSK4 (SEQ ID NO: 1) adjuvants (Group 5). Furthermore, the antibody immune response generated by water-free compositions disclosed herein was about 6.5 times greater when a 20-fold lower dose of the adjuvants was used (compare Group 2 and Group 3). These results are surprising and unexpected.

TABLE 2

| Composition | Spot Forming Units (SFU) by ELISPOT |
|---|---|
| (1) R9F antigen<br>PADRE T-helper epitope<br>PolyI:C (0.2 μg)<br>Pam3CSK4 (SEQ ID NO: 1) (0.2 μg)<br>DOPC/cholesterol<br>Water-free oil carrier | 418 ± 13 |
| (2) R9F antigen<br>PADRE T-helper epitope<br>PolyI:C (1 μg)<br>Pam3CSK4 (SEQ ID NO: 1) (1 μg)<br>DOPC/cholesterol<br>Water-free oil carrier | 260 ± 70 |
| (3) R9F antigen<br>PADRE T-helper epitope<br>PolyI:C (5 μg)<br>Pam3CSK4 (SEQ ID NO: 1) (5 μg)<br>DOPC/cholesterol<br>Water-free oil carrier | 247 ± 76 |
| (4) R9F antigen<br>PADRE T-helper epitope<br>PolyI:C (10 μg)<br>Pam3CSK4 (SEQ ID NO: 1) (10 μg)<br>DOPC/cholesterol<br>Water-free oil carrier | 149 ± 25 |

R9F antigen = HPV16E7$_{49-57}$ (RAHYNIVTF; SEQ ID NO: 2)
DOPC = 1,2-Dioleoyl-sn-glycero-3-phosphocholine It will be seen from the above table (Table 2) that water-free vaccine compositions disclosed herein are capable of stimulating potent cell-mediated immune responses. Surprisingly, the compositions are most effective when used at lower doses of the polyI:C and Pam3CSK4 (SEQ ID NO: 1) adjuvants. The vaccine compositions dosed at 1 microgram (Group 2) and 5 micrograms (Group 3) of the polyI:C and Pam3CSK4 (SEQ ID NO: 1) adjuvants were nearly 2 times more effective than the vaccine composition dosed at 10 micrograms of the polyI:C and Pam3CSK4 (SEQ ID NO: 1) adjuvants (Group 4). Decreasing the dose even further to 0.2 micrograms of the polyI:C and Pam3CSK4 (SEQ ID NO: 1) adjuvants (Group 1) resulted in an even more effective cell-mediated immune response, at about 1.5 times the response obtained with the 1 and 5 microgram doses and about 2.8 times the response obtained with the 10 microgram dose. These results are surprising and unexpected.

It is clear from the examples described herein that adjuvanting systems and vaccine compositions disclosed herein are capable of inducing unusually strong antibody and cell-mediated immune responses, and that surprisingly as the dose of adjuvants is increased, the immune response as measured by serum antibodies or IFN-gamma ELISPOT responses decreased.

Adjuvanting System

In an embodiment, disclosed herein is an adjuvanting system for use in a vaccine composition or other pharmaceutical composition. The adjuvanting system comprises: (a) a polyI:C polynucleotide adjuvant; (b) a lipid-based adjuvant; (c) an amphipathic compound; and (d) a hydrophobic carrier.

In some embodiments, the adjuvanting system may be a water-free or substantially water-free formulation that comprises the polyI:C polynucleotide adjuvant; the lipid-based adjuvant; the amphipathic compound; and the hydrophobic carrier. In some embodiments, the adjuvanting system may be a formulation comprising the polyI:C polynucleotide adjuvant; the lipid-based adjuvant; the amphipathic compound; and the hydrophobic carrier, which may optionally be dried by methods known in the art (e.g. freeze-drying, lyophilization, rotary evaporation, evaporation under pressure, etc.) to form a water-free or substantially water-free formulation.

As used herein, the term “adjuvanting system” refers to a combination of components that are together capable of increasing the efficacy of a vaccine composition for inducing or potentiating an antigen-specific immune response to one or more antigens in the vaccine composition, e.g. an antibody immune response and/or a cell-mediated immune response. In a particular embodiment as described herein, the adjuvanting system is used in the preparation of a vaccine composition that is water-free or substantially free of water.

By “increasing the efficacy” of a vaccine composition, it is meant that the adjuvanting system disclosed herein, when used in a vaccine composition, is capable of inducing an enhanced immunogenicity, e.g. an enhanced antibody and/or cell-mediated immune response. The enhanced immune response may, for example, be in comparison to (i) a composition that does not comprise all of the components of the adjuvanting system disclosed herein; (ii) a composition that is not water-free or substantially free of water (e.g. an emulsion); and/or (iii) a composition that contains a higher per unit dose amount of the polyI:C and/or lipid-based adjuvants.

In another embodiment, “increasing the efficacy” of a vaccine composition means that the adjuvanting system disclosed herein, when used in a vaccine composition, is capable of being administered at a lower per unit dose amount while still providing an effective antibody and/or cell-mediated immune response. In an embodiment, the immune response generated by using the lower per unit dose amount of the adjuvants (in a vaccine composition as disclosed herein) is at least equivalent to the immune response immune response generated with a higher per unit dose amount. In other embodiments, the immune response generated by using the lower per unit dose amount of the adjuvants (in a vaccine composition as disclosed herein) is stronger than the immune response immune response generated with a higher per unit dose amount.

As used herein, by "enhanced immunogenicity" or "enhanced immune response", it is meant that the immune response is elevated, improved or strengthened to the benefit of the subject. The enhancement may, for example, be relative to the prior immune response status of the subject (e.g. before the application of a composition as disclosed herein) or be in comparison to the immune response provided by an alternate composition.

PolyI:C Polynucleotide Adjuvants

PolyI:C polynucleotides are polynucleotide molecules (either RNA or DNA or a combination of DNA and RNA) containing inosinic acid residues (I) and cytidylic acid residues (C), and which induce the production of inflammatory cytokines, such as interferon. In some embodiments, the polyI:C polynucleotide is double-stranded. In such embodiments, they are typically composed of one strand consisting entirely of cytosine-containing nucleotides and one strand consisting entirely of inosine-containing nucleotides, although other configurations are possible. For instance, each strand may contain both cytosine-containing and inosine-containing nucleotides. In some instances, either or both strand may additionally contain one or more non-cytosine or non-inosine nucleotides.

In another embodiment, the polyI:C polynucleotide may be a single-stranded molecule containing inosinic acid residues (I) and cytidylic acid residues (C). As an example, and without limitation, the single-stranded polyI:C may be a sequence of repeating dIdC. In a particular embodiment, the sequence of the single-stranded polyI:C may be a 26-mer sequence of $(IC)_{13}$, i.e. ICICICICICICICICICICICIC (SEQ ID NO: 3). As the skilled person will appreciate, due to their nature (e.g. complementarity), it is anticipated that these single-stranded molecules of repeating dIdC would naturally form homodimers, so they are conceptually similar to polyI/polyC dimers.

It has been reported that polyI:C can be segmented every 16 residues without an effect on its interferon activating potential (Bobst, 1981). Furthermore, the interferon inducing potential of a polyI:C molecule mismatched by introducing a uridine residue every 12 repeating cytidylic acid residues (Hendrix, 1993), suggests that a minimal double stranded polyI:C molecule of 12 residues is sufficient to promote interferon production. Others have also suggested that regions as small as 6-12 residues, which correspond to 0.5-1 helical turn of the double stranded polynucleotide, are capable of triggering the induction process (Greene, 1978). If synthetically made, polyI:C polynucleotides are typically about 20 or more residues in length (commonly 22, 24, 26, 28 or 30 residues in length). If semi-synthetically made (e.g. using an enzyme), the length of the strand may be 500, 1000 or more residues.

PolyI:C acts as a mimic of viral genomes and is particularly useful for modulating the immune system in vivo. Synthetic poly I:poly C homopolymers for example have been reported to enhance innate immunity by inducing interferon gamma non-specifically when delivered systemically in vivo by intravenous or intramuscular injection (Krown 1985, Zhu 2007). Several variants of poly inosinic and cytidylic acid polymers have been described over the years (de Clercq 1978, Bobst 1981, de Clercq 1975, Guschlbauer 1977, Fukui 1977, Johnston 1975, U.S. Pat. No. 3,906,092, Kamath 2008, Ichinohe 2007), some of which included the use of covalently modified residues, the use of ribo and deoxy-ribo inosinic and cytidylic residues, the use of homopolymers and alternating co-polymers that contain inosinic and cytidylic acid residues, and the introduction of specific residues to create mismatched polymers.

The use of double stranded polynucleotides containing inosinic and cytidylic acids has been reported for the treatment of a number of viral diseases (Kende 1987, Poast 2002, U.S. Pat. No. 6,468,558, Sarma 1969, Stephen 1977, Levy 1978), cancer (Durie 1985, Salazar 1996, Theriault 1986, Nakamura 1982, Talmadge 1985, Droller 1987), autoimmune disease like multiple sclerosis (Bever 1986), and other infectious diseases such as malaria (Awasthi 1997, Puri 1996). The efficacy of polyI:C molecules has been further enhanced in some cases by complexing the molecule with positively charged poly-lysine and carboxymethyl-cellulose, effectively protecting the polynucleotide from nuclease degradation in vivo (Stephen 1977, Levy 1985), or by complexing polyI:C with positively charged synthetic peptides (Schellack 2006).

In addition to its use as a non-specific enhancer of innate immunity, polyI:C is also useful as an adjuvant in vaccine compositions. The enhancement of innate immunity can lead to an enhanced antigen specific adaptive immunity, possibly through a mechanism that involves, at least in part, NK cells, macrophages and/or dendritic cells (Chirigos 1985, Salem 2006, Alexopoulou 2001, Trumpfheller 2008). Evidence for the use of polyI:C molecules in this context originates from various vaccine studies for controlling infectious diseases (Houston 1976, Stephen 1977, Ichinohe 2007, Sloat 2008, Agger 2006, Padalko 2004) and the prevention or treatment of cancer by a variety of vaccine modalities (Zhu 2007, Cui 2006, Salem 2005, Fujimura 2006, Llopiz 2008). These studies demonstrate that polyI:C enhances humoral responses as evident from enhanced antibody responses against specific infectious disease antigens. PolyI:C is also a potentiator of antigen-specific cellular responses (Zhu 2007, Zaks 2006, Cui 2006, Riedl 2008). The adjuvanting effects of polyI:C molecules are believed to occur, at least partially, by inducing interferon-gamma through their interaction with toll like receptors (TLR) such as TLR3, TLR4, TLR7, TLR8 and TLR9 (Alexopoulou 2001, Trumpfheller 2008, Schellack 2006, Riedl 2008), with TLR3 being particularly relevant for most polyI:C molecules. Evidence also suggests that polyI:C molecules may exert their effect, at least in part, by interacting with receptors other than TLRs, such as the RNA helicase retinoic acid induced protein I (RIG-I)/melanoma differentiation associated gene 5 (MDA5) (Alexopoulou 2001, Yoneyama 2004, Gowen 2007, Dong 2008). The mechanism of action of polyI:C molecules remains to be fully understood.

Accordingly, as used herein, a "polyI:C", "polyI:C polynucleotide" or "polyI:C polynucleotide adjuvant" is a double- or single-stranded polynucleotide molecule (RNA or DNA or a combination of DNA and RNA), each strand of which contains at least 6 contiguous inosinic or cytidylic acid residues, or 6 contiguous residues selected from inosinic acid and cytidylic acid in any order (e.g. IICIIC (SEQ ID NO: 4) or ICICIC (SEQ ID NO: 5)), and which is capable of inducing or enhancing the production of at least one inflammatory cytokine, such as interferon, in a mammalian subject. PolyI:C polynucleotides will typically have a length of about 8, 10, 12, 14, 16, 18, 20, 22, 24, 25, 26, 28, 30, 35, 40, 45, 50, 55, 60, 65, 70, 75, 80, 85, 90, 95, 100, 150, 200, 250, 300, 500, 1000 or more residues. Preferred polyI:C polynucleotides may have a minimum length of about 6, 8, 10, 12, 14, 16, 18, 20, 22, 24, 26, 28, or 30 nucleotides and a maximum length of about 1000, 500, 300, 200, 100, 90, 80, 70, 60, 50, 45 or 40 nucleotides.

Each strand of a double-stranded polyI:C polynucleotide may be a homopolymer of inosinic or cytidylic acid residues, or each strand may be a heteropolymer containing both inosinic and cytidylic acid residues. In either case, the polymer may be interrupted by one or more non-inosinic or non-cytidylic acid residues (e.g. uridine), provided there is at least one contiguous region of 6 I, 6 C or 6 I/C residues as described above. Typically, each strand of a polyI:C polynucleotide will contain no more than 1 non-I/C residue per 6 I/C residues, more preferably, no more than 1 non-I/C residue per every 8, 10, 12, 14, 16, 18, 20, 22, 24, 26, 28 or 30 I/C residues.

The inosinic acid or cytidylic acid (or other) residues in the polyI:C polynucleotide may be derivatized or modified as is known in the art, provided the ability of the polyI:C polynucleotide to promote the production of an inflammatory cytokine, such as interferon, is retained. Non-limiting examples of derivatives or modifications include e.g. azido modifications, fluoro modifications, or the use of thioester (or similar) linkages instead of natural phosphodiester linkages to enhance stability in vivo. The polyI:C polynucleotide may also be modified to e.g. enhance its resistance to degradation in vivo by e.g. complexing the molecule with positively charged poly-lysine and carboxymethylcellulose, or with a positively charged synthetic peptide.

In some embodiments, the polyI:C polynucleotide adjuvant is a traditional form of polyI:C with an approximate molecular weight of 989,486 Daltons, containing a mixture of varying strand lengths of polyI and polyC of several hundred base pairs (Thermo Scientific; USA).

Determination of an appropriate per unit dose of the polyI:C polynucleotide is well within the capability of those skilled in the art, especially in light of the disclosure provided herein. In some embodiments, the per unit dose will be a low dose amount of the polyI:C polynucleotide adjuvant as compared to what is conventional. As disclosed herein, the adjuvanting system is capable of generating strong immune responses with low per unit dose amounts of the adjuvants. In an embodiment, the low dose amount of the polyI:C polynucleotide adjuvant is less than 10, 9, 8, 7, 6, 5, 4, 3, 2, 1 or 0.5 micrograms per unit dose of the composition as calculated in mice, or an equivalent translated per unit dose for humans. In a particular embodiment, the low dose amount of the polyI:C polynucleotide adjuvant is about 0.2, 0.3, 0.4, 0.5, 1, 1.5, 2, 2.5, 3, 3.5, 4, 4.5 or 5 micrograms per unit dose as calculated in mice, or an equivalent translated dose for humans. A typical dose volume in mice is, for example, 50 microliters. Without limitation, a typical dose volume in humans may be between 50-500 microliters. Thus, in some embodiments, the translated low dose amount in humans will be between 2-50 micrograms, for example about 2, 3, 4, 5, 10, 15, 20, 25, 30, 35, 40, 40 or 50 micrograms per unit dose.

Lipid-Based Adjuvants

As used herein, a lipid-based adjuvant is an adjuvant that comprises at least one lipid moiety or lipid component.

The expression "lipid moiety" or "lipid component" refers to any fatty acid (e.g. fatty acyls) or derivative thereof, including for example triglycerides, diglycerides, and monoglycerides. Exemplary fatty acids include, without limitation, palmitoyl, myristoyl, stearoyl and decanoyl groups or any C2 to C30 saturated or unsaturated fatty acyl group, preferably any C14 to C22 saturated or unsaturated fatty acyl group, and more preferably a C16 saturated or unsaturated fatty acyl group. Thus, as referred to herein, the expression "lipid-based adjuvant" encompasses adjuvants comprising a fatty acyl group or derivative thereof.

Lipid-based adjuvants contain at a minimum at least one lipid moiety, or a synthetic/semi-synthetic lipid moiety analogue, which can be coupled onto an amino acid, an oligopeptide or other molecules (e.g. a carbohydrate, a glycan, a polysaccharide, biotin, Rhodamine, etc.). Thus, without limitation, the lipid-based adjuvant may be, for example, a lipoamino acid, a lipopeptide, a lipoglycan, a lipopolysaccharide or a lipoteichoic acid. Moreover, a lipid moiety or a structure containing a lipid moiety can be coupled covalently or non-covalently to an antigen to create antigenic compounds with built-in adjuvanting properties. For example, and without limitation, the lipid-based moiety may comprise a cation (e.g. nickel) to provide a positive charge for non-covalent coupling. In some embodiments, the lipid moiety or structure containing the lipid moiety may be coupled to an antigen by co-encapsulation in a particle, including without limitation liposomes, PGLA nanoparticles, dendrimers or any other suitable particle with the purpose of bringing or keeping the lipid moiety in close proximity to an antigen so they can be co-delivered efficiently.

In some embodiments, the lipid moiety or lipid component may be naturally occurring, such as for example a cell-wall component (e.g. lipoprotein) from a Gram-positive or Gram-negative bacteria, *Rhodopseudomonas viridis*, or *mycoplasma*. In other embodiments, the lipid moiety or lipid component may be synthetic or semi-synthetic.

The lipid-based adjuvant may comprise palmitic acid (PAM) as at least one of the lipid moieties or components of the adjuvant. Such lipid-based adjuvants are referred to herein as a "palmitic acid adjuvant". Palmitic acid is a low molecular weight lipid found in the immunologically reactive Braun's lipoprotein of *Escherichia coli*. Other common chemical names for palmitic acid include, for example, hexadecanoic acid in IUPAC nomenclature and 1-Pentadecanecarboxylic acid. The molecular formula of palmitic acid is $CH_3(CH_2)_{14}CO_2H$. As will be understood to those skilled in the art, it is possible that the lipid chain of palmitic acid may be altered. Exemplary compounds which may be used herein as palmitic acid adjuvants, and methods for their synthesis, are described for example in United States Patent Publications US 2008/0233143; US 2010/0129385; and US 2011/0200632, the disclosures of which are incorporated herein.

As described above for lipid moieties generally, a palmitic acid adjuvant contains at a minimum at least one palmitic acid moiety, which can be coupled onto an amino acid, an oligopeptide or other molecules. A palmitic acid moiety or a structure containing palmitic acid can be coupled covalently or non-covalently to an antigen to create antigenic compounds with built-in adjuvanting properties. The palmitic acid moiety or a chemical structure containing palmitic acid can be conjugated to a cysteine peptide (Cys) to allow for various structural configurations of the adjuvant, including linear and branched structures. The cysteine residue has been commonly extended by polar residues such as Serine (Ser) and/or lysine (Lys) at the C terminus to create adjuvant compounds with improved solubility. Palmitic acid containing adjuvant compounds could be admixed with an antigen, associated with antigen through non-covalent interactions, or alternatively covalently linked to an antigen, either directly or with the use of a linker/spacer, to generate enhanced immune responses. Most commonly, two palmitic acid moieties are attached to a glyceryl backbone and a cysteine residue to create dipalmitoyl-S-glyceryl-cysteine (PAM$_2$Cys) or tripalmitoyl-S-glyceryl-cysteine (PAM$_3$Cys), which can also be used in multiple configurations as described above.

Palmitic acid adjuvants are known to activate B cells causing rapid proliferation and production of antibodies. B cells that recognize the antigen co-delivered with the adjuvant in the vaccine formulation and through affinity maturation will proliferate with increasing specificity towards the antigen. Activated B cells are known to secrete large quantities of soluble immunoglobin antibodies that can bind to soluble targets, such as bacteria, present in the blood. Antibody effector functions are i) opsonization; ii) antibody-dependent cell-mediated cytotoxicity (ADCC); iii) complement activation; iv) neutralization. While the majority of the B cells will mature into antibody secreting plasma cells, a portion should differentiate into memory B cells that persist after the immune response has controlled infection. This provides long-term immunity against subsequent exposure to the pathogen. Ideally, a prophylactic vaccine should induce a strong memory B cell population.

Therefore, in an embodiment, the lipid-based adjuvant is any type of adjuvant comprising a palmitic acid moiety or component. In an embodiment, lipid-based adjuvant is a lipopeptide comprising one or more palmitic acid moieties. The palmitic acid moiety may be modified or manipulated to improve its stability in vitro or in vivo, enhance its binding to receptors (such as for example toll-like receptors as described below) or enhance its biological activity.

In a particular embodiment, the palmitic acid adjuvant may comprise PAM$_2$Cys.

In another particular embodiment, the palmitic acid adjuvant may comprise PAM$_3$Cys.

In another particular embodiment, the palmitic acid adjuvant may be Pam-2-Cys-Ser-(Lys)4 (SEQ ID NO: 1) or Pam-3-Cys-Ser-(Lys)4 (SEQ ID NO: 1). Such palmitic acid adjuvants are available, for example, as research reagents from EMC Microcollections GmbH (Germany) and InvivoGen (San Diego, Calif., USA).

Also available from EMC Microcollections are various analogs of Pam-2-Cys-Ser-(Lys)4 (SEQ ID NO: 1) and Pam-3-Cys-Ser-(Lys)4 (SEQ ID NO: 1), including labelled analogs. These analogs are encompassed herein and include, without limitation, PAM$_3$Cys-SKKKK (SEQ ID NO: 1) (β-irradiated), R-PAM$_3$Cys-SKKKK (SEQ ID NO: 1), S-PAM$_3$Cys-SKKKK (SEQ ID NO: 1), PAM$_3$Cys-SKKKK (Biotin-Aca-Aca) (SEQ ID NO: 1), PAM$_3$Cys-SKKKK (Fluorescein-Aca-Aca) (SEQ ID NO: 1), PAM$_3$Cys-SKKKK(Rhodamine-Aca-Aca) (SEQ ID NO: 1), PAM$_3$Cys-SKKKK-FLAG-tag (SEQ ID NO: 1), PAM$_3$Cys-SSNAKIDQLSSDVQT (SEQ ID NO: 6), PAM$_3$Cys-SSNK-STTGSGETTTA (SEQ ID NO: 7), PAM$_3$Cys-SSTKPVSQDTSPKPA (SEQ ID NO: 8), PAM$_3$Cys-SSGSKPSGGPLPDAK (SEQ ID NO: 9), PAM$_3$Cys-SSGNKSAPSSSASSS SEQ ID NO: 10), PAM$_3$Cys-GSHQMKSEGHANMQL (SEQ ID NO: 11), PAM$_3$Cys-SSSNNDAAGNGAAQT (SEQ ID NO: 12), PAM$_3$Cys-KQNVSSLDEKNSVSV (SEQ ID NO: 13), PAM$_3$Cys-NNSGKDGNTSANSAD SEQ ID NO: 14), PAM$_3$Cys-NNGGPELKSDEVAKS (SEQ ID NO: 15), PAM$_3$Cys-SQEPAAPAAEATPAG (SEQ ID NO: 16), PAM$_3$Cys-SSSKSSDSSAPKAYG (SEQ ID NO: 17), PAM$_3$Cys-AQEKEAKSELDYDQT (SEQ ID NO: 18), Pam2Cys-SKKKK (mixture of RR and RS stereoisomers) (SEQ ID NO: 1), R-Pam$_2$Cys-SKKKK (RR stereoisomer) (SEQ ID NO: 1), S-Pam$_2$Cys-SKKKK (RS stereoisomer) (SEQ ID NO: 1), PamCys(Pam)-SKKKK (SEQ ID NO: 19), Pam$_2$Cys-SKKKK(Biotin-Aca-Aca)-NH$_2$(SEQ ID NO: 1), Pam$_2$Cys-SKKKK(Fluorescein-Aca-Aca)-NH$_2$ (SEQ ID NO: 1), PAM$_2$Cys-SKKKK(Rhodamine-Aca-Aca)-NH$_2$ (SEQ ID NO: 1), and PAM$_2$Cys-SKKKK-FLAG-tag (SEQ ID NO: 1). Where appropriate, the palmitic acid adjuvant or analog thereof may used as stereochemically defined compounds or as a mixture of stereoisomers.

In a particular embodiment, the lipid-based adjuvant of the adjuvanting system and compositions disclosed herein is Pam-3-Cys-Ser-(Lys)4 (SEQ ID NO: 1):

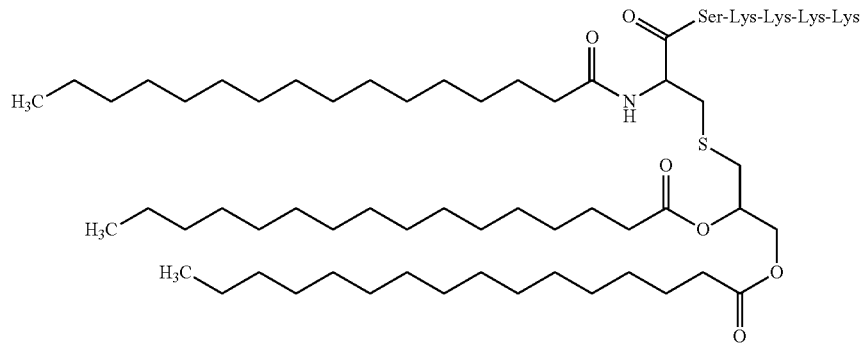

In some embodiments, the lipid-based adjuvant is one that activates or increases the activity of toll-like receptors (TLRs), and preferably activates or increases the activity of TLR2. As used herein, activating or increasing the activity of TLR2 may encompass its activation in any monomeric, homodimeric or heterodimeric form, and particularly the activation of TLR2 as a heterodimer with TLR1 or TLR6 (i.e. TLR1/2 or TLR2/6), as described in further detail below.

TLRs are a conserved family of transmembrane spanning receptors found primarily on leukocytes such as dendritic cells (DCs) and macrophages, professional antigen presenting cells. TLRs have specifically evolved to recognize and induce an immune response to pathogen associated molecular patterns, such as for example bacterial lipoproteins and lipopeptides and viral double stranded RNA. More than 10 distinct TLRs have been identified in mice and humans, although the ligand and signalling pathways are not yet known for some (see Table 3 below). There are 13 identified TLRs in humans, numbered 1 through 13.

TABLE 3

| Receptor | Type of Agonist | Adaptor Molecule | Cellular Location | Agonist Examples |
|---|---|---|---|---|
| TLR1/2 | Bacterial lipopeptides | MyD88 | Surface | Pam3Cys |
| TLR3 | dsRNA | TRIF | Intracellular | PolyI:C |
| TLR4 | Lipopolysaccharide | MyD88/TRIF | Surface | LPS, MPL |
| TLR5 | Protein | MyD88 | Surface | Flagellin |
| TLR2/6 | Bacterial diacyl lipopeptides | MyD88 | Surface | Zymosan, Pam2Cys |
| TLR7 | ssRNA | MyD88 | Intracellular | Imiquimod, Loxoribine |
| TLR8 | ssRNA, small synthetic compounds | MyD88 | Intracellular | Resiquimod, R848 |
| TLR9 | Unmethlyated DNA | MyD88 | Intracellular | CpG |

TLRs typically form homodimers, with the exception of TLR2 which forms a heterodimer with TLR1 or TLR6 resulting in differing ligand specificity. TLR2 mediates downstream signalling, so these heterodimers are often referred to collectively as TLR2 (Takeuchi 2010). Stimulation of the TLRs on DCs results in upregulation of MHC and co-stimulatory molecules, which enhance the antigen presenting function of these cells, as well as the production of Th1-type cytokines and promotion of cross-presentation (Lahiri 2008; Welters 2007; Matsumoto 2008; Blander 2008). Because stimulation through TLRs has a direct effect on boosting the immune response, TLR agonists have been studied as potential adjuvants (Barchet 2008).

TLRs have a conserved cytosolic domain termed the Toll-interleukin 1 receptor (TIR) which is associated with an adaptor molecule that facilitates downstream signalling pathways leading to cellular activation. TLRs could be broadly categorized by the adaptor protein they are associated with, MyD88 or TRIF. TLR4 alone can signal through both pathways. Both signalling pathways converge on the activation of the transcription factor NF-KB (Ouyang 2007). Several studies have demonstrated that although different TLRs share some downstream signalling molecules, each receptor produces a unique profile of pro-inflammatory mediators (Welters 2007; Seya 2006; Ghosh 2006; Re 2004; Avril 2009). The full downstream pathway for TLR receptors are not fully elucidated, but differences in activation could be the result of the strength of the ligand, subcellular location of the receptor, cell type and the presence of interferon regulatory factors (IRF).

Palmitic acid adjuvants have been reported to signal through toll-like receptor 2 (TLR2). For example, PAM$_2$Cys is recognized by the heterodimer TLR2 and TLR6. Also as an example, PAM$_3$Cys, which is recognized by the heterodimer TLR1 and TLR2, triggers an anti-bacterial response typified by humoral activity. In contrast double stranded RNA from viruses is recognized by TLR3 and induces an anti-viral response that is usually characterized by interferon release and T cell activity. Mediating cellular responses has been associated with TLR2.

Pam$_3$Cys has been tested in a variety of animal models and in Phase I clinical trial in humans with no reported side effects (Moyle 2008; Wiedemann 1991). In a screen of TLR agonists on murine DCs, stimulation with Pam$_3$Cys in vitro produced high levels of the pro-inflammatory cytokines IL-12p40, IL-6 and TNFα that was attained with only small amounts of the adjuvant relative to other TLR agonists tested (Welters 2007).

In some embodiments, the lipid-based adjuvant of the adjuvanting system disclosed herein activates or increases the activity of a TLR, or acts as an agonist to a TLR. In a particular embodiment, the lipid-based adjuvant activates or increases the activity of TLR2. Without limitation, such lipid-based adjuvants may be a palmitic acid adjuvant which activates or increases the activity of a TLR, such as a palmitic acid adjuvant comprising PAM$_2$Cys or PAM$_3$Cys (e.g. Pam-2-Cys-Ser-(Lys)4 (SEQ ID NO: 1) or Pam-3-Cys-Ser-(Lys)4 (SEQ ID NO: 1)).

Other synthetic palmitic acid-based lipoproteins that act as TLR agonists may also be used in the adjuvanting system disclosed herein, including without limitation the palmitic acid adjuvants and analogs described above and synthetic diacylated lipoprotein FSL-1 available from InvivoGen (San Diego, Calif., USA) and EMC Microcollections GmbH (Germany). FSL-1 (Pam$_2$CGDPKHPKSF; SEQ ID NO: 20) is a synthetic lipoprotein that represents the N-terminal part of the 44-kDa lipoprotein LP44 of Mycoplasma salivarium. FSL-1 comprises PAM$_2$Cys and has a similar framework structure as macrophage activating lipopeptide-2 (MALP-2), a Mycoplasma fermentans derived lipopeptide. It is postulated that FSL-1 and MALP-2, containing a lipolyated N-terminal diacylated cysteine residue, are recognized by dimer TLR2 and TLR6 9TLR2/6). Synthetic MALP-2 is available from Enzo Life Sciences (Farmingdale, N.Y., USA).

In an embodiment, the lipid-based adjuvant comprises FSL-1 or MALP-2, or the lipid-based adjuvant is FSL-1 or MALP-2. Where appropriate, FSL-1 or MALP-2 may be used as stereochemically defined compounds or as a mixture of stereoisomers. The FSL-1 or MALP-2 may be labelled (e.g. biotin, Fluorescein, Rhodamine, etc.). FSL-1 is also available as a FSL-1 Ala-scan collection (EMC Microcollections) comprising nine different FSL-1-Ala compounds. Each of these FSL-1-Ala molecules is encompassed herein individually or in combination.

Further embodiments of lipid-based adjuvants that comprise palmitic acid may include substructures of TLR2 ligands such as monoacylated lipopeptides. Without limitation, these may include, for example, Pam-Dhc-SKKKK (SEQ ID NO: 19), Pam-CSKKKK (SEQ ID NO: 1), Pam-Dhc-GDPKHPKSF (SEQ ID NO: 21) or Pam-CGDPKHPKSF (SEQ ID NO: 20; EMC Microcollections).

Determination of an appropriate per unit dose of the lipid-based adjuvant is well within the capability of those skilled in the art, especially in light of the disclosure provided herein. In some embodiments, the per unit dose will be a low dose amount of the lipid-based adjuvant as compared to what is conventional. As disclosed herein, the adjuvanting system is capable of generating strong immune responses with low dose amounts of the adjuvants. In an embodiment, the low dose amount of the lipid-based adjuvant is less than 10, 9, 8, 7, 6, 5, 4, 3, 2, 1 or 0.5 micrograms per unit dose of the composition as calculated in mice, or an equivalent translated per unit dose for humans. In a particular embodiment, the low dose amount of the lipid-based adjuvant is about 0.2, 0.3, 0.4, 0.5, 1, 1.5, 2, 2.5, 3, 3.5, 4, 4.5 or 5 micrograms per unit dose as calculated in mice, or an equivalent translated dose for humans. A typical dose volume in mice is, for example, 50 microliters. Without limitation, a typical dose volume in humans may be between 50-500 microliters. Thus, in some embodiments, the translated low dose amount in humans will be between 2-50 micrograms, for example about 2, 3, 4, 5, 10, 15, 20, 25, 30, 35, 40, 40 or 50 micrograms per unit dose.

Amphipathic Compound

An "amphipathic compound" is a compound having both hydrophilic and hydrophobic (lipophilic) parts or characteristics. The term "amphipathic compound" may be used interchangeably with "amphiphile" or "amphiphilic". In some embodiments, suitable amphipathic compounds may also include emulsifiers such as those described herein below. Exemplary embodiments of emulsifiers that are encompassed herein by the term "amphipathic compound" include, without limitation, polysorbates (e.g. sorbitan monooleate), mannide oleate (Arlacel™ A), lecithin, Tween™ 80, and Spans™ 20, 80, 83 and 85. The amphipathic compound can facilitate the incorporation of vaccine components with hydrophilic affinity into a hydrophobic carrier such as an oil in the absence of water. The vaccine components can include, without limitation, antigens and/or adjuvants and/or other ingredients (e.g. T-helper epitopes) that can facilitate the production of an immune response.

Without limitation, the hydrophobic portion of an amphipathic compound is typically a large hydrocarbon moiety, such as a long chain of the form $CH_3(CH_2)_n$, with n>4. The hydrophilic portion of an amphipathic compound is usually either a charged group or a polar uncharged group. Charged groups include anionic and cationic groups. Examples of anionic charged groups include the following (wherein the hydrophobic part of the molecule is represented by "R"): carboxylates: $RCO_2^-$; sulfates: $RSO_4^-$; sulfonates: $RSO_3^-$; and phosphates (the charged functionality in phospholipids). Cationic charged groups include e.g. amines: $RNH_3^+$ ("R" again representing the hydrophobic part of the molecule). Uncharged polar groups include e.g. alcohols with large R groups, such as diacyl glycerol (DAG). Amphipathic compounds may have several hydrophobic parts, several hydrophilic parts, or several of both. Proteins and some block copolymers are examples. Steroids, cholesterol, fatty acids, bile acids, and saponins, are also amphiphiles.

There are numerous amphipathic compounds which may be used, and the adjuvanting system and vaccine compositions disclosed herein may contain a single type of amphipathic compound or a mixture of different types of amphipathic compounds.

In an embodiment, the amphipathic compound is a lipid. Although any amphiphilic lipid may be used, particularly suitable lipids may include those with at least one fatty acid chain containing at least 4 carbons, and typically about 4 to 28 carbons in length. The fatty acid chain may contain any number of saturated and/or unsaturated bonds. The lipid may be a natural lipid or a synthetic lipid. Non-limiting examples of amphiphilic lipids may include phospholipids, sphingolipids, sphingomyelin, cerobrocides, gangliosides, ether lipids, sterols, cardiolipin, cationic lipids and lipids modified with poly (ethylene glycol) and other polymers. Synthetic lipids may include, without limitation, the following fatty acid constituents: lauroyl, myristoyl, palmitoyl, stearoyl, arachidoyl, oleoyl, linoleoyl, erucoyl, or combinations of these fatty acids.

In an embodiment, the amphipathic compound is a phospholipid or a mixture of phospholipids. Broadly defined, a "phospholipid" is a member of a group of lipid compounds that yield on hydrolysis phosphoric acid, an alcohol, fatty acid, and nitrogenous base.

Phospholipids that may be used include for example, and without limitation, those with at least one head group selected from the group consisting of phosphoglycerol, phosphoethanolamine, phosphoserine, phosphocholine (e.g. DOPC; 1,2-Dioleoyl-sn-glycero-3-phosphocholine) and phosphoinositol. In some embodiments, a mixture of DOPC and unesterified cholesterol may be used. In other embodiments, a mixture of Lipoid S100 lecithin and unesterified cholesterol may be used. When unesterified cholesterol is used, the cholesterol may be used in an amount equivalent to about 10% of the weight of phospholipid (e.g. in a DOPC:cholesterol ratio of 10:1 w/w or a S100 lecitin: cholesterol ratio of 10:1 w/w). The cholesterol is used to stabilize the formation of phospholipid vesicles. If a compound other than cholesterol is used, one skilled in the art can readily determine the amount needed.

Another common phospholipid is sphingomyelin. Sphingomyelin contains sphingosine, an amino alcohol with a long unsaturated hydrocarbon chain. A fatty acyl side chain is linked to the amino group of sphingosine by an amide bond, to form ceramide. The hydroxyl group of sphingosine is esterified to phosphocholine. Like phosphoglycerides, sphingomyelin is amphipathic.

Lecithin, which also may be used, is a natural mixture of phospholipids typically derived from chicken eggs or sheep's wool.

All of these and other phospholipids may be used in the practice of the invention. Phospholipids can be purchased, for example, from Avanti lipids (Alabastar, Ala., USA), and lipoid LLC (Newark, N.J., USA).

In an embodiment, the amphipathic compound may be substantially evenly dispersed in the hydrophobic carrier, whereby the presence of the amphipathic compound alone is sufficient to facilitate the incorporation of vaccine components with hydrophilic affinity (e.g. an antigen) into a hydrophobic carrier.

In another embodiment, the amphipathic compound may be closely associated with the antigen so as to make the antigen miscible in the hydrophobic carrier. By "closely associated", it is meant that the amphipathic compound is in such proximity with the antigen that the antigen is presented in a form that it is miscible in the hydrophobic carrier. The close association may or may not involve physical interaction between the antigen and the amphiphile. Typically, the hydrophilic part of the amphipathic compound is oriented towards the hydrophilic moieties on the antigen. The amphipathic compounds may remain substantially separate from one another or they may form various different types of structures, assemblies or arrays.

Exemplary embodiments of the types of structures, assemblies or arrays that the amphipathic compounds may form include, without limitation: single layer sheets, bilayer sheets, multilayer sheets, single layer vesicular structures (e.g. micelles), bilayer vesicular structures (e.g. unilamellar or multilamellar vesicles), or various combinations thereof. By "single layer" it is meant that the amphipathic compounds do not form a bilayer, but rather remain in a layer with the hydrophobic part oriented on one side and the hydrophilic part oriented on the opposition side. By "bilayer" it is meant that the amphipathic compounds form a two-layered sheet, typically with the hydrophobic part of each layer internally oriented toward the center of the bilayer with the hydrophilic part externally oriented. However, the opposite configuration is also possible. The term "multilayer" is meant to encompass any combination of single and bilayer structures. The form adopted may depend upon the specific antigen, the specific amphipathic compound, and/or the specific hydrophobic carrier that is used.

In an embodiment, the structure, assembly or array formed by the amphipathic compound may partially or completely surround the antigen. As an example, the amphipathic compound may form a closed vesicular structure around the antigen.

In an embodiment, the vesicular structure is a single layer vesicular structure. An example of such a structure is a micelle. A typical micelle in aqueous solution forms an aggregate with the hydrophilic parts in contact with the surrounding aqueous solution, sequestering the hydrophobic parts in the micelle center. In contrast, in a hydrophobic carrier, an inverse/reverse micelle forms with the hydrophobic parts in contact with the surrounding aqueous solution, sequestering the hydrophilic parts in the micelle center. A spherical reverse micelle can package an antigen with hydrophilic affinity within its core.

In an embodiment, the vesicular structure is a micelle or an inverse/reverse micelle. Without limitation, the size of the micelles or inverse/reverse micelles range from 2 nm (20 Å) to 20 nm (200 Å) in diameter. In a particular embodiment, the size of the micelles or inverse/reverse micelles is about 10 nm in diameter.

In another embodiment, the vesicular structure is a bilayer vesicular structure, such as for example, a liposome. Liposomes are completely closed lipid bilayer membranes containing an entrapped aqueous volume. Liposomes may be unilamellar vesicles (possessing a single bilayer membrane) or multilamellar vesicles characterized by multimembrane bilayers, each bilayer may or may not be separated from the next by an aqueous layer. A general discussion of liposomes can be found in Gregoriadis G. *Immunol. Today*, 11:89-97, 1990; and Frezard, F., *Braz. J. Med. Bio. Res.*, 32:181-189, 1999. Liposomes can adsorb to virtually any type of cell and then release an incorporated agent (e.g. antigen). Alternatively, the liposome can fuse with the target cell, whereby the contents of the liposome empty into the target cell. Alternatively, a liposome may be endocytosed by cells that are phagocytic.

Liposomes have been used in the preparation of compositions comprising a hydrophobic carrier as a vesicle to encapsulate antigens as well as an emulsifier to stabilize the formulation (see e.g. WO2002/038175, WO2007/041832, WO2009/039628, WO2009/146523 and WO2013/049941. Hydrophilic antigens are typically entrapped in the aqueous interior, while hydrophobic antigens can be intercalated in the lipid bilayer or dispersed in the oil phase.

Other embodiments of bilayer and mutilayer vesicular structures include, without limitation: niosomes, transfersomes, virosomes, multilamellar vesicles (MLV), oligolamellar vesicles (OLV), unilamellar vesicles (UV), small unilamellar vesicles (SUV), medium-sized unilamellar vesicles (MUV), large unilamellar vesicles (LUV), giant unilamellar vesicles (GUV), multivesicular vesicles (MVV), single or oligolamellar vesicles made by reverse-phase evaporation method (REV), multilamellar vesicles made by the reverse-phase evaporation method (MLV-REV), stable plurilamellar vesicles (SPLV), frozen and thawed MLV (FATMLV), vesicles prepared by extrusion methods (VET), vesicles prepared by French press (FPV), vesicles prepared by fusion (FUV), dehydration-rehydration vesicles (DRV), and bubblesomes (BSV). The skilled artisan will recognize that the techniques for preparing these vesicular structures are well known in the art (see e.g. Kreuter, J., ed., Colloidal Drug Delivery Systems, vol. 66, Marcel Dekker, Inc., 1994).

Hydrophobic Carrier

The adjuvanting system and compositions disclosed herein comprise a hydrophobic carrier, preferably a liquid hydrophobic substance.

The hydrophobic carrier may be an essentially pure hydrophobic substance or a mixture of hydrophobic substances. Hydrophobic substances that are useful in the compositions described herein are those that are pharmaceutically and/or immunologically acceptable. The carrier is typically a liquid but certain hydrophobic substances that are not liquids at atmospheric temperature may be liquefied, for example by warming, and may also be useful.

Oil or a mixture of oils is a particularly suitable carrier for use in the adjuvanting system and compositions disclosed herein. Oils should be pharmaceutically and/or immunologically acceptable. Suitable oils include, for example, mineral oils (especially light or low viscosity mineral oil such as Drakeol® 6VR), vegetable oils (e.g., soybean oil), nut oils (e.g., peanut oil), or mixtures thereof. Thus, in an embodiment the hydrophobic carrier is a hydrophobic substance such as vegetable oil, nut oil or mineral oil. Animal fats and artificial hydrophobic polymeric materials, particularly those that are liquid at atmospheric temperature or that can be liquefied relatively easily, may also be used.

In some embodiments, the hydrophobic carrier may be, or comprise, Incomplete Freund's Adjuvant (IFA), a mineral oil-based model hydrophobic carrier. In another embodiment, the hydrophobic carrier may be, or comprise, a mannide oleate in mineral oil solution, such as that commercially available as MONTANIDE® ISA 51 (SEPPIC, France). While these carriers are commonly used to prepare water-in-oil emulsions, the present disclosure avoids this type of formulation by use of an amphipathic compound to suspend the components in the absence of substantial quantities of water, as described herein.

Immunovaccine Inc. has developed a vaccine delivery platform referred to as DepoVax™ (DPX). DPX is a lipid-in-oil formulation that can be formulated with any antigen, or mixture of antigens. Unlike water-in-oil emulsion based vaccines, which rely on oil entrapping water droplets containing antigen and adjuvant, DepoVax™ based formulations rely on lipids to facilitate the incorporation of antigens and adjuvants directly into the oil, without the need for emulsification. Advantages of this approach include: (1) enhancing the solubility of hydrophilic antigens/adjuvant in oil diluents which otherwise would normally have maximum solubility in aqueous based diluents, and (2) the elimination of cumbersome emulsification procedures prior to vaccine administration.

In some embodiments, the hydrophobic carrier of the adjuvanting system and vaccine compositions disclosed herein may be Immunovaccine, Inc's delivery platform DepoVax™.

Vaccine Compositions

The adjuvanting system disclosed herein may be combined or mixed with one or more antigens to provide a vaccine composition, such as for example, a water-free vaccine composition as disclosed herein.

As used herein, the terms "vaccine", "vaccine composition" or "composition" may be used interchangeably, as the context requires.

Vaccine compositions as disclosed herein may be administered to a subject in a therapeutically effect amount. As used herein, a "therapeutically effective amount" means an amount of the vaccine or active ingredient (e.g., one or more antigens) effective to stimulate, induce, maintain, boost or enhance an immune response in a subject. In some embodiments, a therapeutically effective amount of the vaccine is an amount capable of inducing a clinical response in a subject in the treatment of a particular disease or disorder. Determination of a therapeutically effective amount of the vaccine is well within the capability of those skilled in the art, especially in light of the disclosure provided herein. The therapeutically effective amount may vary according to a variety of factors such as the subject's condition, weight, sex and age.

In an embodiment, the vaccine composition comprises the adjuvanting system as disclosed herein, together with one or more antigens. Thus, in an embodiment, the present disclosure relates to a composition comprising: (a) an antigen; (b) a polyI:C polynucleotide adjuvant; (c) a lipid-based adjuvant; (d) an amphipathic compound; and (e) a hydrophobic carrier. The polyI:C polynucleotide adjuvant; lipid-based adjuvant; amphipathic compound; and hydrophobic carrier are as disclosed herein above.

Antigens

The compositions disclosed herein may comprise one or more antigens.

As used herein, the term "antigen" refers to any substance or molecule that can bind specifically to components of the immune system. In some embodiments, suitable antigens of the compositions herein are those that are capable of inducing or generating an immune response in a subject. An antigen that is capable of inducing an immune response is said to be immunogenic, and may also be called an immunogen. Thus, as used herein, the term "antigen" includes immunogens and the terms may be used interchangeably unless specifically stated otherwise. The term antigen, as used herein, also includes haptens. As is understood in the art, a hapten is a small molecule that is antigenic (e.g. capable of being bound by components of the immune system), but is not immunogenic unless it is attached to a carrier molecule.

Antigens that may be useful in the compositions disclosed herein include, for example and without limitation, a polypeptide, carbohydrate, a microorganism or a part thereof, such as a live, attenuated, inactivated or killed bacterium, virus or protozoan, or part thereof. The antigen may be, for example, a pathogenic biological agent, a toxin, an allergen, a peptide, a suitable native, non-native, recombinant or denatured protein or polypeptide, or a fragment thereof, or an epitope that is capable of inducing or potentiating an immune response in a subject. In some embodiments, the antigen may be one that is derived from an animal (an animal antigen), such as for example a human (a human antigen), or an antigen that is substantially related thereto.

As used herein, the term "derived from" encompasses, without limitation: an antigen that is isolated or obtained directly from an originating source (e.g. a subject); a synthetic or recombinantly generated antigen that is identical or substantially related to an antigen from an originating source; or an antigen which is made from an antigen of an originating source or a fragment thereof. When it is stated that an antigen is "from" a source, the term "from" may be equated with "derived from". The term "substantially related", as this context, means that the antigen may have been modified by chemical, physical or other means (e.g. sequence modification), but that the resultant product remains capable of generating an immune response to the original antigen or to the disease or disorder associated with the original antigen.

As used herein, the term "antigen" also includes a polynucleotide that encodes a polypeptide that functions as an antigen. Nucleic acid-based vaccination strategies are known, wherein a vaccine composition that contains a polynucleotide is administered to a subject. The antigenic polypeptide encoded by the polynucleotide is expressed in the subject, such that the antigenic polypeptide is ultimately present in the subject, just as if the vaccine composition itself had contained the polypeptide. For the purposes of the present disclosure, the term "antigen", where the context dictates, encompasses such polynucleotides that encode the polypeptide which functions as the antigen.

In some embodiments, the antigen is a molecule comprising at least one B cell epitope or CTL epitope, as defined below, and which, when suitably administered to a subject, induces or potentiates a humoral and/or cell-mediated immune response which is protective against the disease.

In some embodiments, the antigen may be one that is associated with cancer, an infectious disease, or an addiction disease.

Viruses, or parts thereof, that may be useful as antigens in the compositions herein include for example, and without limitation, Cowpoxvirus, Vaccinia virus, Pseudocowpox virus, herpes virus, Human herpesvirus 1, Human herpesvirus 2, Cytomegalovirus, Human adenovirus A-F, Polyomavirus, human papillomavirus (HPV), Parvovirus, Hepatitis A virus, Hepatitis B virus, Hepatitis C virus, human immunodeficiency virus (HIV), Orthoreovirus, Rotavirus, Ebola virus, parainfluenza virus, influenza virus (e.g. H5N1 influenza virus, influenza A virus, influenza B virus, influenza C virus), Measles virus, Mumps virus, Rubella virus, Pneumovirus, respiratory syncytial virus, human respiratory syncytial virus, Rabies virus, California encephalitis virus, Japanese encephalitis virus, Hantaan virus, Lymphocytic choriomeningitis virus, Coronavirus, Enterovirus, Rhinovirus, Poliovirus, Norovirus, Flavivirus, Dengue virus, West Nile virus, Yellow fever virus and varicella.

In an embodiment, a composition disclosed herein comprises an antigen that may potentially be useful for treating and/or preventing an influenza virus infection in a subject in need thereof. Influenza is a single-stranded RNA virus of the family Orthomyxoviridae and is often characterized based on two large glycoproteins on the outside of the viral particle, hemagglutinin (HA) and neuraminidase (NA). Numerous HA subtypes of influenza A have been identified (Kawaoka et al. 1990; Webster et al. 1983). In some embodiments, the antigen may be derived from the HA or NA glycoproteins. In a particular embodiment, the antigen may be recombinant HA antigen (H5N1, A/Vietnam/1203/2004; Protein Sciences; USA), such as derived from the sequence found under Genbank Accession number AY818135 or any suitable sequence variant thereof.

In another embodiment, a composition disclosed herein comprises an antigen that may potentially be useful for treating and/or preventing an Ebola virus infection in a subject in need thereof.

In another embodiment, a composition disclosed herein comprises an antigen that may potentially be useful for treating and/or preventing a human papillomavirus (HPV) infection in a subject in need thereof. In more particular embodiments, a composition disclosed herein comprises an antigen that may potentially be useful for treating and/or preventing a HPV-related cervical cancer or HPV-related head and neck cancer. In some embodiments, the antigen is a peptide comprising the sequence RAHYNIVTF (HPV16E7 (H-2Db) peptide 49-57; R9F; SEQ ID NO: 2).

In another embodiment, a composition disclosed herein comprises an antigen that may potentially be useful for treating and/or preventing a respiratory syncytial virus (RSV) infection in a subject in need thereof. In more particular embodiments, a composition disclosed herein comprises an antigen that may potentially be useful for treating and/or preventing a lung disease associated with a RSV infection. In some embodiments, the antigen is derived from the ectodomain of the small hydrophobic protein as disclosed, for example, in WO2012/065997. In some embodiments, the sequence of the antigen is derived from the small hydrophobic domain of RSV stain A: NKLC-EYNVFHNKTFELPRARVNT (SEQ ID NO: 22) (Schepens et al. 2014; WO 2012/065997), or any suitable sequence variant thereof.

Bacteria or parts thereof that may be useful as antigens in the compositions herein include for example, and without limitation, Anthrax (*Bacillus anthracis*), *Brucella, Bordetella pertussis, Candida, Chlamydia pneumoniae, Chlamydia psittaci,* Cholera, *Clostridium botulinum, Coccidioides immitis, Cryptococcus,* Diphtheria, *Escherichia coli O157*: H7, Enterohemorrhagic *Escherichia coli*, Enterotoxigenic *Escherichia coli, Haemophilus influenzae, Helicobacter pylori, Legionella, Leptospira, Listeria,* Meningococcus, *Mycoplasma pneumoniae, Mycobacterium,* Pertussis, Pneumonia, *Salmonella, Shigella, Staphylococcus, Streptococcus pneumoniae* and *Yersinia enterocolitica.*

In an embodiment, a composition disclosed herein comprises an antigen that may potentially be useful for treating and/or preventing a *Bacillus anthracis* infection (i.e. Anthrax) in a subject in need thereof. Without limitation, the antigen contained in the composition may for example be anthrax recombinant protective antigen (rPA) (List Biological Laboratories, Inc.; Campbell, Calif.) or anthrax mutant recombinant protective antigen (mrPA) (Pfenex, Inc.; San Diego, Calif.). In some embodiments the antigen may be derived from the sequence found under Genbank Accession number P13423, or any suitable sequence variant thereof.

Protozoa or parts thereof that may be useful as antigens in the compositions herein include for example, and without limitation, the genus *Plasmodium* (*Plasmodium falciparum, Plasmodium malariae, Plasmodium vivax, Plasmodium ovale* or *Plasmodium knowlesi*), which causes malaria.

In an embodiment, a composition disclosed herein comprises an antigen that may potentially be useful for treating and/or preventing a *Plasmodium malariae* infection (i.e. malaria) in a subject in need thereof.

The antigen may alternatively be a naturally occurring or synthesized toxin or allergen. A "toxin", as used herein, refers to any substance produced by living cells or organisms (e.g. plants, animals, microorganisms, etc.) that is capable of causing a disease or ailment, or an infectious substance, or a recombinant or synthesized molecule capable of adverse effect. Toxins may be for example small molecules, peptides, or proteins. Toxins include drug substances such as, for example, cocaine. The toxin may be capable of being neutralized by an antibody. In such embodiments, the antigen may elicit the production of antibodies that bind to and sequester the toxin in circulation (e.g. the blood), thereby potentially preventing its delivery to another area of the body (e.g. the brain).

An "allergen", as used herein, refers to any substance that can cause an allergy. The allergen may be derived from, without limitation, cells, cell extracts, proteins, polypeptides, peptides, polysaccharides, polysaccharide conjugates, peptide and non-peptide mimics of polysaccharides and other molecules, small molecules, lipids, glycolipids, and carbohydrates of plants, animals, fungi, insects, food, drugs, dust, and mites. Allergens include but are not limited to environmental aeroallergens; plant pollens (e.g. ragweed/hayfever); weed pollen allergens; grass pollen allergens; Johnson grass; tree pollen allergens; ryegrass; arachnid allergens (e.g. house dust mite allergens); storage mite allergens; Japanese cedar pollen/hay fever; mold/fungal spore allergens; animal allergens (e.g., dog, guinea pig, hamster, gerbil, rat, mouse, etc., allergens); food allergens (e.g. crustaceans; nuts; citrus fruits; flour; coffee); insect allergens (e.g. fleas, cockroach); venoms: (Hymenoptera, yellow jacket, honey bee, wasp, hornet, fire ant); bacterial allergens (e.g. streptococcal antigens; parasite allergens such as *Ascaris* antigen); viral antigens; drug allergens (e.g. penicillin); hormones (e.g. insulin); enzymes (e.g. streptokinase); and drugs or chemicals capable of acting as incomplete antigens or haptens (e.g. the acid anhydrides and the isocyanates).

Where a hapten is used in a composition disclosed herein, it may be attached to a carrier, such as for example a protein, to form a hapten-carrier adduct. The hapten-carrier adduct is capable of eliciting an immune response, whereas the hapten itself would not typically elicit a response. Non-limiting examples of haptens are aniline, urushiol (a toxin in poison ivy), hydralazine, fluorescein, biotin, digoxigenin and dinitrophenol.

In another embodiment, the antigen may be an antigen associated with a disease where it is desirable to sequester the antigen in circulation, such as for example an amyloid protein (e.g. Alzheimer's disease). Thus, in some embodiments, a composition as disclosed herein comprises an antigen that may potentially be useful in the treatment and/or prevention of a neurodegenerative disease in a subject in need thereof, wherein the neurodegenerative disease is associated with the expression of the antigen.

In another embodiment, the antigen may be any one or more of the antigens disclosed in WO 2007/041832, such as for example the peptide antigens disclosed in Table 1 at pages 17-19 of WO 2007/041832.

For example, and without limitation, polypeptides or fragments thereof that may be useful as antigens in the compositions herein include those derived from Cholera toxoid, tetanus toxoid, diphtheria toxoid, hepatitis B surface antigen, hemagglutinin (e.g. H5N1 recombinant hemagglutinin protein), anthrax recombinant protective antigen (List Biological Laboratories, Inc.; Campbell, Calif.), anthrax mutant recombinant protective antigen (Pfenex, Inc.; San Diego, Calif.), neuraminidase, influenza M protein, PfHRP2, pLDH, aldolase, MSP1, MSP2, AMA1, Der-p-1, Der-f-1, Adipophilin, AFP, AIM-2, ART-4, BAGE, α-feto protein, BCL-2, Bcr-Abl, BING-4, CEA, CPSF, CT, cyclin D1Ep-CAM, EphA2, EphA3, ELF-2, FGF-5, G250, Gonadotropin Releasing Hormone (GNRH), HER-2, intestinal carboxyl esterase (iCE), IL13Rα2, MAGE-1, MAGE-2, MAGE-3, MART-1, MART-2, M-CSF, MDM-2, MMP-2, MUC-1, NY-EOS-1, MUM-1, MUM-2, MUM-3, pertussis toxoid protein, p53, PBF, PRAME, PSA, PSMA, RAGE-1, RNF43, RU1, RU2AS, SART-1, SART-2, SART-3, SAGE-1, SCRN 1, SOX2, SOX10, STEAP1, survivin, Telomerase, TGFβRII, TRAG-3, TRP-1, TRP-2, TERT and WT1.

The term "polypeptide" encompasses any chain of amino acids, regardless of length (e.g., at least 6, 8, 10, 12, 14, 16, 18, or 20 amino acids) or post-translational modification (e.g., glycosylation or phosphorylation), and includes, for example, natural proteins, synthetic or recombinant polypeptides and peptides, epitopes, hybrid molecules, variants, homologs, analogs, peptoids, peptidomimetics, etc. A variant or derivative therefore includes deletions, including truncations and fragments; insertions and additions, for example conservative substitutions, site-directed mutants and allelic variants; and modifications, including peptoids having one or more non-amino acyl groups (for example, sugar, lipid, etc.) covalently linked to the peptide and post-translational modifications. As used herein, the term "conserved amino acid substitutions" or "conservative substitutions" refers to the substitution of one amino acid for another at a given location in the peptide, where the substitution can be made without substantial loss of the relevant function. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing. Specific, non-limiting examples of a conservative substitution include the following examples:

| Original Residue | Conservative Substitution |
| --- | --- |
| Ala | Ser |
| Arg | Lys |
| Asn | Gln, His |
| Asp | Glu |
| Cys | Ser |
| Gln | Asn |
| Glu | Asp |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Val | Ile, Leu |

Polypeptides or peptides that have substantial identity to an antigen sequence may be used. Two sequences are considered to have substantial identity if, when optimally aligned (with gaps permitted), they share at least approximately 50% sequence identity, or if the sequences share defined functional motifs. In alternative embodiments, optimally aligned sequences may be considered to be substantially identical (i.e., to have substantial identity) if they share at least 60%, 70%, 75%, 80%, 85%, 90%, 95%, 96%, 97%, 98%, 99% identity over a specified region. The term "identity" refers to sequence similarity between two polypeptides molecules. Identity can be determined by comparing each position in the aligned sequences. A degree of identity between amino acid sequences is a function of the number of identical or matching amino acids at positions shared by the sequences, for example, over a specified region. Optimal alignment of sequences for comparisons of identity may be conducted using a variety of algorithms, as are known in the art, including the ClustalW program, the local homology algorithm of Smith and Waterman (1981), the homology alignment algorithm of Needleman and Wunsch (1970), the search for similarity method of Pearson and Lipman (1988), and the computerised implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al. (1990) (using the published default settings). For example, the "BLAST 2 Sequences" tool, available through the National Center for Biotechnology Information may be used, selecting the "blastp" program at the following default settings: expect threshold 10; word size 3; matrix BLOSUM 62; gap costs existence 11, extension 1. In another embodiment, the person skilled in the art can readily and properly align any given sequence and deduce sequence identity and/or homology by mere visual inspection.

Polypeptides and peptides used to practice the invention can be isolated from natural sources, be synthetic, or be recombinantly generated polypeptides. Peptides and proteins can be recombinantly expressed in vitro or in vivo. The peptides and polypeptides used to practice the invention can be made and isolated using any method known in the art. Polypeptide and peptides used to practice the invention can also be synthesized, whole or in part, using chemical methods well known in the art. See e.g., Caruthers 1980, Hom 1980, Banga, 1995. For example, peptide synthesis can be performed using various solid-phase techniques (see e.g., Roberge 1995, Merrifield 1997) and automated synthesis may be achieved, e.g., using the ABI 431A Peptide Synthesizer (Perkin Elmer) in accordance with the instructions provided by the manufacturer.

In some embodiments, the antigen may be a purified antigen, e.g., from about 25% to 50% pure, from about 50% to about 75% pure, from about 75% to about 85% pure, from about 85% to about 90% pure, from about 90% to about 95% pure, from about 95% to about 98% pure, from about 98% to about 99% pure, or greater than 99% pure.

As noted above, the term "antigen" also includes a polynucleotide that encodes the polypeptide that functions as an antigen. As used herein, the term "polynucleotide" encompasses a chain of nucleotides of any length (e.g. 9, 12, 18, 24, 30, 60, 150, 300, 600, 1500 or more nucleotides) or number of strands (e.g. single-stranded or double-stranded). Polynucleotides may be DNA (e.g. genomic DNA or cDNA) or RNA (e.g. mRNA) or combinations thereof. They may be naturally occurring or synthetic (e.g. chemically synthesized). It is contemplated that the polynucleotide may contain modifications of one or more nitrogenous bases, pentose sugars or phosphate groups in the nucleotide chain. Such modifications are well-known in the art and may be for the purpose of e.g. improving stability of the polynucleotide.

The polynucleotide may be delivered in various forms. In some embodiments, a naked polynucleotide may be used, either in linear form, or inserted into a plasmid, such as an expression plasmid. In other embodiments, a live vector such as a viral or bacterial vector may be used.

One or more regulatory sequences that aid in transcription of DNA into RNA and/or translation of RNA into a polypeptide may be present. In some instances, such as in the case of a polynucleotide that is a messenger RNA (mRNA) molecule, regulatory sequences relating to the transcription process (e.g. a promoter) are not required, and protein expression may be effected in the absence of a promoter. The skilled artisan can include suitable regulatory sequences as the circumstances require.

In some embodiments, the polynucleotide is present in an expression cassette, in which it is operably linked to regulatory sequences that will permit the polynucleotide to be expressed in the subject to which the composition as disclosed herein is administered. The choice of expression cassette depends on the subject to which the composition is administered as well as the features desired for the expressed polypeptide.

Typically, an expression cassette includes a promoter that is functional in the subject and can be constitutive or inducible; a ribosome binding site; a start codon (ATG) if necessary; the polynucleotide encoding the polypeptide of interest; a stop codon; and optionally a 3' terminal region (translation and/or transcription terminator). Additional sequences such as a region encoding a signal peptide may be included. The polynucleotide encoding the polypeptide of interest may be homologous or heterologous to any of the other regulatory sequences in the expression cassette.

Sequences to be expressed together with the polypeptide of interest, such as a signal peptide encoding region, are typically located adjacent to the polynucleotide encoding the protein to be expressed and placed in proper reading frame. The open reading frame constituted by the polynucleotide encoding the protein to be expressed solely or together with any other sequence to be expressed (e.g. the signal peptide), is placed under the control of the promoter so that transcription and translation occur in the subject to which the composition is administered.

In an embodiment, the compositions disclosed herein comprise an antigen that is a self-antigen. In embodiment, the compositions disclosed herein comprise an antigen that is a cancer-associated antigen.

The amount of antigen used in a single treatment with a composition as described herein may vary depending on the type of antigen and characteristics of the subject (e.g. size, weight, age, sex, etc). One skilled in the art will be able to determine, without undue experimentation, the effective amount of antigen to use in a particular application. The term "effective amount" as used herein means an amount effective, at dosages and for periods of time necessary, to achieve the desired result.

In an embodiment, the composition may comprise about 0.5, 1, 1.5, 2, 2.5, 3, 3.5, 4, 4.5, 5, 5.5, 6, 6.5, 7, 7.5, 8, 8.5, 9, 9.5 or 10 micrograms of the antigen per unit dose as calculated in mice, or an equivalent translated dose for humans. In some embodiments, the composition may comprise an equivalent dose of antigen as the polyI:C and/or lipid-based adjuvants. In a particular embodiment, the composition may comprise about 1 microgram of the antigen per unit dose as calculated in mice, or an equivalent translated dose for humans. Without limitation, the per unit dose amount of antigen for human administration may be up to 500 micrograms, and is typically 100 micrograms or less.

Dose translation from human to murine studies may be calculated using the equation provided earlier herein.

Cancer-Associated Antigens

In some embodiments, the antigen may be a cancer or tumor-associated protein or a fragment thereof. Many cancer or tumor-associated proteins are known in the art such as for example, and without limitation, those disclosed in WO 2007/041832.

In some embodiments, the cancer may be caused by a pathogen, such as a virus. Viruses linked to the development of cancer are known to the skilled person and include, but are not limited to, human papillomaviruses (HPV), John Cunningham virus (JCV), Human herpes virus 8, Epstein Barr Virus (EBV), Merkel cell polyomavirus, Hepatitis C Virus and Human T cell leukaemia virus-1. Thus, in an embodiment, a composition disclosed herein may comprise an antigen associated a virus that is linked to the development of cancer.

In some embodiments, the antigen may be any one that is capable of inducing a specific cytotoxic T-lymphocyte (CTL) immune response that is able to effectively recognize a specific conformation on targeted tumor cells and cause their destruction.

In still further embodiments, the antigen may comprise a peptide sequence selected from the following table:

TABLE 4

| Antigen | Sequence | HLA | Patent |
|---|---|---|---|
| Mart-1/ Melan-A | AAGIGILTV (SEQ ID NO: 23) | A2 | U.S. Pat. No. 5,844,075 |
| | EAAGIGILTV (SEQ ID NO: 24) | A2 | U.S. Pat. No. 5,844,075 |
| | ILTVILGVL (SEQ ID NO: 25) | A2 | U.S. Pat. No. 5,844,075 |
| | AEEAAGIGIL (SEQ ID NO: 26) | B45 | U.S. Pat. No. 7,037,509 |
| | AEEAAGIGILT (SEQ ID NO: 27) | B45 | Unknown |
| MCIR | TILLGIFFL (SEQ ID NO: 28) | A2 | Unknown |
| | FLALIICNA (SEQ ID NO: 29) | A2 | Unknown |
| Gp100 | KTWGQYWQV (SEQ ID NO: 30) | A2 | U.S. Pat. No. 5,844,075 |
| | AMLGTHTMEV (SEQ ID NO: 31) | A2 | Unknown |
| | MLGTHTMEV (SEQ ID NO: 32) | A2 | Unknown |
| | SLADTNSLAV (SEQ ID NO: 33) | A2 | U.S. Pat. No. 5,844,075 |
| | ITDQVPFSV (SEQ ID NO: 34) | A2 | U.S. Pat. No. 5,844,075 |
| | LLDGTATLRL (SEQ ID NO: 35) | A2 | U.S. Pat. No. 5,844,075 |
| | YLEPGPVTA (SEQ ID NO: 36) | A2 | U.S. Pat. No. 5,844,075 |
| | VLYRYGSFSV (SEQ ID NO: 37) | A2 | U.S. Pat. No. 5,844,075 |
| | RLPRIFCSC (SEQ ID NO: 38) | A2 | Unknown |
| | LIYRRRLMK (SEQ ID NO: 39) | A3 | Unknown |
| | ALNFPGSQK (SEQ ID NO: 40) | A3 | Unknown |
| | SLIYRRRLMK (SEQ ID NO: 41) | A3 | Unknown |
| | ALLAVGATK (SEQ ID NO: 42) | A3 | U.S. Pat. No. 6,558,671 |
| | ALLAVGATK (SEQ ID NO: 42) | A3 | U.S. Pat. No. 6,977,074 |
| | VYFFLPDHL (SEQ ID NO: 43) | A24 | Unknown |
| | SNDGPTLI (SEQ ID NO: 44) | Cw8 | Unknown |
| PSA | VSHSFPHPLY (SEQ ID NO: 45) | A1 | U.S. Pat. No. 6,037,135 |
| | FLTPKKLQCV (SEQ ID NO: 46) | A2 | U.S. Pat. No. 6,881,405 |
| | VISNDVCAQV (SEQ ID NO: 47) | A2 | Unknown |
| PSM | HSTNGVTRIY (SEQ ID NO: 48) | A1 | Unknown |
| Tyrosinase | KCDICTDEY (SEQ ID NO: 49) | A1 | U.S. Pat. No. 7,019,112 |
| | SSDYVIPIGTY (SEQ ID NO: 50) | A1 | Unknown |
| | YMDGTMSQV (SEQ ID NO: 51) | A2 | U.S. Pat. No. 6,096,313 |
| | MLLAVLYCL (SEQ ID NO: 51) | A2 | U.S. Pat. No. 6,291,430 |
| | AFLPWHRLF (SEQ ID NO: 53) | A24 | U.S. Pat. No. 6,291,430 |
| | SEIWRDIDF (SEQ ID NO: 54) | B44 | U.S. Pat. No. 6,291,430 |
| | MSLQRQFLR (SEQ ID NO: 55) | A31 | U.S. Pat. No. 5,831,016 |

TABLE 4-continued

| Antigen | Sequence | | HLA | Patent |
|---|---|---|---|---|
| TRP1 | SVYDFFVWL | (SEQ ID NO: 56) | A2 | U.S. Pat. No. 7,067,120 |
| TRP2 | TLDSQVMSL | (SEQ ID NO: 57) | A2 | Unknown |
|  | LLGPGRPYR | (SEQ ID NO: 58) | A31 | U.S. Pat. No. 5,831,016 |
| p53 | ANDPIFVVL | (SEQ ID NO: 59) | Cw8 | Unknown |

In a particular embodiment, the compositions as disclosed herein may comprise an antigen derived from HPV. In an embodiment, the antigen may be derived from the E6, E7, L1 or L2 protein of HPV.

In an embodiment, the antigen of E6 protein of HPV comprises the peptide sequence TIHDIILECV (T10V; SEQ ID NO: 60). In another embodiment, the antigen of the E7 protein of HPV comprises a peptide sequence of RAHYNIVTF (R9F; SEQ ID NO: 2), YMLDLQPETT (Y10T; SEQ ID NO: 61), LLMGTLGIV (L9V; SEQ ID NO: 62), or TLGIVCPI (T8I; SEQ ID NO: 63).

In other embodiment, the antigen derived from HPV may be one or more of the HPV antigens disclosed in WO1993/022338, WO2002/070006, WO2006/115413, WO2008/147187, WO2009/002159 or WO2010/123365.

In another embodiment, the antigen may be derived from a tumor-associated protein, such as for example, a melanoma-associated protein. In a further embodiment, the melanoma-associated protein is a tyrosine related protein-2 (TRP-2) or p53. In one embodiment an antigen derived from a TRP-2 protein comprises the peptide sequence SVYDFFVWL (S9L; SEQ ID NO: 56). In another embodiment, an antigen derived from a TRP-2 protein comprises the peptide sequence VYDFFVWL (V8L; SEQ ID NO: 64). In another embodiment, an antigen derived from a p53 protein comprises a peptide sequence selected from KYMCNSSCM (K9M; wild type p53; SEQ ID NO: 65), KYICNSSCM (mK9M; modified p53; SEQ ID NO: 66), and AKXVAAWTLKAAAKYICNSSCM (mK9M; SEQ ID NO: 67).

In an embodiment, the antigen contained in the compositions may comprise a mixture of one or more of the antigens described herein, optionally fused together as a fused protein with or without spacer sequences between the antigens.

In other embodiments, and without limitation, the antigen may be from a membrane surface-bound cancer-associated protein. The surface-bound cancer-associated protein (or antigen thereof) may be capable of being recognized by an antibody.

In a particular embodiment, the compositions as disclosed herein may comprise one or more survivin antigens.

Survivin, also called baculoviral inhibitor of apoptosis repeat-containing 5 (BIRC5), is a protein involved in the negative regulation of apoptosis. It has been classed as a member of the family of inhibitors of apoptosis proteins (IAPs). Survivin is a 16.5 kDa cytoplasmic protein containing a single BIR motif and a highly charged carboxy-terminal coiled region instead of a RING finger. The gene coding for survivin is nearly identical to the sequence of Effector Cell Protease Receptor-1 (EPR-1), but oriented in the opposite direction. The coding sequence for the survivin (*Homo sapiens*) is 429 nucleotides long including stop codons:

```
                                                    SEQ ID NO: 68
atgggtgccc cgacgttgcc ccctgcctgg cagcccttc tcaaggacca ccgcatctct    60
acattcaaga actggccctt cttggagggc tgcgcctgca ccccggagcg gatggccgag   120
gctggcttca tccactgccc cactgagaac gagccagact tggcccagtg tttcttctgc   180
ttcaaggagc tggaaggctg ggagccagat gacgacccca tagaggaaca taaaaagcat   240
tcgtccggtt gcgctttcct ttctgtcaag aagcagtttg aagaattaac ccttggtgaa   300
tttttgaaac tggacagaga aagagccaag aacaaaattg caaaggaaac caacaataag   360
aagaaagaat ttgaggaaac tgcgaagaaa gtgcgccgtg ccatcgagca gctggctgcc   420
atggattga                                                          429
```

The encoded protein survivin (*Homo sapiens*) is 142 amino acids long:

```
                                                    SEQ ID NO: 69
Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45
```

```
Glu Asn Glu Pro Asp Leu Ala Gln Cys Phe Phe Cys Phe Lys Glu Leu
     50                  55                  60

Glu Gly Trp Glu Pro Asp Asp Pro Ile Glu Glu His Lys Lys His
 65              70                  75                  80

Ser Ser Gly Cys Ala Phe Leu Ser Val Lys Lys Gln Phe Glu Glu Leu
             85                  90                  95

Thr Leu Gly Glu Phe Leu Lys Leu Asp Arg Glu Arg Ala Lys Asn Lys
            100                 105                 110

Ile Ala Lys Glu Thr Asn Asn Lys Lys Lys Glu Phe Glu Glu Thr Ala
        115                 120                 125

Lys Lys Val Arg Arg Ala Ile Glu Gln Leu Ala Ala Met Asp
    130                 135                 140
```

It is postulated that the survivin protein functions to inhibit caspase activation, thereby leading to negative regulation of apoptosis or programmed cell death. Consistent with this function, survivin has been identified as one of the top genes invariably up-regulated in many types of cancer but not in normal tissue (see e.g. Altieri et al. 1999; and U.S. Pat. No. 6,245,523). This fact therefore makes survivin an ideal target for cancer therapy as cancer cells are targeted while normal cells are not. Indeed, survivin is highly expressed in many tumor types, including a large portion of human cancer, and has reported prognostic value.

In some embodiments, compositions as disclosed herein may comprise one or more survivin antigens. As used herein, the term "survivin antigen" encompasses any peptide, polypeptide or variant thereof (e.g. survivin peptide variant) derived from a survivin protein or a fragment thereof. The term "survivin antigen" also encompasses a polynucleotide that encodes a survivin peptide, survivin peptide variant or survivin peptide functional equivalent described herein. Polynucleotides may be DNA (e.g. genomic DNA or cDNA) or RNA (e.g. mRNA) or combinations thereof. They may be naturally occurring or synthetic (e.g. chemically synthesized). It is contemplated that the polynucleotide may contain modifications of one or more nitrogenous bases, pentose sugars or phosphate groups in the nucleotide chain. Such modifications are well-known in the art and may be for the purpose of e.g. improving stability of the polynucleotide.

In an embodiment, the survivin antigen may comprise the full length survivin polypeptide or a nucleic acid encoding the full length survivin polypeptide. Alternatively, the survivin antigen may be a survivin peptide comprising a fragment of any length of the survivin protein. Exemplary embodiments include a survivin peptide that comprises at least 5, 6, 7, 8, 9, 10, 11, 12, 13, 14, 15, 16, 17, 18, 19 or 20 amino acid residues. In specific embodiments, the survivin peptide consists of a heptapeptide, an octapeptide, a nonapeptide, a decapeptide or an undecapeptide, consisting of 7, 8, 9, 10, 11 consecutive amino acid residues of the survivin protein (e.g. SEQ ID NO: 69), respectively. Particular embodiments of the survivin antigen include survivin peptides of about 9 or 10 amino acids.

Survivin antigens of the present disclosure also encompass variants and functional equivalents of survivin peptides. Variants or functional equivalents of a survivin peptide encompass peptides that exhibit amino acid sequences with differences as compared to the specific sequence of the survivin protein, such as one or more amino acid substitutions, deletions or additions, or any combination thereof. The difference may be measured as a reduction in identity as between the survivin protein sequence and the survivin peptide variant or survivin peptide functional equivalent.

The identity between amino acid sequences may be calculated using algorithms well known in the art. Survivin peptide variants or functional equivalents are to be considered as falling within the meaning of a "survivin antigen" when they are, over their entire length, at least 70% identical to a peptide sequence of a survivin protein, such as at least 75% identical, at least 80% identical, at least 85% identical, at least 90% identical, or at least 95% identical, including 96%, 97%, 98% or 99% identical with a peptide sequence of a survivin protein. In a particular embodiment, the survivin peptide variant has a sequence that is at least 85%, 90%, 95%, 96%, 97%, 98% or 99% identical to a consecutive amino acid sequence of SEQ ID NO: 69.

The survivin protein from which the survivin antigen can be derived is a survivin protein from any animal species in which the protein is expressed. A particular embodiment is the survivin protein from humans (SEQ ID NO: 69). Based on the sequence of the selected survivin protein, the survivin antigen may be derived by any appropriate chemical or enzymatic treatment of the survivin protein or coding nucleic acid. Alternatively, the survivin antigen may be synthesized by any conventional peptide or nucleic acid synthesis procedure with which the person of ordinary skill in the art is familiar.

The survivin antigen (peptide or nucleic acid) may have a sequence which is a native sequence of survivin. Alternatively, the survivin antigen may be a peptide or nucleic acid sequence modified by one or more substitutions, deletions or additions, such as e.g. the survivin peptide variants or functional equivalents described herein. Exemplary procedures and modifications of survivin peptides that increase the immunogenicity of the peptides include, for example, those described in WO 2004/067023 involving amino acid substitutions introduced at anchor positions which increase peptide binding to the HLA class I molecule.

In an embodiment, the survivin antigen is any peptide derived from the survivin protein, or any survivin peptide variant thereof, that is capable of binding MHC Class I HLA molecules. Along these lines, the survivin antigen may be any survivin peptide, or survivin peptide variant thereof, that is capable of inducing or potentiating an immune response in a subject.

In an embodiment, the survivin antigen is a peptide antigen comprising an amino acid sequence from the survivin protein (e.g. SEQ ID NO: 69) that is capable of eliciting a cytotoxic T-lymphocyte (CTL) response in a subject, or a nucleic acid molecule encoding said peptide.

In an embodiment, the compositions comprises one or more synthetic survivin peptides, or variants thereof, based on the amino acid sequence of the survivin protein, such as the amino acid sequence set forth in SEQ ID NO: 69.

Survivin peptides, survivin peptide variants and survivin functional equivalents, and their use for diagnostic and therapeutic purposes, specifically in cancer, have been described, for example, in WO 2004/067023 and WO 2006/081826. The novel peptides disclosed in these publications were found to be capable of eliciting cytotoxic T-lymphocyte (CTL) responses in cancer patients. In particular, in WO 2004/067023, it was found that MHC Class I restricted peptides can be derived from the survivin protein, which are capable of binding to MHC Class I HLA molecules and thereby eliciting both ex vivo and in situ CTL immune responses in patients suffering from a wide range of cancer diseases.

In an embodiment, a composition as disclosed herein may include any one or more of the survivin peptides, survivin peptide variants or survivin peptide functional equivalents disclosed in WO 2004/067023 and WO 2006/081826.

In another embodiment, a composition as disclosed herein may include one or more of a survivin peptide, survivin peptide variant or survivin peptide functional equivalent having the ability to bind any of the MHC Class I molecules selected from HLA-A, HLA-B or HLA-C molecules.

Exemplary MHC Class I HLA-A molecules to which the survivin peptide, survivin peptide variant, or survivin peptide functional equivalent may bind include, without limitation, HLA-A1, HLA-A2, HLA-A3, HLA-A9, HLA-A10, HLA-A11, HLA-A19, HLA-A23, HLA-A24, HLA-A25, HLA-A26, HLA-A28, HLA-A29, HLA-A30, HLA-A31, HLA-A32, HLA-A33, HLA-A34, HLA-A36, HLA-A43, HLA-A66, HLA-A68, and HLA-A69.

Exemplary MHC Class I HLA-B molecules to which the survivin peptide, survivin peptide variant, or survivin peptide functional equivalent may bind include, without limitation, HLA-B5, HLA-B7, HLA-B8, HLA-B12, HLA-B13, HLA-B14, HLA-B15, HLA-B16, HLA-B17, HLA-B18, HLA-B21, HLA-B22, HLA-B27, HLA-B35, HLA-B37, HLA-B38, HLA-B39, HLA-B40, HLA-B41, HLA-B42, HLA-B44, HLA-B45, HLA-B46 and HLA-B47.

Exemplary MHC Class I HLA-C molecules to which the survivin peptide, survivin peptide variant, or survivin peptide functional equivalent may bind include, without limitation, HLA-C1, HLA-C2, HLA-C3, HLA-C4, HLA-C5, HLA-C6, HLA-C7 and HLA-C16.

In a particular embodiment, a composition as disclosed herein may comprise one or more of the survivin peptide antigens selected from:

| | | |
|---|---|---|
| i) | FEELTLGEF [HLA-A1] | (SEQ ID NO: 70) |
| ii) | FTELTLGEF [HLA-A1] | (SEQ ID NO: 71) |
| iii) | LTLGEFLKL [HLA-A2] | (SEQ ID NO: 72) |
| iv) | LMLGEFLKL [HLA-A2] | (SEQ ID NO: 73) |
| v) | RISTFKNWPF [HLA-A3] | (SEQ ID NO: 74) |
| vi) | RISTFKNWPK [HLA-A3] | (SEQ ID NO: 75) |
| vii) | STFKNWPFL [HLA-A24] | (SEQ ID NO: 76) |
| viii) | LPPAWQPFL [HLA-B7] | (SEQ ID NO: 77) |

The above-listed survivin peptides represent, without limitation, exemplary MHC Class I restricted peptides encompassed by the present disclosure. The specific MHC Class I HLA molecule to which each of the survivin peptides is believed to bind is shown on the right in square brackets. A composition as disclosed herein may comprise one or more of these survivin peptides, in any suitable combination.

In a further embodiment, a composition as disclosed herein may comprise any one or more of the five survivin peptides listed below, in any suitable combination:

| | | |
|---|---|---|
| i) | FTELTLGEF [HLA-A1] | (SEQ ID NO: 71) |
| ii) | LMLGEFLKL [HLA-A2] | (SEQ ID NO: 73) |
| iii) | RISTFKNWPK [HLA-A3] | (SEQ ID NO: 75) |
| iv) | STFKNWPFL [HLA-A24] | (SEQ ID NO: 76) |
| v) | LPPAWQPFL [HLA-B7] | (SEQ ID NO: 77) |

In a particular embodiment, the composition as disclosed herein comprises all five of the survivin peptide antigens listed above.

In some embodiments, in addition to the at least one survivin antigen, a composition as disclosed herein may comprise one or more additional antigens, such as for example those described herein.

CT Epitopes and B Cell Epitopes

As mentioned above, in some embodiments, the antigen is a molecule comprising at least one B cell epitope or CTL epitope.

The epitopes may be of any chemical nature, including without limitation peptides, carbohydrates, lipids, glycopeptides and glycolipids. In particular embodiments, the epitopes are peptides derived from any of the antigens described herein. The epitope may be identical to a naturally occurring epitope, or may be a modified form of a naturally occurring epitope.

B cell epitopes are epitopes recognized by B cells and by antibodies. B cell peptide epitopes are typically at least five amino acids, more often at least six amino acids, still more often at least seven or eight amino acids in length, and may be continuous ("linear") or discontinuous ("conformational"); the latter being formed, for example, by the folding of a protein to bring non-contiguous parts of the primary amino acid sequence into physical proximity. B cell epitopes may also be carbohydrate epitopes.

In an embodiment, the antigen of the compositions described herein may be or comprise a B cell epitope capable of inducing a humoral immune response.

In some embodiments, the antigen of the compositions described herein may be or comprise a B cell epitope associated with an infectious disease. For example, the antigen may be or comprise a B cell epitope derived from a virus, such as for example influenza virus or respiratory syncytial virus. In another embodiment, the B cell epitope may be an epitope derived from the hemagglutinin glycoprotein of the H5N1 influenza virus.

In another embodiment, the antigen of the compositions described herein may be or comprise a B cell epitope derived from a bacterium, such as for example *Bordetella pertussis* or *Bacillus anthracis*. In a particular embodiment, the B cell epitope may be an epitope of the pertussis toxoid protein produced by *Bordetella pertussis*. In another particular embodiment, the B cell epitope may be an epitope of the anthrax recombinant protective antigen (rPA) or the anthrax mutant recombinant protective antigen (mrPA).

In another embodiment, the antigen of the compositions described herein may be or comprise a B cell epitope derived from a protozoan, such as from the genus *Plasmodium*.

In a further embodiment, the composition may comprise a mixture of B cell epitopes as antigens for inducing a humoral immune response. The B cell epitopes may be linked to form a single polypeptide.

CTL epitopes are molecules recognized by cytotoxic T lymphocytes. CTL epitopes are typically presented on the surface of an antigen-presenting cell, complexed with MHC molecules. As used herein, the term "CTL epitope" refers to a molecule (e.g. peptide) which is substantially the same as a natural CTL epitope of an antigen (including a hapten). The CTL epitope may be modified as compared to its natural counterpart, such as by one or two amino acids. Unless otherwise stated, reference herein to a CTL epitope is to an unbound molecule that is capable of being taken up by cells and presented on the surface of an antigen-presenting cell.

The CTL epitope should typically be one that is amendable to recognition by T cell receptors so that a cell-mediated immune response can occur. For peptides, CTL epitopes may interact with class I or class II MHC molecules. CTL epitopes presented by MHC class I molecules are typically peptides between 8 and 15 amino acids in length, and more often between 9 and 11 amino acids in length. CTL epitopes presented by MHC class II molecules are typically peptides between 5 and 24 amino acids in length, and more often between 13 and 17 amino acids in length. If the antigen is larger than these sizes, it will be processed by the immune system into fragments of a size more suitable for interaction with MHC class I or II molecules. Therefore, CTL epitopes may be part of larger peptide than those mentioned above.

Many CTL epitopes are known. Several techniques of identifying additional CTL epitopes are recognized by the art. In general, these involve preparing a molecule which potentially provides a CTL epitope and characterizing the immune response to that molecule.

In an embodiment, the antigen of the compositions described herein may be or comprise a CTL epitope capable of inducing a CTL response. For example, the antigen may be a CTL epitope derived from a virus, such as HPV.

In another embodiment, the antigen may be or comprise a CTL epitope derived from the E6 or E7 protein of HPV. For example, and without limitation, the CTL epitope of E6 protein of HPV may comprise the peptide sequence TIHDIILECV (T10V; SEQ ID NO: 60) and the CTL epitope of the E7 protein of HPV may comprise the peptide sequence RAHYNIVTF (R9F; SEQ ID NO: 2), YMLDLQPETT (Y10T; SEQ ID NO: 61), LLMGTLGIV (L9V; SEQ ID NO: 62), and TLGIVCPI (T8I; SEQ ID NO: 63).

In another embodiment, the CTL epitope may be an epitope of a tumor-associated protein, such as for example, one or more of the survivin peptides described herein or a melanoma-associated protein. In an embodiment, the melanoma-associated protein may be a tyrosine related protein-2 (TRP-2) or p53, which can be obtained by various methods including recombinant technology or chemical synthesis.

For example, and without limitation, the CTL epitope of a TRP-2 derived protein may comprise the peptide sequence SVYDFFVWL (S9L; SEQ ID NO: 56) or VYDFFVWL (V8L; SEQ ID NO: 64). The CTL epitope of a p53 derived protein may comprise, for example, the peptide sequence KYMCNSSCM (K9M; wild type p53; SEQ ID NO: 65), KYICNSSCM (mK9M; modified p53; SEQ ID NO: 66) or AKXVAAWTLKAAAKYICNSSCM (mK9M; SEQ ID NO: 67).

In a further embodiment, the composition may comprise a mixture of CTL epitopes as antigens for inducing a CTL response. The CTL epitopes may be linked to form a single polypeptide.

In some embodiments, the B cell and CTL epitopes are disease-associated and/or disease-specific epitopes. Such diseases include, but are not limited to, any of those described earlier herein. For example, and without limitation, the disease may be a cancer (such as, for example, breast cancer, ovarian cancer, prostate cancer, glioblastoma or diffuse large B cell lymphoma), an infectious disease (such as, for example, a disease caused by or associated with human papillomavirus (HPV) infection, respiratory syncytial virus (RSV) infection, influenza virus infection, Ebola virus infection, *Bacillus anthracis* infection, or *Plasmodium malariae* infection) or an addiction disease (such as, for example, addiction to cocaine).

Other Components

The compositions disclosed herein may further comprise one or more additional components as are known in the art (see e.g. Remington's Pharmaceutical Sciences (Remington's Pharmaceutical Sciences, Mack Publishing Company, Easton, Pa., USA 1985; and The United States Pharmacopoeia: The National Formulary (USP 24 NF19) published in 1999), so long as the composition remains water-free or substantially free of water.

In some embodiments, the vaccine compositions may additionally comprise a T-helper epitope, an emulsifier and/or an excipient.

T-Helper Epitopes

In some embodiments, the compositions disclosed herein may also comprise at least one T-helper epitope or T-helper antigen.

T-helper epitopes are a sequence of amino acids (natural or non-natural amino acids) that have T-helper activity. T-helper epitopes are recognised by T-helper lymphocytes, which play an important role in establishing and maximising the capabilities of the immune system, and are involved in activating and directing other immune cells, such as for example cytotoxic T lymphocytes.

A T-helper epitope can consist of a continuous or discontinuous epitope. Hence not every amino acid of a T-helper is necessarily part of the epitope. Accordingly, T-helper epitopes, including analogs and segments of T-helper epitopes, are capable of enhancing or stimulating an immune response. Immunodominant T-helper epitopes are broadly reactive in animal and human populations with widely divergent MHC types (Celis et al. (1988) *J. Immunol.* 140:1808-1815; Demotz et al. (1989) *J. Immunol.* 142:394-402; Chong et al. (1992) *Infect. Immun.* 60:4640-4647). The T-helper domain of the subject peptides may have from about 10 to about 50 amino acids, and more particularly about 10 to about 30 amino acids. When multiple T-helper epitopes are present, then each T-helper epitope acts independently.

In some embodiments, the T-helper epitope may form part of an antigen described herein. In particular, if the antigen is of sufficient size, it may contain an epitope that functions as a T-helper epitope. In other embodiments, the T-helper epitope is a separate molecule from the antigen.

In another embodiment, T-helper epitope analogs may include substitutions, deletions and insertions of from one to about 10 amino acid residues in the T-helper epitope. T-helper segments are contiguous portions of a T-helper epitope that are sufficient to enhance or stimulate an immune response. An example of T-helper segments is a series of overlapping peptides that are derived from a single longer peptide.

In a particular embodiment, the compositions as disclosed herein may comprise as a T-helper epitope or antigen, the modified Tetanus toxin peptide A16L (830 to 844; AQYIKANSKFIGITEL (SEQ ID NO: 78), with an alanine residue added to its amino terminus to enhance stability (Slingluff et al., Clin Cancer Res., 7: 3012-3024, 2001).

Other sources of T-helper epitopes which may be used in the present compositions include, for example, hepatitis B surface antigen helper T cell epitopes, pertussis toxin helper T cell epitopes, measles virus F protein helper T cell epitope, *Chlamydia trachomitis* major outer membrane protein helper T cell epitope, diphtheria toxin helper T cell epitopes, *Plasmodium falciparum* circumsporozoite helper T cell epitopes, *Schistosoma mansoni* triose phosphate isomerase helper T cell epitopes, *Escherichia coli* TraT helper T cell epitopes and immune-enhancing analogs and segments of any of these T-helper epitopes.

In some embodiments, the T-helper epitope may be a universal T-helper epitope. A universal T-helper epitope as used herein refers to a peptide or other immunogenic molecule, or a fragment thereof, that binds to a multiplicity of MHC class II molecules in a manner that activates T cell function in a class II (CD4+ T cells)-restricted manner. An example of a universal T-helper epitope is PADRE (pan-DR epitope) comprising the peptide sequence AKXVAAWTLKAAA (SEQ ID NO: 79), wherein X may be cyclohexylalanyl. PADRE specifically has a CD4+ T-helper epitope, that is, it stimulates induction of a PADRE-specific CD4+ T-helper response.

In addition to the modified tetanus toxin peptide A16L mentioned earlier, Tetanus toxoid has other T-helper epitopes that work in the similar manner as PADRE. Tetanus and diphtheria toxins have universal epitopes for human CD4+ cells (Diethelm-Okita, B. M. et al., *J. Infect. Diseases*, 181:1001-1009, 2000). In another embodiment, the T-helper epitope may be a tetanus toxoid peptide such as F21E comprising the peptide sequence FNNFTVSFWLRVPKVSASHLE (amino acids 947-967; SEQ ID NO: 80).

In certain embodiments, the T-helper epitope is fused to at least one of the one or more antigens in the composition as disclosed herein (e.g. a fusion peptide).

Emulsifiers

In some embodiments, the vaccine compositions disclosed herein may comprise one or more emulsifiers. The emulsifier may be a pure emulsifying agent or a mixture of emulsifying agents. The emulsifier(s) should be pharmaceutically and/or immunologically acceptable.

The use of an emulsifier may be of particular relevance to preparing compositions that are water-free or substantially free of water. For instance, in some embodiments an emulsifier may be used to assist in stabilizing the amphipathic compound, mixture of amphipathic compound and antigen, or the mixture of amphipathic compound, antigen and other vaccine components (e.g. polyI:C and/or lipid-based adjuvant, T-helper epitope, etc.) when the amphipathic compound or mixtures are resuspended into the hydrophobic carrier. The use of an emulsifier may, for example, promote more even distribution of the amphipathic compound or mixture in the hydrophobic carrier.

The emulsifier may be amphipathic and therefore, the emulsifier may include a broad range of compounds. In some embodiments, the emulsifier may be a surfactant, such as for example, a non-ionic surfactant. Examples of emulsifiers which may be used include polysorbates, which are oily liquids derived from polyethylene glycolyated sorbital, and sorbitan esters. Polysorbates may include, for example, sorbitan monooleate. Typical emulsifiers are well-known in the art and include, without limitation, mannide oleate (Arlacel™ A), lecithin, Tween™ 80, Spans™ 20, 80, 83 and 85. In an embodiment, the emulsifier for use in the vaccine compositions is mannide oleate.

The emulsifier is generally pre-mixed with the hydrophobic carrier. In some embodiments, a hydrophobic carrier which already contains an emulsifier may be used. For example, a hydrophobic carrier such MONTANIDE™ ISA 51 already contains the emulsifier mannide oleate. In other embodiments, the hydrophobic carrier may be mixed with emulsifier before combining with the amphipathic compound, mixture of amphipathic compound and antigen, or the mixture of amphipathic compound, antigen and other vaccine components (e.g. polyI:C and/or lipid-based adjuvant, T-helper epitope, etc.).

The emulsifier is used in an amount effective to promote even distribution of the amphipathic compound in the hydrophobic carrier and/or to assist in the formation of structures, assemblies or arrays described herein. Typically, the volume ratio (v/v) of hydrophobic carrier to emulsifier is in the range of about 5:1 to about 15:1, more particularly 10:1.

Water-Free Nature of the Compositions

The adjuvanting system disclosed herein is designed for the preparation of vaccine compositions that are water-free or substantially free of water, i.e. the vaccine compositions are not emulsions.

By "water-free" it is meant that the compositions contain no water at all. In another embodiment, the compositions may be substantially free of water. The term "substantially free of water" is intended to encompass embodiments where the hydrophobic carrier may still contain small quantities of water, provided that the water is present in the non-continuous phase of the carrier. For example, individual components of the composition may have small quantities of bound water that may not be completely removed by processes such as lyophilization or evaporation and certain hydrophobic carriers may contain small amounts of water dissolved therein. Generally, compositions as disclosed herein that are "substantially free of water" contain, for example, less than about 10%, 9%, 8%, 7%, 6%, 5%, 4%, 3%, 2%, 1%, 0.5%, 0.1%, 0.05% or 0.01% water on a weight/weight basis of the total weight of the carrier component of the composition. The compositions that still contain small quantities of water do not contain a sufficient amount of water such that an emulsion would be formed.

As demonstrated herein, it has been surprisingly and unexpectedly found that water-free vaccine compositions comprising the adjuvanting system disclosed herein are capable of generating significantly higher antibody titres and more potent cell-mediated immune responses with lower doses of the polyI:C and lipid-based adjuvants.

Thus, in an embodiment, the water-free vaccine compositions disclosed herein comprise a low per unit dose amount of the polyI:C polynucleotide adjuvant and the lipid-based adjuvant, as described above herein.

In some embodiments of the water-free compositions disclosed herein, the low per unit dose amount is capable of providing an enhanced immunogenicity as compared to an identical control composition that comprises a higher per unit dose amount of the polyI:C polynucleotide adjuvant and the lipid-based adjuvant. In some embodiments, the water-free composition disclosed herein induces an antibody immune response that is at least about 2 times, 3 times, 4 times, 5 times, 6 times, 7 times, 8 times, 9 times or 10 times higher than the as defined identical control composition. In a particular embodiment, the water-free composition disclosed herein induces an antibody immune response that is about 6.5 times higher than the as defined identical control composition.

In some embodiments of the water-free compositions disclosed herein, the low per unit dose amount is capable of providing an enhanced immunogenicity as compared to an identical control composition that comprises an equivalent per unit dose amount or a higher per unit dose amount of the polyI:C polynucleotide adjuvant and the lipid-based adjuvant, does not comprise the amphipathic compound, and is formulated as an oil emulsion composition. In some embodiments, the water-free composition disclosed herein induces an antibody immune response that is at least equivalent to or at least 1.5 times, 2 times, 3 times, 4 times, 5 times, 6 times, 7 times, 8 times, 9 times or 10 times higher than the as defined identical control composition and/or a cellular immune response that is at least 1.5 times, 2 times, 2.5 times, 3 times, 3.5 times, 4 times, 4.5 times or 5 times higher than the identical control composition. In a particular embodiment, the water-free composition disclosed herein induces an antibody immune response that is about 2 times higher than the as defined identical control composition. In a particular embodiment, the water-free composition disclosed herein induces a cellular immune response that is about 2-3 times higher than the as defined identical control composition.

In some embodiments, the higher per unit dose amount may be at least about 2-fold, 3-fold, 4-fold, 5-fold, 10-fold, 15-fold, 20-fold or 50-fold greater than the low per unit dose amount.

In some embodiments, the higher per unit dose amount of the polyI:C polynucleotide adjuvant and lipid-based adjuvant is at least about 10 micrograms, about 15 micrograms, about 20 micrograms or more of each per dose, as calculated in mice, or an equivalent translated per unit dose for humans. The translated high per unit dose amount in humans may, for example, be about 200 micrograms or more per unit dose.

In some embodiments, the low per unit dose amount of the polyI:C polynucleotide adjuvant and lipid-based adjuvant is about 0.2 micrograms, about 0.5 micrograms, about 1 microgram, about 5 micrograms or less of each per dose, as calculated in mice, or an equivalent translated per unit dose for humans. As described earlier herein, in some embodiments, the translated low dose amount in humans may be between 2-50 micrograms, for example about 2, 3, 4, 5, 10, 15, 20, 25, 30, 35, 40, 40 or 50 micrograms per unit dose.

In some embodiments, the low per unit dose amount is capable of inducing an antigen-specific antibody immune response at a non-logged antibody titer of at least about 15 million, 20 million, 25 million, 30 million or 35 million by about twelve weeks post-vaccination of a subject. In a particular embodiment, the low per unit dose amount is capable of inducing an antigen-specific antibody immune response at a non-logged antibody titer of between about 29-30 million by about twelve weeks post-vaccination of a subject.

Without being held to any particular theory of action, it is thought that when a water-free composition of the present disclosure is used, the formulation creates a strong depot that persists over several weeks allowing prolonged clearance of antigen and interaction of the vaccine with the immune system. In this regard, it has been reported that lipid-in-oil based formulations achieve peak clearance within 3 weeks of immunization, and clearance continues at a slower rate over six months (Brewer et al. 2014). This is in contrast to aqueous vaccine formulations which release antigens quickly over a few hours to a week; or emulsions which form a short-lived depot.

As described earlier, it is thought that timing is key to the effectiveness of TLR agonists, as pre-exposure to one TLR agonist may result in tolerance to others. The water-free vaccine compositions disclosed herein may be particularly well-suited to achieve simultaneous exposure by promoting a strong depot effect that retains vaccine components (e.g. adjuvant and antigen) at the injection site for extended latencies.

Moreover, as described earlier, the expression of receptors for polyI:C on a wide variety of cells has limited the use of polyI:C as an adjuvant. However, it is surprisingly demonstrated herein that the water-free vaccine compositions are capable of generating strong antibody and cell-mediated immune responses with a significantly reduced dose of the polyI:C adjuvant (e.g. a 20-fold reduction). This may represent a significant advantage as the use of lower per unit dose amounts of polyI:C may reduce systemic exposure. Likewise, the strong depot effect created by the water-free compositions may also limit systemic exposure.

Kits and Reagents

The adjuvanting system or vaccine compositions disclosed herein are optionally provided to a user as a kit. For example, a kit of the present disclosure contains one or more components of the adjuvanting system or compositions disclosed herein. The kit can further comprise one or more additional reagents, packaging material, containers for holding the components of the kit, and an instruction set or user manual detailing preferred methods of using the kit components. In an embodiment, the containers are vials.

In one aspect, disclosed herein is a kit comprising, in one or more separate containers, a polyI:C polynucleotide adjuvant; a lipid-based adjuvant; an amphipathic compound; and a hydrophobic carrier. The kit may take any number of suitable forms.

In a first embodiment of the kit, the polyI:C polynucleotide adjuvant; the lipid-based adjuvant; the amphipathic compound; and the hydrophobic carrier are each provided in a separate container.

In a second embodiment of the kit, the polyI:C polynucleotide adjuvant; the lipid-based adjuvant; and the amphipathic compound are provided together in a first container and the hydrophobic carrier is provided in a second container. In this embodiment, the components of the first container may be in the form of a lyophilized dry cake, and a water-free vaccine composition can be prepared, e.g. just prior to injection, by resuspending the contents of the first container with an antigen and the hydrophobic carrier from the second container.

In a third embodiment of the kit, the polyI:C polynucleotide adjuvant and the lipid-based adjuvant are provided together in a first container; the amphipathic compound is provided in a second container; and the hydrophobic carrier is provided in a third container.

In a fourth embodiment of the kit, the polyI:C polynucleotide adjuvant and the lipid-based adjuvant are provided together in a first container and the amphipathic compound and the hydrophobic carrier are provided together in a second container.

In a fifth embodiment of the kit, the polyI:C polynucleotide adjuvant is provided in a first container, the lipid-based adjuvant is provided in a second container, and the amphipathic compound and the hydrophobic carrier are provided together in a third container.

In a sixth embodiment of the kit, the polyI:C polynucleotide, the lipid-based adjuvant, the amphipathic compound and the hydrophobic carrier are all provided together in a single container.

In another aspect, the kit as described herein may additionally comprise an antigen as described herein. In one embodiment, the antigen may be provided together in the container with any one or more of the polyI:C polynucleotide adjuvant, the lipid-based adjuvant, the amphipathic compound, the hydrophobic carrier, and/or any mixture thereof. In another embodiment, the antigen may be provided in a separate container.

In a particular embodiment, the polyI:C polynucleotide, the lipid-based adjuvant, the amphipathic compound and the antigen are provided together in a first container as a lyophilized dry cake, and the hydrophobic carrier is provided together in a second container. In this embodiment, a water-free vaccine composition can be prepared, e.g. just prior to injection, by resuspending the contents of the first container in the hydrophobic carrier from the second container.

In another aspect, the kit as described herein may additionally comprise a T-helper epitope as described herein. In one embodiment, the T-helper epitope may be provided together in the container with any one or more of the polyI:C polynucleotide adjuvant, the lipid-based adjuvant, the amphipathic compound, the hydrophobic carrier, the antigen and/or any mixture thereof. In another embodiment, the T helper may be provided in a separate container.

The kit as described herein may further comprise instructions for use in preparing a vaccine composition, and in particular a vaccine composition that is water-free or substantially free of water. In some embodiments, the kit may further comprise instructions for use in inducing an antibody response and/or cell-mediated immune response in a subject.

In a particular embodiment of the kit described herein, the lipid-based adjuvant is $PAM_3Cys$-Ser-(Lys)4 (SEQ ID NO: 1); the polyI:C polynucleotide adjuvant is a mixture of varying strand lengths of polyI and polyC, said mixture comprising an approximate molecular weight of 989,486 Daltons; the amphipathic compound is a mixture of S100 lipids and cholesterol or a mixture of dioleoyl phosphatidylcholine (DOPC) and cholesterol; and the hydrophobic carrier is a mannide oleate in mineral oil solution (e.g. MONTANIDE™ ISA51)VG.

In any of the above embodiments, the adjuvants, antigen, and/or T-helper may be in solution, ready to be mixed and lyophilized before reconstitution in the hydrophobic carrier; or may already be lyophilized and ready for reconstitution in the hydrophobic carrier. In either embodiment, reconstitution in the hydrophobic carrier provides a vaccine composition that is water-free or substantially free of water.

Immune Responses and Methods of Use

The adjuvanting system and compositions disclosed herein may find application in any instance in which it is desired to administer an antigen to a subject. The subject may be a vertebrate, such as a fish, bird or mammal, preferably a human.

As referred to herein, the "immune response" may either be a cell-mediated immune response or an antibody (humoral) immune response.

In some embodiments, the vaccine compositions disclosed herein may be used for inducing a cell-mediated immune response.

As used herein, to "induce" an immune response is to elicit and/or potentiate an immune response. Inducing an immune response encompasses instances where the immune response is enhanced, elevated, improved or strengthened to the benefit of the host relative to the prior immune response status, for example, before the administration of a composition disclosed herein.

As used herein, the terms "cell-mediated immune response", "cellular immunity", "cellular immune response" or "cytotoxic T-lymphocyte (CTL) immune response" (used interchangeably herein) refer to an immune response characterized by the activation of macrophages and natural killer cells, the production of antigen-specific cytotoxic T lymphocytes and/or the release of various cytokines in response to an antigen. Cytotoxic T lymphocytes are a sub-group of T lymphocytes (a type of white blood cell) which are capable of inducing the death of infected somatic or tumor cells; they kill cells that are infected with viruses (or other pathogens), or that are otherwise damaged or dysfunctional.

Most cytotoxic T cells express T cell receptors that can recognise a specific peptide antigen bound to Class I MHC molecules. Typically, cytotoxic T cells also express CD8 (i.e. CD8+ T cells), which is attracted to portions of the Class I MHC molecule. This affinity keeps the cytotoxic T cell and the target cell bound closely together during antigen-specific activation.

Cellular immunity protects the body by, for example, activating antigen-specific cytotoxic T-lymphocytes (e.g. antigen-specific CD8+ T cells) that are able to lyse body cells displaying epitopes of foreign antigen on their surface, such as virus-infected cells, cells with intracellular bacteria, and cancer cells displaying tumor antigens; activating macrophages and natural killer cells, enabling them to destroy intracellular pathogens; and stimulating cells to secrete a variety of cytokines that influence the function of other cells involved in adaptive immune responses and innate immune responses.

Cellular immunity is an important component of the adaptive immune response and following recognition of antigen by cells through their interaction with antigen-presenting cells such as dendritic cells, B lymphocytes and to a lesser extent, macrophages, protects the body by various mechanisms such as:

1. activating antigen-specific cytotoxic T-lymphocytes that are able to induce apoptosis in body cells displaying epitopes of foreign antigen on their surface, such as virus-infected cells, cells with intracellular bacteria, and cancer cells displaying tumor antigens;

2. activating macrophages and natural killer cells, enabling them to destroy intracellular pathogens; and 3. stimulating cells to secrete a variety of cytokines that influence the function of other cells involved in adaptive immune responses and innate immune responses.

Cell-mediated immunity is most effective in removing virus-infected cells, but also participates in defending against fungi, protozoans, cancers, and intracellular bacteria. It also plays a major role in transplant rejection.

Since cell-mediated immunity involves the participation of various cell types and is mediated by different mechanisms, several methods could be used to demonstrate the induction of immunity following vaccination. These could be broadly classified into detection of: i) specific antigen presenting cells; ii) specific effector cells and their functions and iii) release of soluble mediators such as cytokines.

i) Antigen presenting cells: Dendritic cells and B cells (and to a lesser extent macrophages) are equipped with special immunostimulatory receptors that allow for enhanced activation of T cells, and are termed professional antigen presenting cells (APC). These immunostimulatory molecules (also called co-stimulatory molecules) are up-regulated on these cells following infection or vaccination, during the process of antigen presentation to effector cells such as CD4 and CD8 cytotoxic T cells. Such co-stimulatory molecules (such as CD40, CD80, CD86, MHC class I or MHC class II) can be detected, for example, by using flow cytometry with fluorochrome-conjugated antibodies directed against these molecules along with antibodies that specifically identify APC (such as CD11c for dendritic cells).

ii) Cytotoxic T cells: (also known as Tc, killer T cell, or cytotoxic T-lymphocyte (CTL)) are a sub-group of T cells which induce the death of cells that are infected with viruses (and other pathogens), or expressing tumor antigens. These CTLs directly attack other cells carrying certain foreign or abnormal molecules on their surface. The ability of such cellular cytotoxicity can be detected using in vitro cytolytic assays (chromium release assay). Thus, induction of adaptive cellular immunity can be demonstrated by the presence of such cytotoxic T cells, wherein, when antigen loaded target cells are lysed by specific CTLs that are generated in vivo following vaccination or infection.

Naive cytotoxic T cells are activated when their T cell receptor (TCR) strongly interacts with a peptide-bound MHC class I molecule. This affinity depends on the type and orientation of the antigen/MHC complex, and is what keeps the CTL and infected cell bound together. Once activated the CTL undergoes a process called clonal expansion in which it gains functionality, and divides rapidly, to produce an army of "armed"-effector cells. Activated CTL will then travel throughout the body in search of cells bearing that unique MHC Class I+ peptide. This could be used to identify such CTLs in vitro by using peptide-MHC Class I tetramers in flow cytometric assays.

When exposed to these infected or dysfunctional somatic cells, effector CTL release perforin and granulysin: cytotoxins which form pores in the target cell's plasma membrane, allowing ions and water to flow into the infected cell, and causing it to burst or lyse. CTL release granzyme, a serine protease that enters cells via pores to induce apoptosis (cell death). Release of these molecules from CTL can be used as a measure of successful induction of cell-mediated immune response following vaccination. This can be done by enzyme linked immunosorbant assay (ELISA) or enzyme linked immunospot assay (ELISPOT) where CTLs can be quantitatively measured. Since CTLs are also capable of producing important cytokines such as IFN-γ, quantitative measurement of IFN-γ-producing CD8 cells can be achieved by ELISPOT and by flowcytometric measurement of intracellular IFN-γ in these cells.

CD4+"helper" T cells: CD4+ lymphocytes, or helper T cells, are immune response mediators, and play an important role in establishing and maximizing the capabilities of the adaptive immune response. These cells have no cytotoxic or phagocytic activity; and cannot kill infected cells or clear pathogens, but, in essence "manage" the immune response, by directing other cells to perform these tasks. Two types of effector CD4+ T helper cell responses can be induced by a professional APC, designated Th1 and Th2, each designed to eliminate different types of pathogens.

Helper T cells express T cell receptors (TCR) that recognize antigen bound to Class II MHC molecules. The activation of a naive helper T cell causes it to release cytokines, which influences the activity of many cell types, including the APC that activated it. Helper T cells require a much milder activation stimulus than cytotoxic T cells. Helper T cells can provide extra signals that "help" activate cytotoxic cells. Two types of effector CD4+ T helper cell responses can be induced by a professional APC, designated Th1 and Th2, each designed to eliminate different types of pathogens. The two Th cell populations differ in the pattern of the effector proteins (cytokines) produced. In general, Th1 cells assist the cell-mediated immune response by activation of macrophages and cytotoxic T cells; whereas Th2 cells promote the humoral immune response by stimulation of B cells for conversion into plasma cells and by formation of antibodies. For example, a response regulated by Th1 cells may induce lgG2a and lgG2b in mouse (IgG1 and lgG3 in humans) and favor a cell mediated immune response to an antigen. If the IgG response to an antigen is regulated by Th2 type cells, it may predominantly enhance the production of IgG1 in mouse (lgG2 in humans). The measure of cytokines associated with Th1 or Th2 responses will give a measure of successful vaccination. This can be achieved by specific ELISA designed for Th1-cytokines such as IFN-γ, IL-2, IL-12, TNF-α and others, or Th2-cytokines such as IL-4, IL-5, IL10 among others.

iii) Measurement of cytokines: released from regional lymph nodes gives a good indication of successful immunization. As a result of antigen presentation and maturation of APC and immune effector cells such as CD4 and CD8 T cells, several cytokines are released by lymph node cells. By culturing these LNC in vitro in the presence of antigen, antigen-specific immune response can be detected by measuring release if certain important cytokines such as IFN-γ, IL-2, IL-12, TNF-α and GM-CSF. This could be done by ELISA using culture supernatants and recombinant cytokines as standards.

Successful immunization may be determined in a number of ways known to the skilled person including, but not limited to, hemagglutination inhibition (HAIJ) and serum neutralization inhibition assays to detect functional antibodies; challenge studies, in which vaccinated subjects are challenged with the associated pathogen to determine the efficacy of the vaccination; and the use of fluorescence activated cell sorting (FACS) to determine the population of cells that express a specific cell surface marker, e.g. in the identification of activated or memory lymphocytes. A skilled person may also determine if immunization with a composition as disclosed herein elicited an antibody and/or cell mediated immune response using other known methods. See, for example, Current Protocols in Immunology Coligan et al., ed. (Wiley Interscience, 2007).

In some embodiments, the vaccine compositions disclosed herein may be used for inducing an antibody immune response.

An "antibody immune response" or "humoral immune response" (used interchangeably herein), as opposed to cell-mediated immunity, is mediated by secreted antibodies which are produced in the cells of the B lymphocyte lineage (B cells). Such secreted antibodies bind to antigens, such as for example those on the surfaces of foreign substances, pathogens (e.g. viruses, bacteria, etc.) and/or cancer cells, and flag them for destruction.

As used herein, "humoral immune response" refers to antibody production and may also include, in addition or alternatively, the accessory processes that accompany it, such as for example the generation and/or activation of T-helper 2 (Th2) or T-helper 17 (Th17) cells, cytokine production, isotype switching, affinity maturation and memory cell activation. "Humoral immune response" may also include the effector functions of an antibody, such as for example toxin neutralization, classical complement activation, and promotion of phagocytosis and pathogen elimination. The humoral immune response is often aided by CD4+ Th2 cells and therefore the activation or generation of this cell type may also be indicative of a humoral immune response. The term "humoral immune response" is used interchangeably herein with "antibody response" or "antibody immune response".

An "antibody" is a protein comprising one or more polypeptides substantially or partially encoded by immunoglobulin genes or fragments of immunoglobulin genes. The recognized immunoglobulin genes include the κ, λ, α, γ, δ, ε and μ constant region genes, as well as myriad immunoglobulin variable region genes. Light chains are classified as either κ or λ. Heavy chains are classified as γ, μ, α, δ, or ε, which in turn define the immunoglobulin classes, IgG, IgM, IgA, IgD and IgE, respectively. A typical immunoglobulin (antibody) structural unit comprises a protein containing four polypeptides. Each antibody structural unit is composed of two identical pairs of polypeptide chains, each having one "light" and one "heavy" chain. The N-terminus of each chain defines a variable region primarily responsible for antigen recognition. Antibody structural units (e.g. of the IgA and IgM classes) may also assemble into oligomeric forms with each other and additional polypeptide chains, for example as IgM pentamers in association with the J-chain polypeptide.

Antibodies are the antigen-specific glycoprotein products of a subset of white blood cells called B lymphocytes (B cells). Engagement of antigen with antibody expressed on the surface of B cells can induce an antibody response comprising stimulation of B cells to become activated, to undergo mitosis and to terminally differentiate into plasma cells, which are specialized for synthesis and secretion of antigen-specific antibody.

B cells are the sole producers of antibodies during an immune response and are thus a key element to effective humoral immunity. In addition to producing large amounts of antibodies, B cells also act as antigen-presenting cells and can present antigen to T cells, such as T helper CD4 or cytotoxic CD8+ T cells, thus propagating the immune response. B cells, as well as T cells, are part of the adaptive immune response. During an active immune response, induced for example by either vaccination or natural infection, antigen-specific B cells are activated and clonally expand. During expansion, B cells evolve to have higher affinity for the epitope. Proliferation of B cells can be induced indirectly by activated T-helper cells, and also directly through stimulation of receptors, such as the TLRs.

Antigen presenting cells, such as dendritic cells and B cells, are drawn to vaccination sites and can interact with antigens and adjuvants contained in a vaccine composition. Typically, the adjuvant stimulates the cells to become activated and the antigen provides the blueprint for the target. Different types of adjuvants may provide different stimulation signals to cells. For example, polyI:C (a TLR3 agonist) can activate dendritic cells, but not B cells. Adjuvants such as Pam3Cys, Pam2Cys and FSL-1 are especially adept at activating and initiating proliferation of B cells, which is expected to facilitate the production of an antibody response (Moyle et al., Curr Med Chem, 2008; So., J mmunol, 2012).

A humoral immune response is one of the common mechanisms for effective infectious disease vaccines (e.g. to protect against viral or bacterial invaders). However, a humoral immune response can also be useful for combating cancer. Whereas a cancer vaccine is typically designed to produce a cell-mediated immune response that can recognize and destroy cancer cells, B cell mediated responses may target cancer cells through other mechanisms which may in some instances cooperate with a cytotoxic T cell for maximum benefit. Examples of B cell mediated (e.g. humoral immune response mediated) anti-tumor responses include, without limitation: 1) Antibodies produced by B cells that bind to surface antigens found on tumor cells or other cells that influence tumorigenesis. Such antibodies can, for example. induce killing of target cells through antibody-dependent cell-mediated cytotoxicity (ADCC) or complement fixation, potentially resulting in the release of additional antigens that can be recognized by the immune system; 2) Antibodies that bind to receptors on tumor cells to block their stimulation and in effect neutralize their effects; 3) Antibodies that bind to factors released by or associated with a tumor or tumor-associated cells to modulate a signaling or cellular pathway that supports cancer; and 4) Antibodies that bind to intracellular targets and mediate anti-tumor activity through a currently unknown mechanism.

One method of evaluating an antibody response is to measure the titers of antibodies reactive with a particular antigen. This may be performed using a variety of methods known in the art such as enzyme-linked immunosorbent assay (ELISA) of antibody-containing substances obtained from animals. For example, the titers of serum antibodies which bind to a particular antigen may be determined in a subject both before and after exposure to the antigen. A statistically significant increase in the titer of antigen-specific antibodies following exposure to the antigen would indicate the subject had mounted an antibody response to the antigen.

Without limitation, other assays that may be used to detect the presence of an antigen-specific antibody include immunological assays (e.g. radioimmunoassay (RIA)), immunoprecipitation assays, and protein blot (e.g. Western blot) assays; and neutralization assays (e.g., neutralization of viral infectivity in an in vitro or in vivo assay).

The vaccine compositions disclosed herein may be useful for treating or preventing diseases and/or disorders ameliorated by a cell-mediated immune response or a humoral immune response. The vaccines may find application in any instance in which it is desired to administer an antigen to a subject to induce a cell-mediated immune response or a humoral immune response.

In an embodiment, the present disclosure relates to a method comprising administering the composition as described herein to a subject in need thereof. In some embodiments, the method is for inducing an antibody response and/or cell-mediated immune response to said antigen in said subject. In some embodiments, the method is for the treatment and/or prevention of a disease caused by a bacteria, a virus, a fungus, a parasite, an allergen, or a tumor cell that expresses the antigen.

"Treating" or "treatment of", or "preventing" or "prevention of", as used herein, refers to an approach for obtaining beneficial or desired results. Beneficial or desired results can include, but are not limited to, alleviation or amelioration of one or more symptoms or conditions, diminishment of extent of disease, stabilisation of the state of disease, prevention of development of disease, prevention of spread of disease, delay or slowing of disease progression (e.g. suppression), delay or slowing of disease onset, conferring protective immunity against a disease-causing agent and amelioration or palliation of the disease state. "Treating" or "preventing" can also mean prolonging survival of a patient beyond that expected in the absence of treatment and can also mean inhibiting the progression of disease temporarily or preventing the occurrence of disease, such as by preventing infection in a subject. "Treating" or "preventing" may also refer to a reduction in the size of a tumor mass, reduction in tumor aggressiveness, etc.

"Treating" may be distinguished from "preventing" in that "treating" typically occurs in a subject who already has a disease or disorder, or is known to have already been exposed to an infectious agent, whereas "preventing" typically occurs in a subject who does not have a disease or disorder, or is not known to have been exposed to an infectious agent. As will be appreciated, there may be overlap in treatment and prevention. For example, it is possible to be "treating" a disease in a subject, while at same time "preventing" symptoms or progression of the disease. Moreover, at least in the context of vaccination, "treating" and "preventing" may overlap in that the treatment of a subject is to induce an immune response that may have the subsequent effect of preventing infection by a pathogen or preventing the underlying disease or symptoms caused by infection with the pathogen. These preventive aspects are encompassed herein by expressions such as "treatment of an infectious disease" or "treatment of cancer".

In an embodiment, the methods and compositions disclosed herein may be for use in treating and/or preventing cancer in a subject in need thereof. The subject may have cancer or may be at risk of developing cancer.

As used herein, the terms "cancer", "cancer cells", "tumor" and "tumor cells", (used interchangeably) refer to cells that exhibit abnormal growth, characterized by a significant loss of control of cell proliferation or cells that have been immortalized. The term "cancer" or "tumor" includes metastatic as well as non-metastatic cancer or tumors. A cancer may be diagnosed using criteria generally accepted in the art, including the presence of a malignant tumor.

Without limitation, cancers that may be capable of being treated and/or prevented by the use or administration of a composition as disclosed herein include carcinoma, adenocarcinoma, lymphoma, leukemia, sarcoma, blastoma, myeloma, and germ cell tumors. Without limitation, particularly suitable embodiments may include glioblastoma, multiple myeloma, ovarian cancer, breast cancer, fallopian tube cancer, prostate cancer or peritoneal cancer. In one embodiment, the cancer may be caused by a pathogen, such as a virus. Viruses linked to the development of cancer are known to the skilled person and include, but are not limited to, human papillomaviruses (HPV), John Cunningham virus (JCV), Human herpes virus 8, Epstein Barr Virus (EBV), Merkel cell polyomavirus, Hepatitis C Virus and Human T cell leukaemia virus-1. In another embodiment, the cancer may be one that expresses one or more cancer-specific antigens (e.g. survivin).

In a particular embodiment, the cancer is breast cancer, ovarian cancer, prostate cancer, fallopian tube cancer, peritoneal cancer, glioblastoma or diffuse large B cell lymphoma.

The methods and compositions disclosed herein may be useful for either the treatment or prophylaxis of cancer; for example, a reduction of the severity of cancer (e.g. size of the tumor, aggressiveness and/or invasiveness, malignancy, etc) or the prevention of cancer recurrences.

In another embodiment, the methods and compositions disclosed herein may be used for treating and/or preventing an infectious disease, such as caused by a viral infection, in a subject in need thereof. The subject may be infected with a virus or may be at risk of developing a viral infection. Viral infections that may be treated and/or prevented by the use or administration of a composition as disclosed herein, without limitation, Cowpoxvirus, Vaccinia virus, Pseudocowpox virus, Human herpesvirus 1, Human herpesvirus 2, Cytomegalovirus, Human adenovirus A-F, Polyomavirus, Human papillomavirus (HPV), Parvovirus, Hepatitis A virus, Hepatitis B virus, Hepatitis C virus, Human immunodeficiency virus, Orthoreovirus, Rotavirus, Ebola virus, parainfluenza virus, influenza A virus, influenza B virus, influenza C virus, Measles virus, Mumps virus, Rubella virus, Pneumovirus, Human respiratory syncytial virus, Rabies virus, California encephalitis virus, Japanese encephalitis virus, Hantaan virus, Lymphocytic choriomeningitis virus, Coronavirus, Enterovirus, Rhinovirus, Poliovirus, Norovirus, Flavivirus, Dengue virus, West Nile virus, Yellow fever virus and varicella. In a particular embodiment, the viral infection is Human papillomavirus, Ebola virus, Human respiratory syncytial virus or an influenza virus.

In another embodiment, the methods or compositions disclosed herein may be used for treating and/or preventing an infectious disease, such as caused by a non-viral pathogen (such as a bacterium or protozoan) in a subject in need thereof. The subject may be infected with the pathogen or may be at risk of developing an infection by the pathogen. Without limitation, exemplary bacterial pathogens may include Anthrax (*Bacillus anthracis*), Brucella, Bordetella pertussis, Candida, Chlamydia pneumoniae, Chlamydia psittaci, Cholera, Clostridium botulinum, Coccidioides immitis, Cryptococcus, Diphtheria, *Escherichia coli* O157:H7, Enterohemorrhagic *Escherichia coli*, Enterotoxigenic *Escherichia coli, Haemophilus influenzae, Helicobacter pylori, Legionella, Leptospira, Listeria*, Meningococcus, *Mycoplasma pneumoniae, Mycobacterium*, Pertussis, Pneumonia, *Salmonella, Shigella, Staphylococcus, Streptococcus pneumoniae* and *Yersinia enterocolitica*. In a particular embodiment, the bacterial infection is Anthrax. Without limitation, exemplary protozoan pathogens may include those of the genus *Plasmodium* (*Plasmodium falciparum, Plasmodium malariae, Plasmodium vivax, Plasmodium ovale* or *Plasmodium knowlesi*), which cause malaria.

In another embodiment, the methods or compositions disclosed herein may be used for treating and/or preventing a neurodegenerative disease in a subject in need thereof, wherein the neurodegenerative disease is associated with the expression of an antigen. The subject may have a neurodegenerative disease or may be at risk of developing a neurodegenerative disease. Neurodegenerative diseases that may be treated and/or prevented by the methods or compositions disclosed herein include, without limitation, Alzheimer's disease, Parkinson's disease, Huntington's disease, and amyotrophic lateral sclerosis (ALS).

In another embodiment, the methods or compositions disclosed herein may be used for treating and/or preventing an addiction disease (such as, for example, addiction to cocaine).

In another embodiment, the methods or compositions disclosed herein may be used for neutralizing a toxin, virus, bacterium or allergen, with an antibody, said method comprising administering the composition as described herein to a subject. For example, antibodies produced in response to the antigen in the vaccine may neutralize or sequester the toxin, virus, bacterium or allergen. In an embodiment, the toxin is a drug substance such as, for example, cocaine.

Methods for Preparing the Vaccine Compositions

The adjuvanting systems and vaccine compositions may be prepared by known methods in the art having regard to the present disclosure, including the non-limiting methods described in the examples. Exemplary embodiments for preparing the adjuvanting systems and vaccine compositions disclosed herein are described below, without limitation.

As used in this section, the term "antigen" is used generally to describe how an antigen may be formulated in the vaccine compositions of the present disclosure. The term "antigen" encompasses both the singular form "antigen" and the plural "antigens". It is not necessary that all antigens be introduced into the vaccine composition in the same way.

In an embodiment for preparing the vaccine composition, the antigen, adjuvants and optionally other vaccine components (e.g. T-helper epitope) are reconstituted in a suitable solvent together with an amphipathic compound. The vaccine components are then dried to form a dry cake, and the dry cake is resuspended in a hydrophobic carrier. The step of drying may be performed by various means known in the art, such as by freeze-drying, lyophilization, rotary evaporation, evaporation under pressure, etc. Low heat drying that does not compromise the integrity of the components can also be used. Heat can also be used to assist in resuspending the antigen/amphipathic compound mixture.

The "suitable solvent" is one that is suitable for solubilizing the antigen, adjuvants and/or amphipathic compound, and can be determined by the skilled person. In an embodiment, sodium phosphate buffer (0.2M, pH 6.0) or sodium phosphate buffer (0.1M, pH 7.0) may be used. In another embodiment, a polar protic solvent such as an alcohol (e.g tert-butanol, n-butanol, isopropanol, n-propanol, ethanol or methanol), water, acetate buffer, formic acid or chloroform may be used. In some cases, the same solvent can be used to solubilize each of the amphipathic compound, antigen and adjuvants, and the solubilized components are then mixed. Alternatively, the antigen, adjuvants and amphipathic compound may be mixed prior to solubilization, and then solubilized together. In a further alternative, only one or more of the amphipathic compound, antigen or adjuvants are solubilized, and the non-solubilized component(s) are added.

In a particular embodiment, to prepare the vaccine compositions the antigen and adjuvants are reconstituted together or separately in sodium phosphate buffer with S100 lipids and cholesterol (Lipoid, Germany). These vaccine components are then lyophilized to form a dry cake. Just prior to injection, the dry cake is resuspended in ISA51 VG oil (SEPPIC, France) to prepare a water-free oil-based vaccine composition.

In another embodiment, to prepare the vaccine compositions the conjugated antigen/T-helper epitope is reconstituted in 0.2% PEG-H$_2$O with lipids DOPC and cholesterol (Lipoid, Germany). The polyI:C and lipid-based adjuvants are reconstituted in water, and then added to the antigen-lipid mixture. These vaccine components are then lyophilized to form a dry cake. Just prior to injection, the dry cake is resuspended in ISA51 VG oil (SEPPIC, France) to prepare a water-free vaccine composition.

In the above embodiments, without being bound to a particular theory of action, it is believed that removal (drying) of the solvent leaves the vaccine components, including the antigen, in an array of amphipathic compound molecules with their hydrophilic head groups oriented towards the vaccine components. The vaccine components and amphipathic compound can then be suspended in the hydrophobic carrier (such as oil) in the absence of water, since they have been made sufficiently hydrophobic.

Additional components as described herein, such as T-helper epitope, may be added at any stage in the formulation process. For instance, one or more such additional components may be combined with the antigen, adjuvants and/or amphipathic compound either before or after solubilization, or added to the solubilized mixture. In another embodiment, the additional components may instead be added to or combined with the dried mixture of antigen, adjuvants and amphipathic compound, or combined with the hydrophobic carrier either before or after resuspension of the dry mixture of antigen, adjuvants and amphipathic compound in the hydrophobic carrier. In an embodiment, the T-helper epitope is added to the vaccine composition in the same way as the antigen. In an embodiment, the antigen and T-helper epitope are a fused peptide.

In some embodiments, it may be appropriate to include an emulsifier in the hydrophobic carrier to assist in stabilizing the vaccine components of the dry cake when they are resuspended in the hydrophobic carrier. The emulsifier is provided in an amount sufficient to resuspend the dry mixture of antigen, adjuvants and amphipathic compound in the hydrophobic carrier and maintain the antigen, adjuvants and amphipathic compound in suspension in the hydrophobic carrier. For example, the emulsifier may be present at about 5% to about 15% weight/weight or weight/volume of the hydrophobic carrier.

Stabilizers such as sugars, anti-oxidants, or preservatives that maintain the biological activity or improve chemical stability to prolong the shelf life of any of the vaccine components, may be added to such compositions.

The adjuvanting system as disclosed herein may be prepared in similar fashion as described above for the vaccine composition, with the exception that the antigen is excluded. To then prepare a water-free vaccine composition, the antigen may be prepared separately with the amphipathic compound, dried, resuspended with the hydrophobic carrier, and then mixed with the adjuvanting system. Alternatively, the antigen may be added directly to the adjuvanting system, alone or after admixture with an amphipathic compound.

EMBODIMENTS

Particular embodiments of the present disclosure include, without limitation, the following:

(1) An adjuvanting system comprising:
   (a) a polyI:C polynucleotide adjuvant;
   (b) a lipid-based adjuvant;
   (c) an amphipathic compound; and
   (d) a hydrophobic carrier.

(2) The adjuvanting system of paragraph (1), wherein the lipid-based adjuvant comprises one or more lipopeptide(s).

(3) The adjuvanting system of paragraph (2), wherein at least one of the lipopeptides comprises palmitic acid as the lipid component.

(4) The adjuvanting system of any one of paragraphs (1) to (3), wherein the lipid-based adjuvant comprises dipalmitoyl-S-glyceryl-cysteine (PAM$_2$Cys) or tripalmitoyl-S-glyceryl-cysteine (PAM$_3$Cys).

(5) The adjuvanting system of paragraph (4), wherein the lipid-based adjuvant is PAM$_2$Cys-Ser-(Lys)4 (SEQ ID NO: 1) or PAM$_3$Cys-Ser-(Lys)4 (SEQ ID NO: 1).

(6) The adjuvanting system of paragraph (5), wherein the lipid-based adjuvant is PAM$_3$Cys-Ser-(Lys)4 (SEQ ID NO: 1).

(7) The adjuvanting system of any one of paragraphs (1) to (6), wherein the polyI:C polynucleotide adjuvant comprises RNA, DNA or a combination thereof.

(8) The adjuvanting system of any one of paragraphs (1) to (7), wherein the polyI:C polynucleotide adjuvant is double-stranded and each strand is a homopolymer of inosinic or cytidylic residues.

(9) The adjuvanting system of any one of paragraphs (1) to (7), wherein the polyI:C polynucleotide adjuvant is double-stranded and each strand is a heteropolymer comprising both inosinic and cytidylic residues.

(10) The adjuvanting system of any one of paragraphs (1) to (7), wherein the polyI:C polynucleotide adjuvant is a mixture comprising both homopolymeric polyI:C polynucleotides and heteropolymeric polyI:C polynucleotides.

(11) The adjuvanting system of any one of paragraphs (1) to (7), wherein the polyI:C polynucleotide adjuvant is a mixture of varying strand lengths of polyI and polyC, said mixture comprising an approximate molecular weight of 989,486 Daltons.

(12) The adjuvanting system of any one of paragraphs (1) to (11), wherein the amphipathic compound is a lipid.

(13) The adjuvanting system of paragraph (12), wherein the lipids form a closed vesicular structure around the antigen.

(14) The adjuvanting system of paragraph (13), wherein the closed vesicular structure is a single layer vesicular structure or a bilayer vesicular structure.

(15) The adjuvanting system of paragraph (14), wherein the single layer vesicular structure is a micelle.

(16) The adjuvanting system of paragraph (14), wherein the bilayer vesicular structure is a unilamellar or multilamellar liposome.

(17) The adjuvanting system of any one of paragraphs (12) to (16), wherein the lipid is a phospholipid or a mixture of phospholipids.

(18) The adjuvanting system of paragraph (17), wherein the phospholipid is dioleoyl phosphatidylcholine (DOPC) or the mixture of phospholipids comprises DOPC.

(19) The adjuvanting system of paragraph (17), wherein the phospholipid is lecithin or the mixture of phospholipids comprises lecithin.

(20) The adjuvanting system of paragraph (19), wherein the lecithin is Lipoid S100.

(21) The adjuvanting system of any one of paragraphs (1) to (20), wherein the carrier is an oil or a mixture of oils.

(22) The adjuvanting system of paragraph (21), wherein the carrier comprises a vegetable oil, nut oil, or mineral oil.

(23) The adjuvanting system of paragraph (22), wherein the carrier is mineral oil or is a mannide oleate in mineral oil solution.

(24) The adjuvanting system of paragraph (23), wherein the carrier is MONTANIDE® ISA 51 VG.

(25) A composition comprising:
(a) an antigen;
(b) a polyI:C polynucleotide adjuvant;
(c) a lipid-based adjuvant;
(d) an amphipathic compound; and
(e) a hydrophobic carrier,
wherein the composition is water-free or substantially free of water.

(26) The composition of paragraph (25) which is water-free.

(27) The composition of paragraph (25), which comprises less than about 10%, 9%, 8%, 7%, 6%, 5%, 4%, 3%, 2%, 1%, 0.5%, 0.1%, 0.05% or 0.01% water on a weight/weight basis of the total weight of the carrier.

(28) The composition of any one of paragraphs (25) to (27), wherein the lipid-based adjuvant comprises one or more lipopeptide(s).

(29) The composition of paragraph (28), wherein at least one of the lipopeptides comprises palmitic acid as the lipid component.

(30) The composition of any one of paragraphs (25) to (29), wherein the lipid-based adjuvant comprises dipalmitoyl-S-glyceryl-cysteine (PAM$_2$Cys) or tripalmitoyl-S-glyceryl-cysteine (PAM$_3$Cys).

(31) The composition of paragraph (30), wherein the lipid-based adjuvant is PAM$_2$Cys-Ser-(Lys)4 (SEQ ID NO: 1) or PAM$_3$Cys-Ser-(Lys)4 (SEQ ID NO: 1).

(32) The composition of paragraph (31), wherein the lipid-based adjuvant is PAM$_3$Cys-Ser-(Lys)4 (SEQ ID NO: 1).

(33) The composition of any one of paragraphs (25) to (32), wherein the polyI:C polynucleotide adjuvant comprises RNA, DNA or a combination thereof.

(34) The composition of any one of paragraphs (25) to (33), wherein the polyI:C polynucleotide adjuvant is double-stranded and each strand is a homopolymer of inosinic or cytidylic residues.

(35) The composition of any one of paragraphs (25) to (33), wherein the polyI:C polynucleotide adjuvant is double-stranded and each strand is a heteropolymer comprising both inosinic and cytidylic residues.

(36) The composition of any one of paragraphs (25) to (33), wherein the polyI:C polynucleotide adjuvant is a mixture comprising both homopolymeric polyI:C polynucleotides and heteropolymeric polyI:C polynucleotides.

(37) The composition any one of paragraphs (25) to (33), wherein the polyI:C polynucleotide adjuvant is a mixture of varying strand lengths of polyI and polyC, said mixture comprising an approximate molecular weight of 989,486 Daltons.

(38) The composition of any one of paragraphs (25) to (37), wherein the amphipathic compound is a lipid.

(39) The composition of paragraph (38), wherein the lipids form a closed vesicular structure around the antigen.

(40) The composition of paragraph (39), wherein the closed vesicular structure is a single layer vesicular structure or a bilayer vesicular structure.

(41) The composition of paragraph (40), wherein the single layer vesicular structure is a micelle.

(42) The composition of paragraph (40), wherein the bilayer vesicular structure is a unilamellar or multilamellar liposome.

(43) The composition of any one of paragraphs (38) to (42), wherein the lipid is a phospholipid or a mixture of phospholipids.

(44) The composition of paragraph (43), wherein the phospholipid is dioleoyl phosphatidylcholine (DOPC) or the mixture of phospholipids comprises DOPC.

(45) The composition of paragraph (43), wherein the phospholipid is lecithin or the mixture of phospholipids comprises lecithin.

(46) The composition of paragraph (45), wherein the lecithin is Lipoid S100.

(47) The composition of any one of paragraphs (25) to (46), wherein the carrier is an oil or a mixture of oils.

(48) The composition of paragraph (47), wherein the carrier comprises a vegetable oil, nut oil, or mineral oil.

(49) The composition of paragraph (48), wherein the carrier is mineral oil or is a mannide oleate in mineral oil solution.

(50) The composition of paragraph (49), wherein the carrier is MONTANIDE® ISA 51 VG.

(51) The composition of any one of paragraphs (25) to (50), wherein the antigen is a polypeptide; a polynucleotide encoding a polypeptide; a carbohydrate; a microorganism or a part thereof, or a toxin.

(52) The composition of paragraph (51), wherein the antigen is: (i) derived from a virus, bacterium or protozoan; (ii) a membrane surface-bound cancer antigen; or (iii) a toxin.

(53) The composition of paragraph (52), wherein the antigen is derived from Ebola virus, human papillomavirus (HPV), influenza virus, respiratory syncytial virus, *Bordetella pertussis*, *Bacillus anthracis* or *Plasmodium malariae*.

(54) The composition of paragraph (53), wherein the antigen derived from *Bacillus anthracis* is a recombinant protective antigen (PA) derived from anthrax toxin.

(55) The composition of paragraph (53), wherein the antigen derived from HPV comprises the amino acid sequence RAHYNIVTF (SEQ ID NO: 2).

(56) The composition of paragraph (53), wherein the antigen derived from influenza virus is a recombinant HA antigen.

(57) The composition of paragraph (52), wherein the membrane surface-bound cancer antigen is a survivin antigen.

(58) The composition of paragraph (57), wherein the survivin antigen is a peptide antigen comprising an amino acid sequence from the survivin protein (SEQ ID NO: 69) or a modified variant thereof; or a nucleic acid molecule encoding said peptide antigen.

(59) The composition of paragraph (57), wherein the survivin antigen is a peptide antigen comprising an amino acid sequence selected from FEELTLGEF (SEQ ID NO: 70); FTELTLGEF (SEQ ID NO: 71); LTLGEFLKL (SEQ ID NO: 72); LMLGEFLKL (SEQ ID NO: 73); RISTFKNWPF (SEQ ID NO: 74); RISTFKNWPK (SEQ ID NO: 75); STFKNWPFL (SEQ ID NO: 76); or LPPAWQPFL (SEQ ID NO: 77), or any combination thereof; or a nucleic acid molecule encoding said peptide antigen.

(60) The composition of paragraph (57) which comprises a mixture of five peptide antigens comprising the amino acid sequence: FTELTLGEF (SEQ ID NO: 71); LMLGEFLKL (SEQ ID NO: 73); RISTFKNWPK (SEQ ID NO: 75); STFKNWPFL (SEQ ID NO: 76); and LPPAWQPFL (SEQ ID NO: 77).

(61) The composition of paragraph (52), wherein the toxin is a drug substance, for example cocaine.

(62) The composition of any one of paragraphs (25) to (61), wherein the antigen comprises at least one B cell epitope, at least one CTL epitope or a combination thereof.

(63) The composition of any one of paragraphs (25) to (62) further comprising a T-helper epitope.

(64) The composition of paragraph (63), wherein the T-helper epitope is conjugated or fused to the antigen.

(65) The composition of paragraph (62) or (63), wherein the T-helper is PADRE comprising the amino acid sequence AKXVAAWTLKAAA (SEQ ID NO: 79); Tetanus toxoid peptide F21E comprising the amino acid sequence FNNFTVSFWLRVPKVSASHLE (SEQ ID NO: 80); or modified Tetanus toxin peptide A16L comprising the amino acid sequence AQYIKANSKFIGITEL (SEQ ID NO: 78).

(66) The composition of any one of paragraphs (25) to (65), wherein the polyI:C polynucleotide adjuvant is a Toll-like receptor 3 (TLR3) agonist and the lipid-based adjuvant is an agonist of the TLR1/2 heterodimer.

(67) The composition of any one of paragraphs (25) to (66), which is capable of inducing an antibody immune response and/or cell-mediated immune response with a single dose.

(68) The composition of paragraph (67) which comprises a low per unit dose amount of the polyI:C polynucleotide adjuvant and the lipid-based adjuvant.

(69) The composition of paragraph (68), wherein the low per unit dose amount is capable of providing an enhanced immunogenicity as compared to an identical control composition that comprises a higher per unit dose amount of the polyI:C polynucleotide adjuvant and the lipid-based adjuvant.

(70) The composition of paragraph (69), wherein the composition induces an antibody immune response that is at least about 2 times, 3 times, 4 times, 5 times, 6 times, 7 times, 8 times, 9 times or 10 times higher than the as defined identical control composition.

(71) The composition of paragraph (68), wherein the low per unit dose amount is capable of providing an enhanced immunogenicity as compared to an identical control composition that comprises an equivalent per unit dose amount or a higher per unit dose amount of the polyI:C polynucleotide adjuvant and the lipid-based adjuvant, does not comprise the amphipathic compound, and is formulated as an oil emulsion composition.

(72) The composition of paragraph (71), wherein the composition induces an antibody immune response that is at least equivalent to or at least 1.5 times, 2 times, 3 times, 4 times, 5 times, 6 times, 7 times, 8 times, 9 times or 10 times higher than the as defined identical control composition and/or a cellular immune response that is at least 1.5 times, 2 times, 2.5 times, 3 times, 3.5 times, 4 times, 4.5 times or 5 times higher than the identical control composition.

(73) The composition of any one of paragraphs (69) to (72), wherein the higher per unit dose amount is at least about 2-fold, 3-fold, 4-fold, 5-fold, 10-fold, 15-fold, 20-fold or 50-fold greater than the low per unit dose amount.

(74) The composition of any one of paragraphs (69) to (73), wherein the higher per unit dose amount of the polyI:C polynucleotide adjuvant and lipid-based adjuvant is at least about 10 micrograms, about 15 micrograms, about 20 micrograms or more of each per dose.

(75) The composition of any one of paragraphs (68) to (74), wherein the low per unit dose amount of the polyI:C polynucleotide adjuvant and lipid-based adjuvant is about 0.2 micrograms, about 0.5 micrograms, about 1 microgram, about 5 micrograms or less of each per dose.

(76) The composition of any one of paragraphs (68) to (75), wherein the low per unit dose amount is capable of inducing an antigen-specific antibody immune response at a non-logged antibody titer of at least about 15 million, 20 million, 25 million, 30 million or 35 million by about twelve weeks post-vaccination of a subject.

(77) The composition of any one of paragraphs (25) to (76) for use in the treatment or prevention of a disease or disorder ameliorated by an antibody immune response and/or cell-mediated immune response.

(78) The composition of any one of paragraphs (25) to (77) for use in the treatment or prevention of: a disease caused by a bacteria, a virus, a fungus, a parasite, an allergen, or a tumor cell that expresses the antigen.

(79) The composition of any one of paragraphs (25) to (77) for neutralizing a toxin, virus, bacterium or allergen, with an antibody produced against the antigen.

(80) A method comprising administering the composition of any one of paragraphs (25) to (77) to a subject in need thereof.

(81) The method according to paragraph (80), which is a method for inducing an antibody response and/or cell-mediated immune response to said antigen in said subject.

(82) The method according to paragraph (81), which is a method for the treatment and/or prevention of a disease caused by a bacteria, a virus, a fungus, a parasite, an allergen, or a tumor cell that expresses the antigen.

(83) The method according to paragraph (82), wherein the disease is influenza, a respiratory tract infection caused by human respiratory syncytial virus, pertussis, anthrax or malaria.

(84) The method according to paragraph (82), wherein the disease is cancer.

(85) The method according to paragraph (81), which is a method for the treatment and/or prevention of a neurodegenerative disease, wherein the neurodegenerative disease is associated with expression of the antigen.

(86) The method according to paragraph (85), wherein the neurodegenerative disease is Alzheimer's disease.

(87) A method for neutralizing a toxin, virus, bacterium or allergen, with an antibody, said method comprising administering the composition of any one of paragraphs (25) to (77) to a subject.

(88) The method of paragraph (87), wherein the toxin is a drug substance, for example cocaine.

(89) A kit comprising, in one or more separate containers, a polyI:C polynucleotide adjuvant, optionally as defined in any one of paragraphs (7) to (11); a lipid-based adjuvant, optionally as defined in any one of paragraphs (2) to (6); an amphipathic compound, optionally as defined in any one of paragraphs (12) to (20); and a hydrophobic carrier, optionally as defined in any one of paragraphs (21) to (24).

(90) The kit of paragraph (89), wherein the polyI:C polynucleotide adjuvant; the lipid-based adjuvant; the amphipathic compound; and the hydrophobic carrier are each in a separate container.

(91) The kit of paragraph (89), wherein the polyI:C polynucleotide adjuvant; the lipid-based adjuvant; and the amphipathic compound are together in a first container and the hydrophobic carrier is in a second container.

(92) The kit of paragraph (89), wherein the polyI:C polynucleotide adjuvant and the lipid-based adjuvant are together in a first container; the amphipathic compound is in a second container; and the hydrophobic carrier is in a third container.

(93) The kit of paragraph (89), wherein the polyI:C polynucleotide adjuvant and the lipid-based adjuvant are together in a first container and the amphipathic compound and the hydrophobic carrier are together in a second container.

(94) The kit of paragraph (89), wherein the polyI:C polynucleotide adjuvant is in a first container, the lipid-based adjuvant is in a second container, and the amphipathic compound and the hydrophobic carrier are together in a third container.

(95) The kit of any one of paragraphs (89) to (94) further comprising an antigen, wherein the antigen is together in the container with any one or more of the polyI:C polynucleotide adjuvant, the lipid-based adjuvant, the amphipathic compound, the hydrophobic carrier, and/or any mixture thereof; or the antigen is in a separate container.

(96) The kit of paragraph (95), wherein the antigen is as defined in any one of paragraphs (51) to (62).

(97) The kit of paragraph (95) or (96) further comprising a T-helper epitope, wherein the T-helper epitope is together in the container with any one or more of the polyI:C polynucleotide adjuvant, the lipid-based adjuvant, the amphipathic compound, the hydrophobic carrier, the antigen and/or any mixture thereof, or the T helper is in a separate container.

(98) The kit of paragraph (97), wherein the T-helper epitope is in the same container as the antigen and is separate from the antigen or is conjugated or fused to the antigen.

(99) The kit of paragraph (97) or (98), wherein the T-helper is PADRE comprising the amino acid sequence AKXVAAWTLKAAA (SEQ ID NO: 79); Tetanus toxoid peptide F21E comprising the amino acid sequence FNNFTVSFWLRVPKVSASHLE (SEQ ID NO: 80); or modified Tetanus toxin peptide A16L comprising the amino acid sequence AQYIKANSKFIGITEL (SEQ ID NO: 78).

(100) The kit of any one of paragraphs (89) to (99) further comprising instructions for use in preparing a pharmaceutical composition and/or instructions for use in inducing an antibody response and/or cell-mediated immune response in a subject.

(101) The kit of any one of paragraphs (89) to (100), which is for use in preparing a composition that is water-free or substantially free of water, wherein the composition that is substantially free of water comprises less than about 10%, 9%, 8%, 7%, 6%, 5%, 4%, 3%, 2%, 1%, 0.5%, 0.1%, 0.05% or 0.01% water on a weight/weight basis of the total weight of the carrier.

(102) The kit of any one of paragraphs (89) to (101), wherein the lipid-based adjuvant is as defined in any one of paragraphs (2) to (6); the polyI:C polynucleotide adjuvant is as defined in any one of paragraphs (7) to (11); the amphipathic compound is as defined in any one of paragraphs (12) to (20); and/or the hydrophobic carrier is as defined in any one of paragraphs (21) to (24).

(103) The kit of any one of paragraphs (89) to (102), wherein the lipid-based adjuvant is PAM$_3$Cys-Ser-(Lys)4 (SEQ ID NO: 1); the polyI:C polynucleotide adjuvant is a mixture of varying strand lengths of polyI and polyC, said mixture comprising an approximate molecular weight of 989,486 Daltons; the amphipathic compound is a mixture of S100 lipids and cholesterol or a mixture of dioleoyl phosphatidylcholine (DOPC) and cholesterol; and the hydrophobic carrier is a mannide oleate in mineral oil solution (e.g. MONTANIDE™ ISA51) VG.

The invention is further illustrated by the following non-limiting examples.

Examples

Example 1

Pathogen free, CD-1 mice, 6-8 weeks of age, were purchased from Charles River Laboratories (St. Constant, PQ) and housed according to institutional guidelines with water and food ad libitum under filter controlled air circulation.

All vaccines were prepared with the recombinant PA antigen derived from anthrax toxin (List Biologicals) with adjuvants polyI:C (Thermo-Fisher, USA) and/or Pam3CSK4 (SEQ ID NO: 1; EMC Microcollections, Germany). To prepare oil-based water-free formulation, antigen and/or polyI:C and/or Pam3CSK4 (SEQ ID NO: 1) adjuvant were prepared in sodium phosphate buffer (0.2M, pH 6.0) with S100 lipids (Lipoid Germany; 120 milligrams per milliliter) and cholesterol (Lipoid, Germany; 12 milligrams per milliliter). This preparation was then lyophilized to form a dry cake. Just prior to injection, the dry cake was resuspended in ISA51 VG oil (SEPPIC, France). Final vaccine preparation dose volume was 50 microliters and contained 1 microgram of PA antigen (20 micrograms per milliliter) with 1 microgram of polyI:C and/or Pam3CSK4 (SEQ ID NO: 1) adjuvant, as indicated (concentration of 20 micrograms per milliliter).

Mice received intramuscular vaccinations delivered as 25 microliters on each the left and right flank. Group 1 (n=10) was vaccinated with the oil-based water-free formulation containing no adjuvant. Group 2 (n=10) was vaccinated with the oil-based water-free formulation containing polyI:C adjuvant. Group 3 (n=10) was vaccinated with the oil-based water-free formulation containing Pam3CSK4 (SEQ ID NO: 1) adjuvant. Group 4 (n=10) was vaccinated with the oil-based water-free formulation containing both polyI:C and Pam3CSK4 (SEQ ID NO: 1).

Immunogenicity of the vaccine was determined by endpoint titration of serum collected on weeks 4, 6, 8, 12, 16, 20 and 24 post vaccination. Briefly, a 96-well EIA plate was coated overnight with 1 microgram per milliliter of recombinant PA antigen in sodium carbonate buffer (pH 9.5) at 4° C. Next day, plate was washed with 100 millimolar tris-buffered saline/Tween (TBST) and blocked at 1 hour at 37° C. with 3% gelatin (Biorad, USA). Plate was thoroughly washed with TBST then serum was added to the top row of each plate and 1:1 dilutions prepared down each column with TBST. On each plate, a negative control column was included with no serum. The plate was incubated overnight at 4° C. To develop, plates were washed with TBST and incubated with 1:1000 dilution of Protein G conjugated to alkaline phosphatase (Calbiochem, USA) for 1 hour at 37° C., then washed with 100 millimolar Tris-buffer (no tween), and then incubated with 1 microgram per milliliter of 4-nitrophenyl phosphate in Tris-buffer at 37° C. The $OD_{405}$ was measured with an ELISA plate reader. Antibody endpoint titre was determined as the reciprocal of the dilution required to give 1 standard deviation $OD_{405}$ above the average $OD_{405}$ of the negative control. Values are expressed in Log(10).

At some time points a toxin neutralization assay was also performed to assess the functionality of the antibodies in serum. Briefly, dilutions of sera were incubated with anthrax toxin (recombinant PA and LF proteins from List Biologicals, USA) for 30 minutes at 37° C. The sera-toxin preparations were then added to 96-well plate containing 5×10E4 J774 target cells per well. Plates were incubated at 37° C./5% CO2 for 4 hours. To determine the viability of the cells after incubation, MTT was added to each well and the plate were incubated for 2 hours at 37° C./5% CO2. The quantity of formazan was then measured at $OD_{570}$ using a plate reader. $OD_{570}$ was then plotted against dilution and ED50 determined from the inflection point of the curve. ED50 are expressed as Log(10).

Serum titre results are shown in FIG. 1a. Statistics were measured by 2-way ANOVA with Bonferroni post test comparing Group 1 to each group at each time point. The vaccine of the present invention, represented as Group 4, generated titres significantly higher than those generated by vaccines administered to Group 1 at 4 of the 7 time points. Titres generated by vaccines administered to Groups 2 and 3 were not significantly higher than those of Group 1.

Toxin neutralization assay was performed using serum collected at week 8 and results are shown in FIG. 1b. Statistics were measured by 1-way ANOVA with a Tukey post-test. The vaccine of the present invention, represented as Group 4, generated ED50 significantly higher than Group 1. The ED50 of Groups 2 and 3 were not significantly different from Group 1.

This data demonstrates that an oil-based water-free vaccine formulated with polyI:C and Pam3CSK4 (SEQ ID NO: 1) adjuvant combination can generate significantly higher antibody titres for an extended period of time compared to similar formulations containing no adjuvant, and this cannot be achieved by using only one of these adjuvants. The antibodies generated to this vaccine also have increased functional capacity.

Example 2

Pathogen free, CD-1 mice, 6-8 weeks of age, were purchased from Charles River Laboratories (St. Constant, PQ) and housed according to institutional guidelines with water and food ad libitum under filter controlled air circulation.

All vaccines were prepared with recombinant HA antigen (H5N1, A/Vietnam/1203/2004; Protein Sciences, USA) with adjuvants: Alhydrogel (Brentagg, Canada), or polyI:C (Thermo-Fisher, USA) and Pam3CSK4 (SEQ ID NO: 1; EMC Microcollections, Germany). To prepare Alhydrogel-adjuvanted formulation (alum), antigen was prepared in sodium phosphate buffer (0.1M, pH 7.0) and mixed with a hydrogel. Final vaccine preparation contained 1 microgram of antigen in a 50 microliter dose volume. To prepare emulsion formulations, antigen and polyI:C and Pam3CSK4 (SEQ ID NO: 1) adjuvants were first prepared in sodium phosphate buffer (0.1M, pH 7.0) then mixed 1:1 (v/v) with ISA51 VG oil (SEPPIC, France). Final vaccine preparation contained 1 microgram of antigen with 1 or 20 micrograms of each polyI:C and Pam3CSK4 (SEQ ID NO: 1) adjuvant in a 50 microliter dose volume (concentration of 20 micrograms per milliliter or 400 micrograms per milliliter). To prepare oil-based water-free formulation, antigen and polyI:C and Pam3CSK4 (SEQ ID NO: 1) adjuvant were prepared in sodium phosphate buffer (0.1M, pH 7.0) with S100 lipids (Lipoid, Germany; 120 micrograms per milliliter) and cholesterol (Lipoid, Germany; 12 micrograms per milliliter). This preparation was then lyophilized to forma dry cake. Just prior to injection, the dry cake was resuspended in ISA51 VG oil (SEPPIC, France). Final vaccine preparation dose volume was 50 microliters and contained 1 microgram of HA antigen (20 micrograms per milliliter) with 1 or 20 micrograms of each polyI:C and Pam3CSK4 (SEQ ID NO: 1) adjuvant (concentration of 20 micrograms per milliliter or 400 micrograms per milliliter).

Mice received intramuscular vaccinations delivered as 25 microliters on each the left and right flank. Group 1 (n=8) was vaccinated with the alum-adjuvanted vaccine. Group 2 (n=8) was vaccinated with the oil-based water-free formulation containing 1 microgram dose of each polyI:C and Pam3CSK4 (SEQ ID NO: 1). Group 3 (n=8) was vaccinated with the oil-based water-free formulation containing 20 microgram dose of each polyI:C and Pam3CSK4 (SEQ ID NO: 1). Group 4 (n=4) was vaccinated with emulsion formulation containing 1 microgram dose of each polyI:C and Pam3CSK4 (SEQ ID NO: 1). Group 5 (n=4) was vaccinated with emulsion formulation containing 20 micrograms each of polyI:C and Pam3CSK4 (SEQ ID NO: 1).

Immunogenicity of the vaccine was determined by end-point titration of serum collected 12 weeks post vaccination. Briefly, a 96-well EIA plate was coated overnight with 1 microgram per milliliter of recombinant HA antigen in sodium carbonate buffer (pH 9.5) at 4° C. Next day, plate was washed with 100 millimolar tris-buffered saline/Tween (TBST) and blocked at 1 hour at 37° C. with 3% gelatin (Biorad, USA). Plate was thoroughly washed with TBST then serum was added to the top row of each plate and 1:1 dilutions prepared down each column with TBST. On each plate, a negative control column was included with no serum. The plate was incubated overnight at 4° C. To develop, plates were washed with TBST and incubated with 1:1000 dilution of Protein G conjugated to alkaline phosphatase (Calbiochem, USA) for 1 hour at 37°, then washed with 100 millimolar Tris-buffer (no tween), and then incubated with 1 microgram per milliliter of 4-nitrophenyl phosphate in Tris-buffer at 37° C. The $OD_{405}$ was measured with an ELISA plate reader. Antibody endpoint titre was determined as the reciprocal of the dilution required to give 1 standard deviation $OD_{405}$ above the average $OD_{405}$ of the negative control. Values are expressed in Log(10). The results are shown in FIG. 2.

The results are shown in Table 5 and FIG. 2. The vaccine of the present invention, represented as Group 2, generated significantly higher responses than Group 1, Group 3 and Group 4 (p<0.05). The responses between Group 2 and Group 5 were not significantly different (p>0.05). Statistical significance was calculated between groups using student t-test.

This data demonstrates that the oil-based formulation can be used to generate high antibody titres to an antigen using low dose combination of the adjuvants polyI:C and Pam3CSK4 (SEQ ID NO: 1) (20 micrograms per milliliter). The response is comparable to an emulsion formulation prepared with 20× higher dose of adjuvants (400 micrograms per milliliter) and significantly higher than the responses generated by the emulsion formulation with the same low dose of adjuvants.

TABLE 5

Raw data of serum antibody titres measured in vaccinated mice at 12 weeks post immunization.

| Group | Vaccine | n | Average Titre | SEM |
|---|---|---|---|---|
| 1 | Alum | 8 | 5.182 | 0.168 |
| 2 | 1 microgram polyI:C + Pam3CSK4 (SEQ ID NO: 1), oil-based | 8 | 7.252 | 0.192 |
| 3 | 20 microgram polyI:C + Pam3CSK4 (SEQ ID NO: 1), oil-based | 8 | 6.462 | 0.161 |
| 4 | 1 microgram polyI:C + Pam3CSK4 (SEQ ID NO: 1), emulsion | 4 | 6.537 | 0.144 |
| 5 | 20 microgram polyI:C + Pam3CSK4 (SEQ ID NO: 1), emulsion | 4 | 7.064 | 0.194 |

Example 3

Pathogen free, C57BL6 mice, 6-8 weeks of age, were purchased from Charles River Laboratories (St. Constant, PQ) and housed according to institutional guidelines with water and food ad libitum under filter controlled air circulation.

All vaccines were prepared with the antigen $HPV16E7_{49-57}$ (R9F: RAHYNIVTF; SEQ ID NO: 2) conjugated to universal T-helper epitope PADRE (R9F-PADRE; NeoMPS, USA) and the adjuvants polyI:C (Thermo-Fisher, USA) and Pam3CSK4 (SEQ ID NO: 1); EMC Microcollections, Germany). To prepare oil-based water-free formulation, the R9F-PADRE antigen was first diluted in 0.2% PEG-H2O with lipids DOPC (Lipoid, Germany; 120 milligrams per milliliter) and cholesterol (Lipoid, Germany; 12 milligrams per milliliter). A mixture of the adjuvants (polyI:C and Pam3CSK4; SEQ ID NO: 1) was prepared in water and then added to the antigen-lipid mixture. The vaccine components were then lyophilized to form a dry cake. Just prior to injection, the dry cake was resuspended in ISA51 VG oil (SEPPIC, France). The final vaccine preparation dose volume was 50 microliters and contained 1 microgram of R9F-PADRE antigen (20 micrograms per milliliter) with each adjuvant at 0.2 micrograms (4 micrograms per milliliter), 1.0 micrograms (20 micrograms per milliliter), 5.0 micrograms (100 micrograms per milliliter) or 10.0 micrograms (200 micrograms per milliliter).

Mice received subcutaneous vaccinations delivered as 50 microliters in the right flank. Group 1 (n=4) was vaccinated with R9F-PADRE in oil-based water-free vaccine formulation containing 0.2 microgram dose of each polyI:C and Pam3CSK4 (SEQ ID NO: 1). Group 2 (n=4) was vaccinated with R9F-PADRE in oil-based water-free vaccine formulation containing 1.0 microgram dose of each polyI:C and Pam3CSK4 (SEQ ID NO: 1). Group 3 (n=4) was vaccinated with R9F-PADRE in oil-based water-free vaccine formulation containing 5.0 microgram dose of each polyI:C and Pam3CSK4 (SEQ ID NO: 1). Group 4 (n=4) was vaccinated with R9F-PADRE in oil-based water-free vaccine formulation containing 10.0 microgram dose of each polyI:C and Pam3CSK4 (SEQ ID NO: 1).

The immunogenicity of the vaccine formulations was evaluated by IFN-gamma ELISPOT assay performed eights days after immunization. Briefly, all mice were euthanized and spleens removed. One naïve mouse was also terminated and served as a naïve, non-vaccinated control. A single cell suspension was prepared and splenocytes were loaded into anti-IFN-gamma coated wells (500,000 cells per well) of an ELISPOT plate (BD Bioscience, USA). Cells were stimulated with 10 micrograms per milliliter of the $HPV15E7_{49-57}$ peptide (R9F: RAHYNIVTF; SEQ ID NO: 2) or media containing no peptide (background) in the ELISPOT plate for 18 hours. Next day, the plate was developed using AEC kit (Sigma, USA) and individual IFN-gamma secreting cells enumerated using an Immunospot plate reader (Cellular Technologies Ltd, USA). Results are shown in FIG. 3. Statistics performed by 1-way ANOVA with Tukey post-test.

Mice in Group 1 generated an average response of 418±13 spot forming units (SFU) to stimulation with the R9F peptide. Response to background was negligible, <10 SFU. Mice in Group 2 generated average response of 260±70 SFU to stimulation with the R9F peptide. Response to background was negligible, <10 SFU. Mice in Group 3 generated average response of 247±76 SFU to stimulation with the R9F peptide. Response to background was negligible, <10 SFU. Mice in Group 4 generated average response of 149±25 SFU to stimulation with the R9F peptide. Response to background was negligible, <10 SFU. This response was significantly lower than the response generated by Group 1, *p<0.05.

These results demonstrate that the polyI:C and Pam3CSK4 (SEQ ID NO: 1) adjuvant combination can stimulated potent IFN-gamma immune responses to a vaccine antigen and that is most effective when used at doses less than 200 micrograms per milliliter.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to encompass the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items.

As used herein, whether in the specification or the appended claims, the transitional terms "comprising", "including", "carrying", "having", "containing", "involving", and the like are to be understood as being inclusive or open-ended (i.e., to mean including but not limited to), and they do not exclude unrecited elements, materials or method steps. Only the transitional phrases "consisting of" and "consisting essentially of", respectively, are closed or semi-closed transitional phrases with respect to claims and exemplary embodiment paragraphs herein. The transitional phrase "consisting of" excludes any element, step, or ingredient which is not specifically recited. The transitional phrase "consisting essentially of" limits the scope to the specified elements, materials or steps and to those that do not materially affect the basic characteristic(s) of the invention disclosed and/or claimed herein.

REFERENCES

1) Agger, E. M.; Rosenkrands, I.; Olsen, A. W.; Hatch, G.; Williams, A.; Kritsch, C.; Lingnau, K.; von Gabain, A.; Andersen, C. S.; Korsholm, K. S.; Andersen, P. (2006) Protective immunity to tuberculosis with Ag85B-ESAT-6 in a synthetic cationic adjuvant system IC31, *Vaccine* 24(26), 5452-5460.
2) Agrawal, S.; Gupta, S. (2011) TLR1/2, TLR7, and TLR9 signals directly activate human peripheral blood naive and memory B cell subsets to produce cytokines, chemokines, and hematopoietic growth factors, *J. Clin. Immunol.* 31(1), 89-98.
3) Aichele, P.; Brduscha-Riem, K.; Zinkernagel, R. M.; Hengartner, H.; Pircher, H. (1995) T cell priming versus T cell tolerance induced by synthetic peptides, *J. Exp. Med.* 182(1), 261-266.
4) Alexopoulou, L.; Holt, A. C.; Medzhitov, R.; Flavell, R. A. (2001) Recognition of double-stranded RNA and activation of NF-κB by Toll-like receptor 3, *Nature* 413 (6857), 732-738.
5) Altieri, D. C.; Marchisio, P. C. (1999) Survivin apoptosis: an interloper between cell death and cell proliferation in cancer, *Lab. Invest.* 79(11), 1327-1333.
6) Altschul, S. F.; Gish, W.; Miller, W.; Myers, E. W.; Lipman, D. J. (1990) Basic local alignment search tool, *J. Mol. Biol.* 215(3), 403-410.
7) Alving, C. R.; Peachman, K. K.; Rao, M.; Reed, S. G. (2012) Adjuvants for human vaccines, *Curr. Opin. Immunol.* 24(3), 310-315.
8) Anders, H. J.; Zecher, D.; Pawar, R. D.; Patole, P. S. (2005) Molecular mechanisms of autoimmunity triggered by microbial infection, *Arthritis. Res. Ther.* 7(5), 215-224.
9) Avril, T.; de Tayrac, M.; Leberre, C.; Quillien, V. (2009) Not All Polyriboinosinic-polyribocytidylic Acids (Poly I:C) are Equivalent for Inducing Maturation of Dendritic Cells: Implication for α-type-1 Polarized DCs, *J. Immunother.* 32(4), 353-362.
10) Awasthi, A.; Mehrotra, S.; Bhakuni, V.; Dutta, G. P.; Levy, H. B.; Maheshwari, R. K. (1997) Poly ICLC enhances the antimalarial activity of chloroquine against multidrug-resistant *Plasmodium yoelii nigeriensis* in mice, *J. Interferon Cytokine Res.* 17(7), 419-423.
11) Bagchi, A.; Herrup, E. A.; Warren, H. S.; Trigilio, J.; Shin, H. S.; Valentine, C.; Hellman, J. (2007) MyD88-dependent and MyD88-independent Pathways in Synergy, Priming, and Tolerance between TLR Agonists, *J. Immunol.* 178(2), 1164-1171.
12) Banga, A. K. *Therapeutic Peptides and Proteins, Formulation, Processing and Delivery Systems* (Lancaster, Pa.: Technomic Publishing Co., 1995).
13) Barchet, W.; Wimmenauer, V.; Schlee, M.; Hartmann, G. (2008) Accessing the therapeutic potential of immunostimulatory nucleic acids, *Curr. Opin. Immunol.* 20(4), 389-395.
14) Berinstein, N. L.; Karkada, M.; Morse, M. A.; Nemunaitis, J. J.; Chatta, G.; Kaufman, H.; Odunsi, K.; Nigam, R.; Sammatur, L.; MacDonald, L. D.; Weir, G. M.; Stanford, M. M.; Mansour, M. (2012) First-in-man application of a novel therapeutic cancer vaccine formulation with the capacity to induce multi-functional T cell responses in ovarian, breast and prostate cancer patients, *J. Transl. Med.* 10(156), 1-12.
15) Berinstein, N. L.; Karkada, M.; Oza, A. M.; Odunsi, K.; Villella, J. A.; Nemunaitis, J. J.; Morse, M. A.; Pejovic, T.; Bentley, J.; Buyse, M.; Nigam, R.; Weir, G. M.; MacDonald, L. D.; Quinton, T.; Rajagopalan, R.; Sharp, K.; Penwell, A.; Sammatur, L.; Burzykowski, T.; Stanford, M. M.; Mansour, M. (2015) Survivin-targeted immunotherapy drives robust polyfunctional T cell generation and differentiation in advanced ovarian cancer patients, *Oncoimmunology* 4(8), e1026529-1-e1026529-10.
16) Bever, C. T. Jr.; Salazar, A. M.; Neely, E.; Ferraraccio, B. E.; Rose, J. W.; McFarland H. F.; Levy, H. B.; McFarlin, D. E. (1986) Preliminary trial of poly ICLC in chronic progressive multiple sclerosis, *Neurology* 36(4), 494-498.

17) Blander, J. M. (2008) Phagocytosis and antigen presentation: a partnership initiated by Toll-like receptors, *Ann. Rheum. Dis.* 67(Suppl 3), iii44-iii49.

18) Bobst, A. M.; Langemeier, P. W.; Torrence, P. F.; De Clercq, E. (1981) Interferon Induction by Poly(inosinic acid) Poly(cytidylic acid) Segmented by Spin-Labels, *Biochemistry* 20(16), 4798-4803.

19) Brewer, K. D.; Lake, K.; Pelot, N.; Stanford, M. M.; DeBay, D. R.; Penwell, A.; Weir, G. M.; Karkada, M.; Mansour, M.; Bowen, C. V. (2014) Clearance of depot vaccine SPIO-labeled antigen and substrate visualized using MRI, *Vaccine* 32(51), 6956-6962.

20) Caproni, E.; Tritto, E.; Cortese, M.; Muzzi, A.; Mosca, F.; Monaci, E.; Baudner, B.; Seubert, A.; De Gregorio, E. (2012) MF59 and Pam3CSK4 Boost Adaptive Responses to Influenza Subunit Vaccine through an IFN Type I-Independent Mechanism of Action, *J. Immunol.* 188(7), 3088-3098.

21) Caruthers, M. H.; Beaucage, S. L.; Efcavitch, J. W.; Fisher, E. F.; Matteucci, M. D.; Stabinsky, Y. (1980) New chemical methods for synthesizing polynucleotides, *Nucleic Acids Res. Symp. Ser.* (7), 215-223.

22) Chang, Z. L. (2010) Important aspects of Toll-like receptors, ligands and their signaling pathways, *Inflamm. Res.* 59(10), 791-808.

23) Chirigos, M. A.; Schlick, E.; Ruffmann, R.; Budzynski, W.; Sinibaldi, P.; Gruys, E. (1985) Pharmacokinetic and therapeutic activity of polyinosinic-polycytidylic acid stabilized with poly-L-lysine in carboxymethylcellulose [poly(I,C)-LC], *J. Biol. Response Mod.* 4(6), 621-627.

24) Cui, Z.; Qiu, F. (2006) Synthetic double-stranded RNA poly(I:C) as a potent peptide vaccine adjuvant: therapeutic activity against human cervical cancer in a rodent model, *Cancer Immunol. Immunother.* 55(10), 1267-1279.

25) de Clercq, E.; Hattori, M.; Ikehara, M. (1975) Antiviral activity of polynucleotides: copolymers of inosinic acid and N2-dimethylguanylic of 2-methylthioinosinic acid, *Nucleic Acids Res.* 2(1), 121-129.

26) de Clercq, E.; Torrence, P. F.; Stollar, B. D.; Hobbs, J.; Fukui, T.; Kakiuchi, N.; Ikehara, M. (1978) Interferon induction by a 2'-modified double-helical RNA, poly(2'-azido-2'-deoxyinosinic acid). polycytidylic acid, *Eur. J. Biochem.* 88(2), 341-349.

27) De Gregorio, E.; Caproni, E.; Ulmer, J. B. (2013) Vaccine adjuvants: mode of action, *Front. Immunol.* 4(214), 1-6.

28) Diehl, K. H.; Hull, R.; Morton, D.; Pfister, R.; Rabemampianina, Y.; Smith, D.; Vidal, J. M.; van de Vorstenbosch, C. (2001) A good practice guide to the administration of substances and removal of blood, including routes and volumes, *J. Appl. Toxicol.* 21(1), 15-23.

29) Dong, L. W.; Kong, X. N.; Yan, H. X.; Yu, L. X.; Chen, L.; Yang, W.; Liu, Q.; Huang, D. D.; Wu, M. C.; Wang, H. Y. (2008) Signal regulatory protein alpha negatively regulates both TLR3 and cytoplasmic pathways in type I interferon induction, *Mol. Immunol.* 45(11), 3025-3035.

30) Droller, M. J. (1987) Immunotherapy of metastatic renal cell carcinoma with polyinosinic-polycytidylic acid, *J. Urol.* 137(2), 202-206.

31) Dubensky, T. W. Jr.; Reed, S. G. (2010) Adjuvants for cancer vaccines, *Semin. Immunol.* 22(3), 155-161.

32) Durie, B. G.; Levy, H. B.; Voakes, J.; Jett, J. R.; Levine, A. S. (1985) Poly(I,C)-LC as an interferon inducer in refractory multiple myeloma, *J. Biol. Response Mod.* 4(5), 518-524.

33) Duthie, M. S.; Windish, H. P.; Fox, C. B.; Reed, S. G. (2011) Use of defined TLR ligands as adjuvants within human vaccines, *Immunol. Rev.* 239(1), 178-196.

34) Farina, G. A.; York, M. R.; Di Marzio, M.; Collins, C. A.; Meller, S.; Homey, B.; Rifkin, I. R.; Marshak-Rothstein, A.; Radstake, T. R.; Lafyatis, R. (2010) Poly(I:C) drives type I IFN- and TGFβ-mediated inflammation and dermal fibrosis simulating altered gene expression in systemic sclerosis, *J. Invest. Dermatol.* 130(11), 2583-2593.

35) Fujimura, T.; Nakagawa, S.; Ohtani, T.; Ito, Y.; Aiba, S. (2006) Inhibitory effect of the polyinosinic-polycytidylic acid/cationic liposome on the progression of murine B16F10 melanoma, *Eur. J. Immunol.* 36(12), 3371-3380.

36) Fukui, T.; Kakiuchi, N.; Ikehara, M. (1977) Polynucleotides. XLV Synthesis and properties of poly(2'-azido-2'-deoxyinosinic acid), *Nucleic Acids Res.* 4(8), 2629-2639.

37) Gallo, R. C. (2015) Developing a Successful HIV Vaccine, *J. Infect. Dis.* 212(Suppl 1), S40-S41.

38) Ghosh, T. K.; Mickelson D. J.; Fink, J.; Solberg, J. C.; Inglefield, J. R.; Hook, D.; Gupta, S. K.; Gibson, S.; Alkan, S. S. (2006) Toll-like receptor (TLR) 2-9 agonists-induced cytokines and chemokines: I. Comparison with T cell receptor-induced responses, *Cell. Immunol.* 243(1), 48-57.

39) Ghosh, T. K.; Mickelson, D. J.; Solberg, J. C.; Lipson, K. E.; Inglefield, J. R.; Alkan, S. S. (2007) TLR-TLR cross talk in human PBMC resulting in synergistic and antagonistic regulation of type-1 and 2 interferons, IL-12 and TNF-α, *Int. Immunopharmacol.* 7(8), 1111-1121.

40) Govindaraj, R. G.; Manavalan, B.; Lee, G.; Choi, S. (2010) Molecular modeling-based evaluation of hTLR10 and identification of potential ligands in Toll-like receptor signaling, *PLoS One* 5(9), e12713-1-e12713-13.

41) Gowen, B. B.; Wong, M. H.; Jung, K. H.; Sanders, A. B.; Mitchell, W. M.; Alexopoulou, L.; Flavell, R. A.; Sidwell, R. W. (2007) TLR3 is essential for the induction of protective immunity against Punta Toro Virus infection by the double-stranded RNA (dsRNA), poly(I:C12U), but not Poly(I:C): differential recognition of synthetic dsRNA molecules, *J. Immunol.* 178(8), 5200-5208.

42) Graham, B. S.; McElrath, M. J.; Keefer, M. C.; Rybczyk, K.; Berger, D.; Weinhold, K. J.; Ottinger, J.; Ferarri, G.; Montefiori, D. C.; Stablein, D.; Smith, C.; Ginsberg, R.; Eldridge, J.; Duerr, A.; Fast, P.; Haynes, B. F.; AIDS Vaccine Evaluation Group. (2010) Immunization with cocktail of HIV-derived peptides in montanide ISA-51 is immunogenic, but causes sterile abscesses and unacceptable reactogenicity, *PLoS One* 5(8), e11995-1-e11995-8.

43) Greene, J. J.; Alderfer, J. L.; Tazawa, I.; Tazawa, S.; Ts'o, P. O.; O'Malley, J. A.; Carter, W. A. (1978) Interferon induction and its dependence on the primary and secondary structure of poly(inosinic acid).poly(cytidylic acid), *Biochemistry* 17(20), 4214-4220.

44) Gupta, R. K. (1998) Aluminum compounds as vaccine adjuvants, *Adv. Drug Deliv. Rev.* 1998, 32(3), 155-172.

45) Gupta, R. K.; Chang, A. C.; Griffin, P.; Rivera, R.; Siber, G. R. (1996) In vivo distribution of radioactivity in mice after injection of biodegradable polymer microspheres containing 14C-labeled tetanus toxoid, *Vaccine* 14(15), 1412-1416.

46) Guschlbauer, W.; Blandin, M.; Drocourt, J. L.; Thang, M. N. (1977) Poly-2'-deoxy-2'-fluoro-cytidylic acid: enzymatic synthesis, spectroscopic characterization and interaction with poly-inosinic acid, *Nucleic Acids Res.* 4(6), 1933-1943.

47) Hafner, A. M.; Corthesy, B.; Merkle, H. P. (2013) Particulate formulations for the delivery of poly(I:C) as vaccine adjuvant, *Adv. Drug. Deliv. Rev.* 65(10), 1386-1399.

48) Hailemichael, Y.; Dai, Z.; Jaffarzad, N.; Ye, Y.; Medina, M. A.; Huang, X. F.; Dorta-Estremera, S. M.; Greeley, N. R.; Nitti, G.; Peng, W.; Liu, C.; Lou, Y.; Wang, Z.; Ma, W.; Rabinovich, B.; Sowell, R. T.; Schluns, K. S.; Davis, R. E.; Hwu, P.; Overwijk, W. W. (2013) Persistent antigen at vaccination sites induces tumor-specific $CD8^+$ T cell sequestration, dysfunction and deletion, *Nat. Med.* 19(4), 465-472.

49) Hansen, M.; Met, O.; Svane, I. M.; Andersen, M. H. (2012) Cellular based cancer vaccines: type 1 polarization of dendritic cells, *Curr. Med. Chem.* 19(25), 4239-4246.

50) He, P.; Zou, Y.; Hu, Z. (2015) Advances in aluminum hydroxide-based adjuvant research and its mechanism, *Hum. Vaccin. Immunother.* 11(2), 477-488.

51) Heimlich, J. M.; Regnier, F. E.; White, J. L.; Hem, S. L. (1999) The in vitro displacement of adsorbed model antigens from aluminium-containing adjuvants by interstitial proteins, *Vaccine* 17(22), 2873-2881.

52) Hendrix, C. W.; Margolick, J. B.; Petty, B. G.; Markham, R. B.; Nerhood, L.; Farzadegan, H.; Ts'o, P. O.; Lietman, P. S. (1993) Biologic effects after a single dose of poly (I):poly(C12U) in healthy volunteers, *Antimicrob. Agents Chemother.* 37(3), 429-435.

53) Horn, T.; Vasser, M. P.; Struble, M. E.; Crea, R. (1980) Synthesis of oligonucleotides on cellulose. Part II: Design and synthetic strategy to the synthesis of 22 oligodeoxynucleotides coding for gastric inhibitory polypeptide (GIP), *Nucleic Acids Symp. Ser.* (7), 225-232.

54) Houston, W. E.; Crabbs, C. L.; Stephen, E. L.; Levy, H. B. (1976) Modified polyriboinosinic-polyribocytidylic acid, an immunological adjuvant, *Infect. Immun.* 14(1), 318-319.

55) Ichinohe, T.; Tamura, S.; Kawaguchi, A.; Ninomiya, A.; Imai, M.; Itamura, S.; Odagiri, T.; Tashiro, M.; Takahashi, H.; Sawa, H.; Mitchell, W. M.; Strayer, D. R.; Carter, W. A.; Chiba, J.; Kurata, T.; Sata, T.; Hasegawa, H. (2007) Cross-protection against H5N1 influenza virus infection is afforded by intranasal inoculation with seasonal trivalent inactivated influenza vaccine, *J. Infect. Dis.* 196(9), 1313-1320.

56) Ishii, K. J.; Akira, S. (2007) Toll or toll-free adjuvant path toward the optimal vaccine development, *J. Clin. Immunol.* 27(4), 363-371.

57) Johnston, M. I.; Stollar, B. D.; Torrence, P. F.; Witkop, B. (1975) Structural features of double-stranded polyribonucleotides required for immunological specificity and interferon induction, *Proc. Natl. Acad. Sci. U.S.A.* 72(11), 4564-4568.

58) Kamath, A. T.; Valenti, M. P.; Rochat, A. F.; Agger, E. M.; Lingnau, K.; von Gabain, A.; Andersen, P.; Lambert, P. H.; Siegrist, C. A. (2008) Protective anti-mycobacterial T cell responses through exquisite in vivo activation of vaccine-targeted dendritic cells, *Eur. J. Immunol.* 38(5), 1247-1256.

59) Kang, S. J.; Locksley, R. M. (2009) The inflammasome and alum-mediated adjuvanticity, *F1000 Biol. Rep.* 1(15), 1-5.

60) Kato, H.; Takeuchi, O.; Sato, S.; Yoneyama, M.; Yamamoto, M.; Matsui, K.; Uematsu, S.; Jung, A.; Kawai, T.; Ishii, K. J.; Yamaguchi, O.; Otsu, K.; Tsujimura, T.; Koh, C. S.; Reis e Sousa, C.; Matsuura, Y.; Fujita, T.; Akira, S. (2006) Differential roles of MDA5 and RIG-I helicases in the recognition of RNA viruses, *Nature* 441(7089), 101-105.

61) Kawaoka, Y.; Yamnikova, S.; Chambers, T. M.; Lvov, D. K.; Webster, R. G. (1990) Molecular characterization of a new hemagglutinin, subtype H14, of influenza A virus, *Virology* 179(2), 759-767

62) Kende, M.; Lupton, H. W.; Rill, W. L.; Gibbs, P.; Levy, H. B.; Canonico, P. G. (1987) Ranking of Prophylactic Efficacy of Poly(ICLC) against Rift Valley Fever Virus Infection in Mice by Incremental Relative Risk of Death, *Antimicrob. Agents Chemother.* 31(8), 1194-1198.

63) Koh, Y. T.; Higgins, S. A.; Weber, J. S.; Kast, W. M. (2006) Immunological consequences of using three different clinical/laboratory techniques of emulsifying peptide-based vaccines in incomplete Freund's adjuvant, *J. Transl. Med.* 4(42), 1-12.

64) Kool, M.; Soullie, T.; van Nimwegen, M.; Willart, M. A. M.; Muskens, F.; Jung, S.; Hoogsteden, H. C.; Hammad, H.; Lambrecht, B. N. (2008) Alum adjuvant boosts adaptive immunity by inducing uric acid and activating inflammatory dendritic cells, *J. Exp. Med.* 205(4), 869-882.

65) Krown, S. E.; Kerr, D.; Stewart, W. E. 2nd; Field, A. K.; Oettgen, H. F. (1985) Phase I trials of poly(L,C) complexes in advanced cancer, *J. Biol. Response Mod.* 4(6), 640-649.

66) Kumru, O. S.; Joshi, S. B.; Smith, D. E.; Middaugh, C. R.; Prusik, T.; Volkin, D. B. (2014) Vaccine instability in the cold chain: Mechanisms, analysis and formulation strategies, *Biologicals* 42(5), 237-259.

67) Lahiri, A.; Das, P.; Chakravortty, D. (2008) Engagement of TLR signaling as adjuvant: towards smarter vaccine and beyond, *Vaccine* 26(52), 6777-6783.

68) Leenaars, M.; Koedam, M. A.; Hendriksen, C. F.; Claassen, E. (1998) Immune responses and side effects of five different oil-based adjuvants in mice, *Vet. Immunol. Immunopathol.* 61(2-4), 291-304.

69) Levy, H. B. (1985) Historical overview of the use of polynucleotides in cancer, *J. Biol. Response Mod.* 4(5), 475-480.

70) Levy, H. B; Lvovsky, E. (1978) Topical treatment of vaccinia virus infection with an interferon inducer in rabbits, *J. Infect. Dis.* 137(1), 78-81.

71) Lim, S. N.; Kuhn, S.; Hyde, E.; Ronchese, F. (2012) Combined TLR stimulation with Pam3Cys and Poly I: C enhances Flt3-ligand dendritic cell activation for tumor immunotherapy, *J. Immunother.* 35(9), 670-679.

72) Llopiz, D.; Dotor, J.; Zabaleta, A.; Lasarte, J. J.; Prieto, J.; Borrs-Cuesta, F.; Sarobe, P. (2008) Combined immunization with adjuvant molecules poly(I:C) and anti-CD40 plus a tumor antigen has potent prophylactic and therapeutic antitumor effects, *Cancer Immunol. Immunother.* 57(1), 19-29.

73) Matsumoto, M.; Seya, T. (2008) TLR3: interferon induction by double-stranded RNA including poly(I:C). *Adv. Drug Deliv. Rev.* 60(7), 805-812.

74) Merrifield, B. (1997) Concept and early development of solid-phase peptide synthesis, *Methods Enzymol.* 289, 3-13.

75) Moyle, P. M.; Toth. I. (2008) Self-adjuvanting lipopeptide vaccines, *Curr. Med. Chem.* 15(5), 506-516.

76) Nakamura, O.; Shitara, N.; Matsutani, M.; Takakura, K.; Machida, H. (1982) Phase I-II trials of poly(ICLC) in malignant brain tumor patients, *J. Interferon. Res.* 2(1), 1-4.

77) Napolitani, G.; Rinaldi, A.; Bertoni, F.; Sallusto, F.; Lanzavecchia, A. (2005) Selected Toll-like receptor agonist combinations synergistically trigger a T helper type 1-polarizing program in dendritic cells, *Nat. Immunol.* 6(8), 769-776.

78) Needleman, S. B.; Wunsch, C. D. (1970) A general method applicable to the search for similarities in the amino acid sequence of two proteins, *J. Mol. Biol.* 48(3), 443-453.

79) Ogawa, C.; Liu, Y. J.; Kobayashi, K. S. (2011) Muramyl dipeptide and its derivatives: peptide adjuvant in immunological disorders and cancer therapy, *Curr. Bioact. Compd.* 7(3), 180-197.

80) Ouyang, X.; Negishi, H.; Takeda, R.; Fujita, Y.; Taniguchi, T.; Honda, K. (2007) Cooperation between MyD88 and TRIF pathways in TLR synergy via IRF5 activation, Biochem. *Biophys. Res. Commun.* 354(4), 1045-1051.

81) Padalko, E.; Nuyens, D.; De Palma, A.; Verbeken, E.; Aerts, J. L.; De Clercq, E.; Carmeliet, P.; Neyts, J. (2004) The Interferon Inducer Ampligen [poly(I)-poly(C12U)] Markedly Protects Mice against Coxsackie B3 Virus-Induced Myocarditis, *Antimicrob. Agents Chemother.* 48(1), 267-274.

82) Pearson, W. R.; Lipman, D. J. (1988) Improved tools for biological sequence comparison, *Proc. Nati. Acad. Sci. U.S.A.* 85(8), 2444-2448.

83) Poast, J.; Seidel, H. M.; Hendricks, M. D.; Haslam, J. A.; Levy, H. B.; Baron, S. (2002) Poly I:CLC induction of the interferon system in mice: an initial study of four detection methods, *J. Interferon Cytokine Res.* 22(10), 1035-1040.

84) Pone, E. J.; Lou, Z.; Lam, T.; Greenberg, M. L.; Wang, R.; Xu, Z.; Casali, P. (2015) B cell TLR1/2, TLR4, TLR7 and TLR9 interact in induction of class switch DNA recombination: modulation by BCR and CD40, and relevance to T-independent antibody responses, *Autoimmunity* 48(1), 1-12.

85) Pone, E. J.; Zhang, J.; Mai, T.; White, C. A.; Li, G.; Sakakura, J. K.; Patel, P. J.; Al-Qahtani, A.; Zan, H.; Xu, Z.; Casali, P. (2012) BCR-signalling synergizes with TLR-signalling for induction of AID and immunoglobulin class-switching through the non-canonical NF-κB pathway, *Nat. Commun.* 3(767), 1-12.

86) Pulendran, B.; Ahmed, R. (2006) Translating innate immunity into immunological memory: implications for vaccine development, *Cell* 124(4), 849-863.

87) Puri, S. K.; Dutta, G. P.; Levy, H. B.; Maheshwari, R. K. (1996) Poly ICLC inhibits *Plasmodium cynomolgi* B malaria infection in rhesus monkeys, *J. Interferon. Cytokine Res.* 16(1), 49-52.

88) Re, F.; Strominger, J. L. (2004) IL-10 released by concomitant TLR2 stimulation blocks the induction of a subset of Th1 cytokines that are specifically induced by TLR4 or TLR3 in human dendritic cells, *J. Immunol.* 173(12), 7548-7555.

89) Riedl, K.; Riedl, R.; von Gabain, A.; Nagy, E.; Lingnau, K. (2008) The novel adjuvant IC31® strongly improves influenza vaccine-specific cellular and humoral immune responses in young adult and aged mice, *Vaccine* 26(27-28), 3461-3468.

90) Rimaniol, A. C.; Gras, G.; Verdier, F.; Capel, F.; Grigoriev, V. B.; Porcheray, F.; Sauzeat, E.; Fournier, J. G.; Clayette, P.; Siegrist, C. A.; Dormont, D. (2004) Aluminum hydroxide adjuvant induces macrophage differentiation towards a specialized antigen-presenting cell type, *Vaccine* 22(23-24), 3127-3135.

91) Roberge, J. Y.; Beebe, X.; Danishefsky, S. J. (1995) A strategy for a convergent synthesis of N-linked glycopeptides on a solid support, *Science* 269(5221), 202-204.

92) Salazar, A. M.; Levy, H. B.; Ondra, S.; Kende, M.; Scherokman, B.; Brown, D.; Mena, H.; Martin, N.; Schwab, K.; Donovan, D.; Dougherty, D.; Pulliam, M.; Ippolito, M.; Graves, M.; Brown, H.; Ommaya, A. (1996) Long-term treatment of malignant gliomas with intramuscularly administered polyinosinic-polycytidylic acid stabilized with polylysine and carboxymethylcellulose: an open pilot study, *Neurosurgery* 38(6), 1096-1103, discussion at 1103-1104.

93) Salem, M. L.; Kadima, A. N.; Cole, D. J.; Gillanders, W. E. (2005) Defining the antigen-specific T-cell response to vaccination and poly(I:C)/TLR3 signaling: evidence of enhanced primary and memory CD8 T-cell responses and antitumor immunity, *J. Immunother.* 28(3), 220-228.

94) Salem, M. L.; El-Naggar, S. A.; Kadima, A.; Gillanders, W. E.; Cole, D. J. (2006) The adjuvant effects of the toll-like receptor 3 ligand polyinosinic-cytidylic acid poly (I:C) on antigen-specific CD8+ T cell responses are partially dependent on NK cells with the induction of a beneficial cytokine milieu, *Vaccine* 24(24), 5119-5132.

95) Sarma, P. S.; Shiu, G.; Neubauer, R. H.; Baron, S.; Huebner, R. J. (1969) Virus-induced sarcoma of mice: inhibition by a synthetic polyribonucleotide complex, *Proc. Natl. Acad. Sci. U.S.A.* 62(4), 1046-1051.

96) Sato, S.; Nomura, F.; Kawai, T.; Takeuchi, O.; Muhlradt, P. F.; Takeda, K.; Akira, S. (2000) Synergy and Cross-Tolerance Between Toll-Like Receptor (TLR) 2- and TLR4-Mediated Signaling Pathways, *J. Immunol.* 165 (12), 7096-7101.

97) Schellack, C.; Prinz, K.; Egyed, A.; Fritz, J. H.; Wittmann, B.; Ginzler, M.; Swatosch, G.; Zauner, W.; Kast, C.; Akira, S.; von Gabain, A.; Buschle, M.; Lingnau, K. (2006) IC31, a novel adjuvant signaling via TLR9, induces potent cellular and humoral immune responses, *Vaccine* 24(26), 5461-5472.

98) Schepens B; Sedeyn K; Vande Ginste L; De Baets S; Schotsaert M; Roose K; Houspie L; Van Ranst M; Gilbert B; Van Rooijen N; Fiers W; Piedra P; Saelens X. (2014) Protection and mechanism of action of a novel human respiratory syncytial virus vaccine candidate based on the extracellular domain of small hydrophobic protein, *EMBO Molecular Medicine* 6, 1436-54.

99) Schijns, V. E.; Lavelle, E. C. (2011) Trends in vaccine adjuvants, *Expert Rev. Vaccines* 10(4), 539-550.

100) Seya, T.; Akazawa, T.; Tsujita, T.; Matsumoto, M. (2006) Role of Toll-like receptors in adjuvant-augmented immune therapies, *Evid. Based Complement Alternat. Med* 3(1), 31-38.

101) Sloat, B. R.; Shaker, D. S.; Le, U. M.; Cui, Z. (2008) Nasal immunization with the mixture of PA63, LF, and a PGA conjugate induced strong antibody responses against all three antigens, *FEMS Immunol. Med Microbiol.* 52(2), 169-179.

102) Smith, T. F.; Waterman, M. S. (1981) Comparison of biosequences, *Adv. Appl. Math.* 2(4), 482-489.

103) Song, D. H.; Lee, J. O. (2012) Sensing of microbial molecular patterns by Toll-like receptors, *Immunol. Rev.* 250(1), 216-229.

104) Stegmann, T.; Kamphuis, T.; Meijerhof, T.; Goud, E.; de Haan, A.; Wilschut, J. (2010) Lipopeptide-adjuvanted respiratory syncytial virus virosomes: A safe and immunogenic non-replicating vaccine formulation, *Vaccine* 28(34), 5543-5550.

105) Stephen, E. L.; Sammons, M. L.; Pannier, W. L.; Baron, S.; Spertzel, R. O.; Levy, H. B. (1977) Effect of a nuclease-resistant derivative of polyriboinosinic-polyribocytidylic acid complex on yellow fever in rhesus monkeys (*Macaca mulatta*), *J. Infect. Dis.* 136(1), 122-126.

106) Stills, H. F., Jr. (2005) Adjuvants and antibody production: dispelling the myths associated with Freund's complete and other adjuvants, *ILAR J.* 46(3), 280-293.

107) Suet Ting Tan, R.; Lin, B.; Liu, Q.; Tucker-Kellogg, L.; Ho, B.; Leung, B. P.; Ling Ding, J. (2013) The synergy in cytokine production through MyD88-TRIF pathways is co-ordinated with ERK phosphorylation in macrophages, *Immunol. Cell Biol.* 91(5), 377-387.

108) Takeuchi, O.; Akira, S. (2010) Pattern recognition receptors and inflammation, *Cell* 140(6), 805-820.

109) Takeuchi, O.; Sato, S.; Horiuchi, T.; Hoshino, K.; Takeda, K.; Dong, Z.; Modlin, R. L.; Akira, S. (2002) Cutting edge: role of Toll-like receptor 1 in mediating immune response to microbial lipoproteins, *J. Immunol.* 169(1), 10-14.

110) Talmadge, J. E.; Adams, J.; Phillips, H.; Collins, M.; Lenz, B.; Schneider, M.; Chirigos, M. (1985) Immunotherapeutic potential in murine tumor models of polyinosinic-polycytidylic acid and poly-L-lysine solubilized by carboxymethylcellulose, *Cancer Res.* 45(3), 1066-1072.

111) Theriault, R. L.; Hortobagyi, G. N.; Buzdar, A. U.; Levy, H. B.; Hersh, E. M. (1986) Evaluation of polyinosinic-polycytidylic and poly-L-lysine in metastatic breast cancer, *Cancer Treat. Rep.* 70(11), 1341-1342.

112) Trumpfheller, C.; Caskey, M.; Nchinda, G.; Longhi, M. P.; Mizenina, O.; Huang, Y.; Schlesinger. S. J.; Colonna, M.; Steinman, R. M. (2008) The microbial mimic poly IC induces durable and protective CD4+ T cell immunity together with a dendritic cell targeted vaccine, *Proc. Natl. Acad. Sci. U.S.A.* 105(7), 2574-2579.

113) Tsuji, T.; Sabbatini, P.; Jungbluth, A. A.; Ritter, E.; Pan, L.; Ritter, G.; Ferran, L.; Spriggs, D.; Salazar, A. M.; Gnjatic, S. (2013) Effect of Montanide and poly-ICLC adjuvant on human self/tumor antigen-specific CD4+ T cells in phase I overlapping long peptide vaccine trial, *Cancer Immunol. Res.* 1(5), 340-350.

114) Vanhoutte, F.; Paget, C.; Breuilh, L.; Fontaine, J.; Vendeville, C.; Goriely, S.; Ryffel, B.; Faveeuw, C.; Trottein, F. (2008) Toll-like receptor (TLR)2 and TLR3 synergy and cross-inhibition in murine myeloid dendritic cells, *Immunol. Lett.* 116(1), 86-94.

115) Watters, T. M.; Kenny, E. F.; O'Neill, L. A. (2007) Structure, function and regulation of the Toll/IL-1 receptor adaptor proteins, *Immunol. Cell. Biol.* 85(6), 411-419.

116) Wells, J. W.; Cowled, C. J.; Farzaneh, F.; Noble, A. (2008) Combined triggering of dendritic cell receptors results in synergistic activation and potent cytotoxic immunity, *J. Immunol.* 181(5), 3422-3431.

117) Wiedemann, F.; Link, R.; Pumpe, K.; Jacobshagen, U.; Schaefer, H. E.; Wiesmuller, K. H.; Hummel, R. P.; Jung, G.; Bessler, W.; Boltz, T. (1991) Histopathological studies on the local reactions induced by complete Freund's adjuvant (CFA), bacterial lipopolysaccharide (LPS), and synthetic lipopeptide (P3C) conjugates, *J. Pathol.* 164(3), 265-271.

118) Webster, R. G.; Laver, W. G.; Air, G. M. Antigenic variation among type A influenza viruses, p. 127-168. In: Palese, P. & Kingsbury, D. W., eds. Genetics of influenza viruses. (New York: Springer-Verlag, 1983).

119) Welters, M. J.; Bijker, M. S.; van den Eeden, S. J.; Franken, K. L., Melief, C. J.; Offringa, R.; van der Burg, S. H. (2007) Multiple CD4 and CD8 T-cell activation parameters predict vaccine efficacy in vivo mediated by individual DC-activating agonists, *Vaccine* 25(8), 1379-1389.

120) Wilson-Welder, J. H.; Torres, M. P.; Kipper, M. J.; Mallapragada, S. K.; Wannemuehler, M. J.; Narasimhan, B. (2009) Vaccine adjuvants: current challenges and future approaches, *J. Pharm. Sci.* 98(4), 1278-1316.

121) Yoneyama, M.; Kikuchi, M.; Natsukawa, T.; Shinobu, N.; Imaizumi, T.; Miyagishi, M.; Taira, K.; Akira, S.; Fujita, T. (2004) The RNA helicase RIG-I has an essential function in double-stranded RNA-induced innate antiviral responses, *Nat. Immunol.* 5(7), 730-737.

122) Zaks, K.; Jordan, M.; Guth, A.; Sellins, K.; Kedl, R.; Izzo, A.; Bosio, C.; Dow, S. (2006) Efficient immunization and cross-priming by vaccine adjuvants containing TLR3 or TLR9 agonists complexed to cationic liposomes, *J. Immunol.* 176(12), 7335-7345.

123) Zhu, Q.; Egelston, C.; Vivekanandhan, A.; Uematsu, S.; Akira, S.; Klinman, D. M.; Belyakov, I. M.; Berzofsky, J. A. (2008) Toll-like receptor ligands synergize through distinct dendritic cell pathways to induce T cell responses: implications for vaccines, *Proc. Natl. Acad. Sci. U.S.A.* 105(42), 16260-16265.

124) Zhu, X.; Nishimura, F.; Sasaki, K.; Fujita, M.; Dusak, J. E.; Eguchi, J.; Fellows-Mayle, W.; Storkus, W. J.; Walker, P. R.; Salazar, A. M.; Okada, H. (2007) Toll like receptor-3 ligand poly-ICLC promotes the efficacy of peripheral vaccinations with tumor antigen-derived peptide epitopes in murine CNS tumor models, *J. Transl. Med.* 5(10), 1-15.

125) Zhu, X.; Fallert-Junecko, B. A.; Fujita, M.; Ueda, R.; Kohanbash, G.; Kastenhuber, E. R.; McDonald, H. A.; Liu, Y.; Kalinski, P.; Reinhart, T. A.; Salazar, A. M.; Okada, H. (2010) Poly-ICLC promotes the infiltration of effector T cells into intracranial gliomas via induction of CXCL10 in IFN-alpha and IFN-gamma dependent manners, *Cancer Immunol. Immunother.* 59(9), 1401-1409.

The invention claimed is:

1. An adjuvanting system comprising:
   (a) a polyI:C polynucleotide adjuvant in an amount of less than about 100 micrograms per unit dose for humans;
   (b) a lipid-based adjuvant in an amount of less than about 100 micrograms per unit dose for humans, wherein the lipid-based adjuvant is PAM$_3$Cys-Ser-(Lys)$_4$ (SEQ ID NO: 1);
   (c) an amphipathic compound; and
   (d) a hydrophobic carrier, wherein the hydrophobic carrier is an oil or a mixture of oils selected from a vegetable oil, nut oil, and mineral oil, or the hydrophobic carrier is a mannide oleate in mineral oil solution.

2. A composition comprising the adjuvanting system of claim 1 and an antigen, wherein the composition is water-free or substantially free of water.

3. The composition of claim 2, wherein a composition that is substantially free of water comprises less than about 10% water on a weight/weight basis of the total weight of the carrier.

4. The composition of claim 2, wherein the polyI:C polynucleotide adjuvant:
   i) comprises RNA, DNA or a combination thereof;
   ii) is double-stranded and each strand is a homopolymer of inosinic or cytidylic residues or is double-stranded and each strand is a heteropolymer comprising both inosinic and cytidylic residues; and/or
   iii) is a mixture comprising both homopolymeric polyI:C polynucleotides and heteropolymeric polyI:C polynucleotides.

5. The composition of claim 2, wherein the amphipathic compound is dioleoyl phosphatidylcholine (DOPC), a mixture of phospholipids comprising DOPC, lecithin, or a mixture of phospholipids comprising lecithin.

6. The composition of claim 5, wherein the lipids form a closed vesicular structure around the antigen, wherein the closed vesicular structure is a single layer vesicular structure or a bilayer vesicular structure.

7. The composition of claim 2, wherein the polyI:C polynucleotide adjuvant is a mixture of varying strand lengths of polyI and polyC, said mixture comprising an average molecular weight of 989,486 Daltons, and the hydrophobic carrier is a mannide oleate in mineral oil solution.

8. The composition of claim 2, wherein the antigen is a polypeptide; a polynucleotide encoding a polypeptide; a carbohydrate; a microorganism or a part thereof; or a toxin.

9. The composition of claim 8, wherein the antigen is derived from a virus, derived from a bacterium, derived from a protozoan, or derived from a membrane surface-bound cancer antigen.

10. The composition of claim 9, wherein the antigen is:
   i) a peptide antigen comprising an amino acid sequence from the survivin protein (SEQ ID NO: 69) or a modified variant thereof; or a nucleic acid molecule encoding said peptide antigen;
   ii) a peptide antigen comprising an amino acid sequence selected from FEELTLGEF (SEQ ID NO: 70); FTELTLGEF (SEQ ID NO: 71); LTLGEFLKL (SEQ ID NO: 72); LMLGEFLKL (SEQ ID NO: 73); RISTFKNWPF (SEQ ID NO: 74); RISTFKNWPK (SEQ ID NO: 75); STFKNWPFL (SEQ ID NO: 76); or LPPAWQPFL (SEQ ID NO: 77), or any combination thereof; or a nucleic acid molecule encoding said peptide antigen; or
   iii) a mixture of five peptide antigens comprising the amino acid sequence: FTELTLGEF (SEQ ID NO: 71); LMLGEFLKL (SEQ ID NO: 73); RISTFKNWPK (SEQ ID NO: 75); STFKNWPFL (SEQ ID NO: 76); and LPPAWQPFL (SEQ ID NO: 77).

11. The composition of claim 2, wherein the antigen comprises at least one B cell epitope, at least one CTL epitope or a combination thereof.

12. The composition of claim 2 further comprising a T-helper epitope.

13. The composition of claim 12, wherein the T-helper epitope is pan-DR epitope (PADRE) comprising the amino acid sequence AKXVAAWTLKAAA (SEQ ID NO: 79); Tetanus toxoid peptide F21E comprising the amino acid sequence FNNFTVSFWLRVPKVSASHLE (SEQ ID NO: 80); or modified Tetanus toxin peptide A16L comprising the amino acid sequence AQYIKANSKFIGITEL (SEQ ID NO: 78); wherein the T-helper epitope is optionally conjugated or fused to the antigen.

14. The composition of claim 2, wherein the polyI:C polynucleotide adjuvant is a Toll-like receptor 3 (TLR3) agonist and the lipid-based adjuvant is an agonist of the TLR1/2 heterodimer.

15. The composition of claim 2, which is capable of inducing an antibody immune response and/or cell-mediated immune response with a single dose.

16. The composition of claim 2, comprising less than about 50 micrograms of the polyI:C polynucleotide adjuvant and less than about 50 micrograms of the lipid-based adjuvant per unit dose for humans.

17. The composition of claim 2, comprising less than about 10 micrograms of the polyI:C polynucleotide adjuvant and less than about 10 micrograms of the lipid-based adjuvant per unit dose for humans.

18. The composition of claim 2, comprising less than about 5 micrograms of the polyI:C polynucleotide adjuvant and less than about 5 micrograms of the lipid-based adjuvant per unit dose for humans.

19. The composition of claim 2, comprising less than about 2 micrograms of the polyI:C polynucleotide adjuvant and less than about 2 micrograms of the lipid-based adjuvant per unit dose for humans.

20. A kit comprising, in one or more separate containers, a polyI:C polynucleotide adjuvant in an amount of less than about 100 micrograms per unit dose for humans; a lipid-based adjuvant in an amount of less than about 100 micrograms per unit dose f humans; an amphipathic compound; and a hydrophobic carrier, wherein:
  i) the polyI:C polynucleotide adjuvant; the lipid-based adjuvant; the amphipathic compound; and the hydrophobic carrier are each in a separate container;
  ii) the polyI:C polynucleotide adjuvant; the lipid-based adjuvant; and the amphipathic compound are together in a first container and the hydrophobic carrier is in a second container;
  iii) the polyI:C polynucleotide adjuvant and the lipid-based adjuvant are together in a first container; the amphipathic compound is in a second container; and the hydrophobic carrier is in a third container;
  iv) the polyI:C polynucleotide adjuvant and the lipid-based adjuvant are together in a first container and the amphipathic compound and the hydrophobic carrier are together in a second container; or
  v) the polyI:C polynucleotide adjuvant is in a first container, the lipid-based adjuvant is in a second container, and the amphipathic compound and the hydrophobic carrier are together in a third container, wherein the lipid-based adjuvant is $PAM_3Cys$-Ser-$(Lys)_4$ (SEO ID NO: 1), and wherein the hydrophobic carrier is an oil or a mixture of oils selected from a vegetable oil, nut oil, and mineral oil, or the hydrophobic carrier is a mannide oleate in mineral oil solution.

21. The kit of claim 20 further comprising:
  i) an antigen, wherein the antigen is together in the container with any one or more of the polyI:C polynucleotide adjuvant, the lipid-based adjuvant, the amphipathic compound, the hydrophobic carrier, and/or any mixture thereof, or the antigen is in a separate container;
  ii) a T-helper epitope, wherein the T-helper epitope is together in the container with any one or more of the polyI:C polynucleotide adjuvant, the lipid-based adjuvant, the amphipathic compound, the hydrophobic carrier, the antigen and/or any mixture thereof, or the T helper is in a separate container, wherein the T-helper epitope is optionally conjugated or fused to the antigen and when so is in the same container as the antigen; and/or
  iii) instructions for use in preparing a pharmaceutical composition and/or instructions for use in inducing an antibody response and/or cell-mediated immune response in a subject.

22. The kit of claim 20, which is for use in preparing a composition that is water-free or substantially free of water, wherein the composition that is substantially free of water comprises less than about 10% water on a weight/weight basis of the total weight of the carrier.

23. A method comprising administering the composition of claim 2 to a subject in need thereof, wherein the subject is human.

24. The method according to claim 23, which is a method for inducing an antibody response and/or cell-mediated immune response to said antigen in said subject.

25. The method according to claim 24, which is a method for the treatment and/or prevention of a disease caused by a bacteria, a virus, a fungus, a parasite, an allergen, or a tumor cell that expresses the antigen.

26. The method according to claim 25, wherein the disease is influenza, a respiratory tract infection caused by human respiratory syncytial virus, pertussis, anthrax, malaria, or cancer.

27. The method according to claim 24, which is a method for the treatment and/or prevention of a neurodegenerative disease, wherein the neurodegenerative disease is associated with expression of the antigen.

28. A method for neutralizing a toxin, virus, bacterium or allergen, with an antibody, said method comprising administering the composition of claim 2 to a subject, wherein the subject is human.

* * * * *